(12) United States Patent
Yoder et al.

(10) Patent No.: US 10,898,579 B2
(45) Date of Patent: Jan. 26, 2021

(54) CONJUGATES OF CYSTEINE ENGINEERED ANTIBODIES

(71) Applicant: ImmunoGen, Inc., Waltham, MA (US)

(72) Inventors: Nicholas C. Yoder, Brookline, MA (US); Chen Bai, Arlington, MA (US); Michael Louis Miller, Framingham, MA (US)

(73) Assignee: IMMUNOGEN, INC., Waltham, MA (US)

(*) Notice: Subject to any disclaimer, the term of this patent is extended or adjusted under 35 U.S.C. 154(b) by 531 days.

(21) Appl. No.: 15/195,269

(22) Filed: Jun. 28, 2016

(65) Prior Publication Data

US 2017/0014522 A1      Jan. 19, 2017

Related U.S. Application Data

(60) Provisional application No. 62/338,245, filed on May 18, 2016, provisional application No. 62/186,254, filed on Jun. 29, 2015.

(51) Int. Cl.
| | | |
|---|---|---|
| *A61K 47/68* | (2017.01) | |
| *C07D 243/26* | (2006.01) | |
| *C07D 487/04* | (2006.01) | |
| *C07K 16/28* | (2006.01) | |
| *C07D 519/00* | (2006.01) | |
| *C07K 16/30* | (2006.01) | |
| *A61K 39/00* | (2006.01) | |

(52) U.S. Cl.
CPC ...... *A61K 47/6803* (2017.08); *A61K 47/6849* (2017.08); *C07D 519/00* (2013.01); *C07K 16/2866* (2013.01); *C07K 16/3069* (2013.01); *A61K 2039/505* (2013.01); *C07K 2317/24* (2013.01); *C07K 2317/526* (2013.01); *C07K 2317/90* (2013.01)

(58) Field of Classification Search
None
See application file for complete search history.

(56) References Cited

U.S. PATENT DOCUMENTS

| 8,557,966 | B2 | 10/2013 | Ab et al. |
|---|---|---|---|
| 2007/0092940 | A1 | 4/2007 | Eigenbrot et al. |
| 2009/0010945 | A1 | 1/2009 | Alley et al. |
| 2012/0213705 | A1 | 8/2012 | Dimasi et al. |
| 2015/0359903 | A1 | 12/2015 | Widdison |
| 2015/0359904 | A1 | 12/2015 | Widdison |
| 2017/0029514 | A1 | 2/2017 | Kovtun et al. |

FOREIGN PATENT DOCUMENTS

| EP | 2425860 A1 | 3/2012 |
|---|---|---|
| WO | 1996/14339 A1 | 5/1996 |
| WO | 2010/091150 A1 | 8/2010 |
| WO | 2012/128868 A1 | 9/2012 |
| WO | 2014/134457 A2 | 9/2014 |
| WO | 2015/196089 A1 | 12/2015 |
| WO | 2015/196167 A1 | 12/2015 |
| WO | 2016/036861 A1 | 3/2016 |
| WO | 2016/141285 A1 | 9/2016 |
| WO | 2017/004026 A1 | 1/2017 |

OTHER PUBLICATIONS

Kumaresan et al., Evaluation of ketone-oxime method for developing therapeutic on-demand cleavable immunoconjugates. Bioconjug Chem. Jun. 2008;19(6):1313-8.
Rodwell et al., Site-specific covalent modification of monoclonal antibodies: in vitro and in vivo evaluations. Proc Natl Acad Sci U S A. Apr. 1986;83(8):2632-6.
Stimmel et al., Site-specific conjugation on serine right-arrow cysteine variant monoclonal antibodies. J Biol Chem. Sep. 2000;275(39):30445-50.

*Primary Examiner* — Karl J Puttlitz
*Assistant Examiner* — Kauser M Akhoon
(74) *Attorney, Agent, or Firm* — McCarter & English, LLP; Xin Zhang

(57) ABSTRACT

The invention relates to novel cell-binding agent-cytotoxic agent conjugates, wherein the cell-binding agent (CBA) is covalently linked to the cytotoxic agent through an engineered Cys, such as an engineered Cys in the heavy chain CH3 domain, at a position corresponds to the EU/OU numbering position 442 (or C442) on an antibody CBA. The invention also provides methods of preparing the conjugates of the present invention. The invention further provides composition and methods useful for inhibiting abnormal cell growth or treating a proliferative disorder in a mammal using the conjugates of the invention.

11 Claims, 12 Drawing Sheets
Specification includes a Sequence Listing.

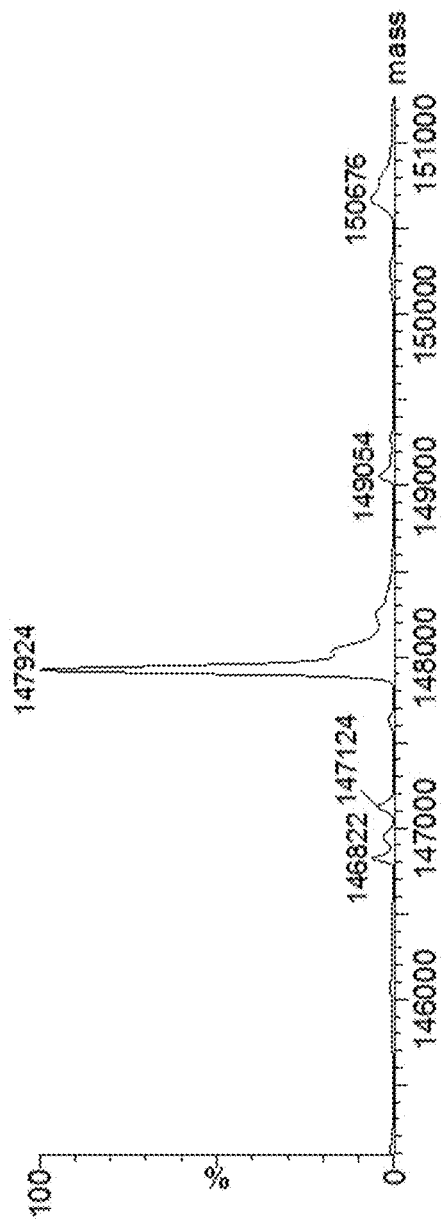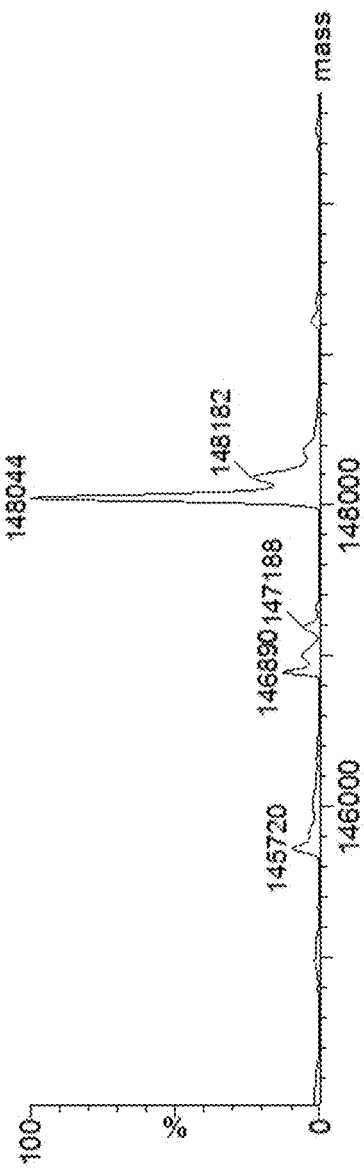

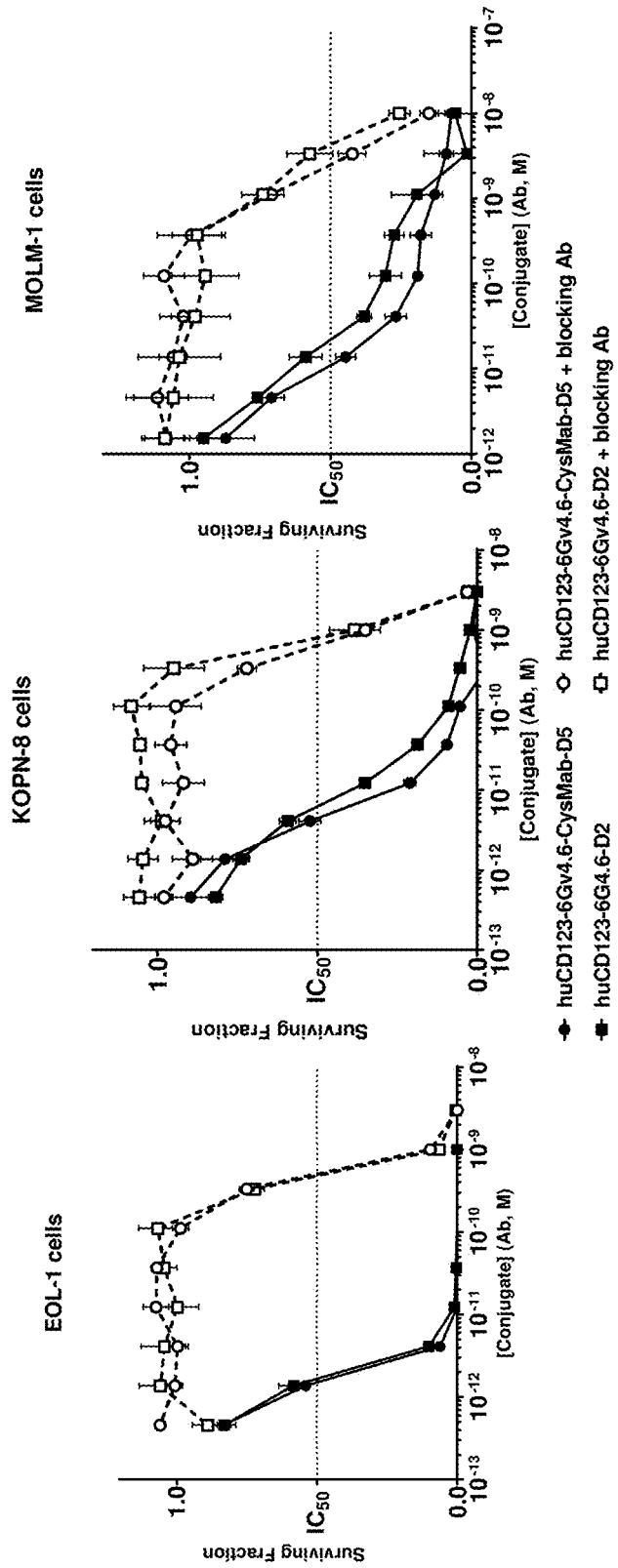

CONJUGATES OF CYSTEINE ENGINEERED ANTIBODIES

REFERENCE TO RELATED APPLICATIONS

This application claims the benefit of the filing date, under 35 U.S.C. § 119(e), of U.S. Provisional Application No. 62/186,254, filed on Jun. 29, 2015, and U.S. Provisional Application No. 62/338,245, filed on May 18, 2016. The entire contents of each of the above-referenced applications are incorporated herein by reference.

FIELD OF THE INVENTION

The present invention generally relates to conjugates of cysteine engineered antibodies. The present invention also relates to methods of using such conjugates for treating diseases, such as cancer.

BACKGROUND OF THE INVENTION

Antibody-cytotoxic agent conjugates (or "antibody-drug conjugates (ADC)") and cell binding agent-drug conjugates are emerging as a powerful class of anti-tumor agents with efficacy across a range of cancers. Cell binding agent-drug conjugates (such as ADCs) are commonly composed of three distinct elements: a cell-binding agent (e.g., an antibody); a linker; and a cytotoxic moiety. Conventionally, the cytotoxic drug moiety is covalently attached to lysines on the antibody, resulting in conjugates that are heterogeneous mixtures of ADCs bearing varying numbers of drugs attached at different positions on the antibody molecule.

SUMMARY OF THE INVENTION

The present invention provides site-specific antibody-cytotoxic agent conjugates, wherein the cytotoxic agent is covalently attached to one or more cysteine residues on the antibody. Specifically, the cysteine residue is located at position 442 of the heavy chain(s) according to the EU/OU numbering. The site-specific antibody-cytotoxic agent conjugates of the present invention have unexpectedly improved tolerability while maintaining similar potency, resulting in a higher therapeutic index (ratio of maximum tolerated dose to minimum effective dose) as compared to the lysine-linked conjugates (Abstract #645, AACR Annual Meeting, Apr. 18-22, 2015).

Thus one aspect of the invention provides an antibody-cytotoxic agent conjugate represented by the following formula:

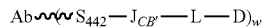

or a pharmaceutically acceptable salt thereof, wherein:
Ab is an antibody having a cysteine residue at position 442 of a heavy chain of the antibody (EU/OU numbering), and is covalently linked to a linking moiety $J_{CB}'$ through the thiol group $S_{442}$ of the cysteine residue;
D is a cytotoxic agent covalently linked to a linker L that is covalently linked to $J_{CB}'$; and,
w is 1 or 2.

In certain embodiments, w is 2. Alternatively, w is 1.
In certain embodiments, the cysteine residue at position 442 is recombinantly introduced into said Ab.

In certain embodiments, $J_{CB}'$ is

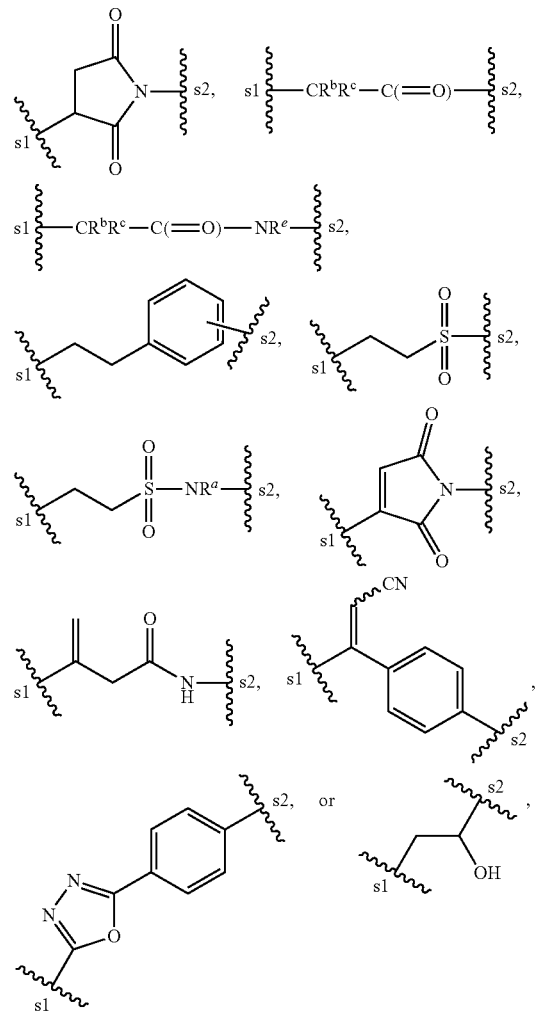

wherein:
s1 is the site covalently linked to the cysteine residue, and s2 is the site covalently linked to the group L; and,
$R^a$, $R^b$, $R^c$, and $R^e$, for each occurrence, are independently H or an optionally substituted alkyl, preferably, $R^a$, $R^b$, $R^c$, and $R^e$ are each H.

In certain embodiments, $J_{CB}'$ is

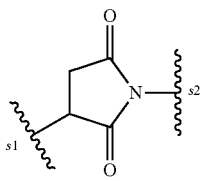

In certain embodiments, -L- is represented by the following structural formula:

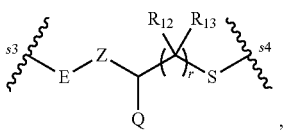

wherein:
s3 is the site covalently linked to $J_{CB}'$, and s4 is the site covalently linked to D;

E is —(CR$_{10}$R$_{11}$)$_q$—, cycloalkyl, or cycloalkylalkyl;

Z is absent, —SO$_2$NR$_9$—, —NR$_9$SO$_2$—, —C(=O)—NR$_9$—, —NR$_9$—C(=O)—, —C(=O)—O—, —O—C(=O)—, —C(=O)—NR$_9$—(CH$_2$CH$_2$O)—, —NR$_9$—C(=O)—(CH$_2$CH$_2$O)—, —(OCH$_2$CH$_2$)$_p$—C(=O)NR$_9$—, or —(OCH$_2$CH$_2$)$_p$—NR$_9$—C(=O)—;

p is an integer from 1 to 24;

Q is H, a charged substituent, or an ionizable group;

R$_9$, R$_{10}$, R$_{11}$, R$_{12}$, and R$_{13}$, for each occurrence, are independently H or an optionally substituted alkyl; and, q and r, for each occurrence, are independently an integer between 0 and 10.

In certain embodiments, E is —(CR$_{10}$R$_{11}$)$_q$—.

In certain embodiments, E is

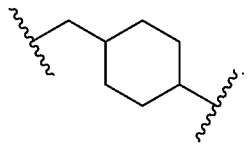 [SMILES: *CC1CCC(*)CC1]

In certain embodiments, Z is —C(=O)—NR$_9$— or —NR$_9$—C(=O)—; in certain embodiments, R$_9$ is —H.

In certain embodiments, Q is:

i) H;

ii) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{14}$R$_{15}$, or a pharmaceutically acceptable salt thereof; or, iii) —N$^+$R$_{14}$R$_{15}$R$_{16}$X$^-$ or —Z'—NR$_{14}$R$_{15}$R$_{16}$X;

Z' is an optionally substituted alkylene, an optionally substituted cycloalkylene, or an optionally substituted phenylene; preferably, Z' is an optionally substituted alkylene;

R$_{14}$, R$_{15}$ and R$_{16}$ are each independently an optionally substituted alkyl; and, X$^-$ is a pharmaceutically acceptable anion.

In certain embodiments, Q is H or —SO$_3$M, wherein M is H$^+$, Na$^+$ or K$^+$.

In certain embodiments, R$_9$, R$_{10}$, R$_{11}$, R$_{12}$, and R$_{13}$ are all H; and q and r are each independently an integer between 1 and 6.

In certain embodiments, -J$_{CB}$'-L- is represented by any one of the following structural formulae:

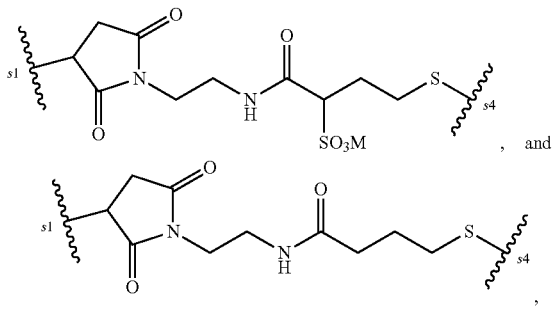

wherein M is H$^+$ or a pharmaceutically acceptable cation.

In certain embodiments, -L- is represented by the following structural formula:

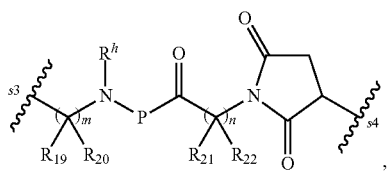

wherein:

s3 is the site covalently linked to J$_{CB}$', and s4 is the site covalently linked to D;

R$_{19}$ to R$_{22}$, for each occurrence, are independently H or an optionally substituted alkyl;

m and n are each independently an integer between 0 and 10;

R$^h$ is H or an optionally substituted alkyl;

P is an optionally substituted alkylene, —(CH$_2$—CH$_2$—O)$_j$— (wherein the oxygen atom is connected to the —(C=O)— group connected to P), an amino acid residue or a peptide containing 2 to 20 amino acid residues; and j is an integer from 1 to 24.

In certain embodiments, R$_{19}$, R$_{20}$, R$_{21}$ and R$_{22}$ are each H; and m and n are each independently an integer between 1 and 6.

In certain embodiments, P is an amino acid residue or a peptide containing 2 to 10 amino acid residues; preferably, P is a peptide containing 2 to 5 amino acid residues.

In certain embodiments, each amino acid residue is the residue of an amino acid independently selected from: a naturally occurring amino acid, a synthetic amino acid, an amino acid analog, and an amino acid mimetic that functions in a manner similar to the naturally occurring amino acids.

In certain embodiments, each amino acid residue is the residue of an amino acid independently selected from the group consisting of: Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Proline, Serine, Tyrosine, N-methyl-Histidine, N-methyl-Alanine, N-methyl-Isoleucine, N-methyl-Arginine, N-methyl-Leucine, N-methyl-Asparagine, N-methyl-Lysine, N-methyl-Aspartic acid, N-methyl-Methionine, N-methyl-Cysteine, N-methyl-Phenylalanine, N-methyl-Glutamic acid, N-methyl-Threonine, N-methyl-Glutamine, N-methyl-Tryptophan, N-methyl-Glycine, N-methyl-Valine, N-methyl-Proline, N-methyl-Serine, N-methyl-Tyrosine, hydroxyproline, γ-carboxyglutamate, selinocysteine, O-phosphoserine, homoserine, norleucine, methionine sulfoxide, methionine methyl sulfonium, citrulline, Ornithine, cysteine sulfonic acid, cysteine sulfinic acid, 3-aminoalanine, 3-dimethylaminoalanine, 2-amino-4-(dimethylamino)butanoic acid, 2,4-diaminobutanoic acid, 2-amino-6-(dimethylamino)hexanoic acid, 2-amino-5-(dimethylamino)pentanoic acid, and β-alanine, each independently as an L or D isomer. Preferably, each amino acid residue is the residue of an independently selected glycine or alanine.

In certain embodiments, P is a peptide cleavable by a protease.

In certain embodiments, P is selected from the group consisting of: Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 14), 3-Ala-Leu-Ala-Leu (SEQ ID NO: 15), Gly-Phe-Leu-Gly (SEQ ID NO: 16), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, and D-Ala-D-Ala., Gly-Gly-Gly, Ala-Ala-Ala, D-Ala-Ala-Ala, Ala-D-Ala-Ala, Ala-Ala-D-Ala, Ala-Val-Cit, Ala-Val-Ala, and β-Ala-Gly-Gly-Gly. For example, P may be Gly-Gly-Gly, Ala-Ala-Ala, D-Ala-Ala-Ala, Ala-D-Ala-Ala, Ala-Val-Ala, or β-Ala-Gly-Gly-Gly.

In certain embodiments, -J$_{CB}$'-L- is represented by the following structural formula:

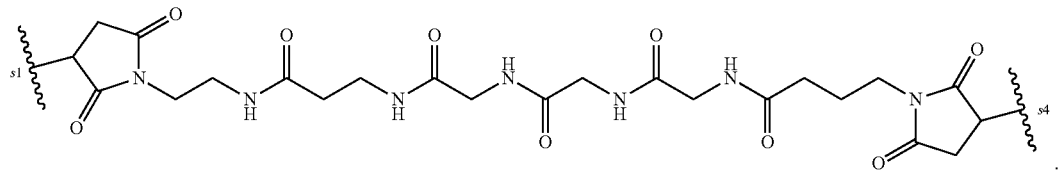 [SMILES: *C1CC(=O)N(CCCC(=O)NCC(=O)NCC(=O)NCC(=O)NCCC(=O)NCCN2C(=O)CC(*)C2=O)C1=O]

In certain embodiments, -L- is represented by the following structural formula:

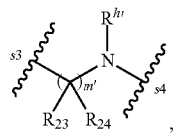

wherein:
s3 is the site covalently linked to J$_{CB}$', and s4 is the site covalently linked to D;
R$_{23}$ and R$_{24}$, for each occurrence, are independently H or an optionally substituted alkyl;
m' is an integer between 0 and 10; and
R$^{h'}$ is H or an optionally substituted alkyl.

In certain embodiments, R$_{23}$ and R$_{24}$ are both H; and m' is an integer between 1 and 6.

In certain embodiments, R$^{h'}$ is H.

In certain embodiments, -J$_{CB}$'-L- is represented by the following structural formula:

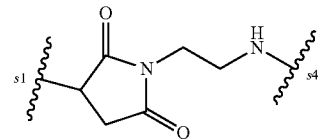

In certain embodiments, D is a benzodiazepine compound, such as an indolinobenzodiazepine compound.

In certain embodiments, D is represented by the following structural formula:

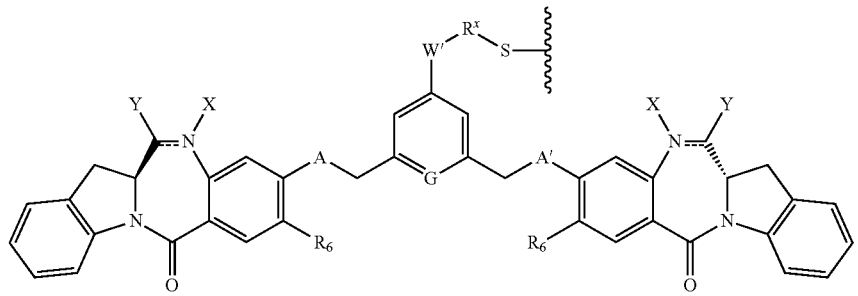

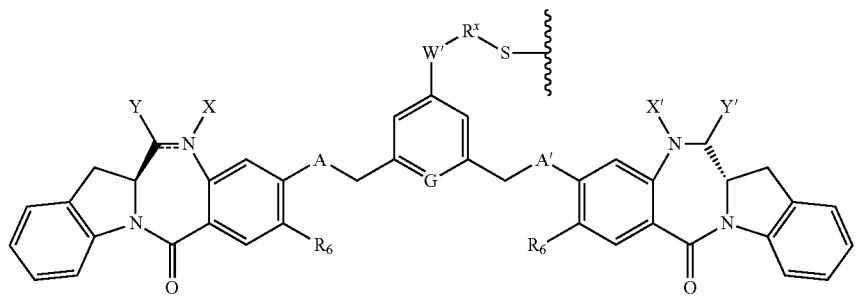

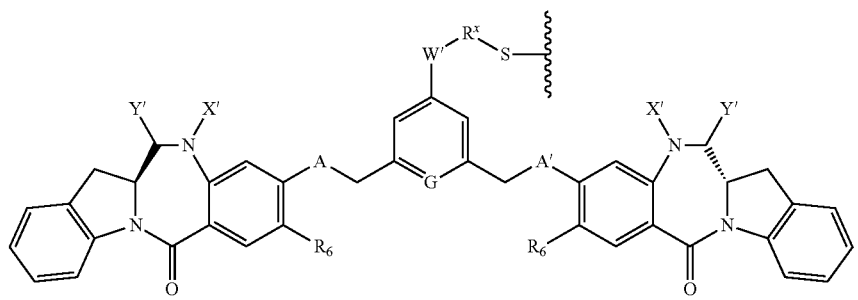

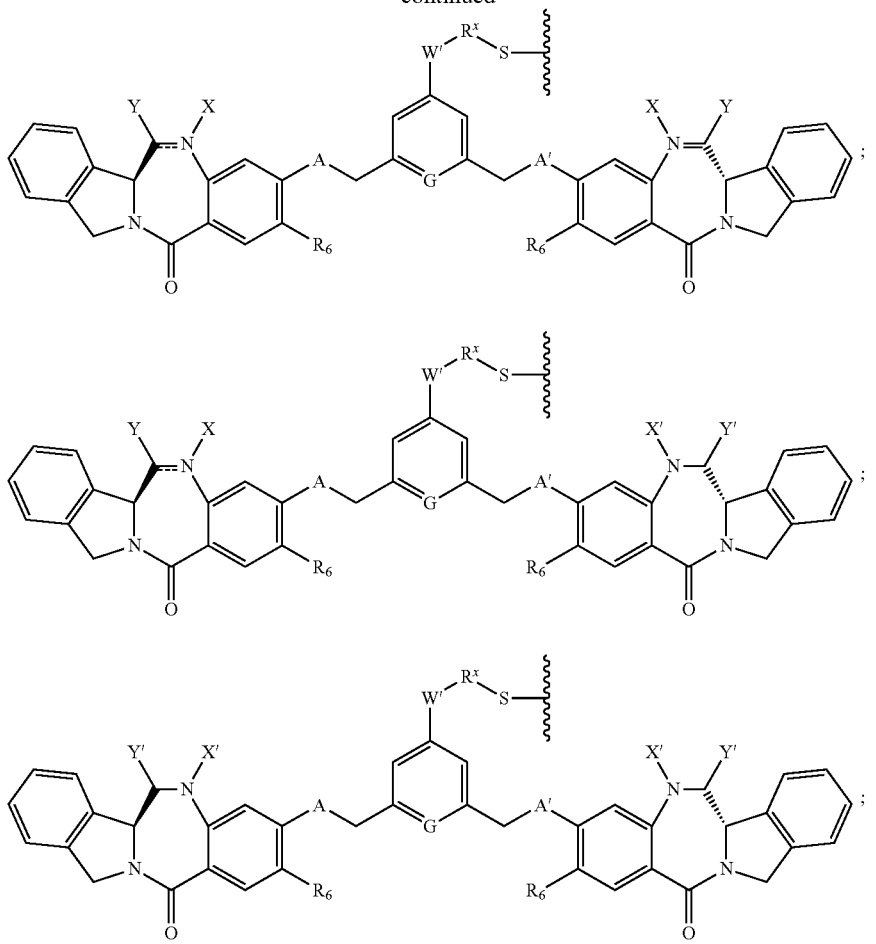

or a pharmaceutically acceptable salt thereof, wherein:
the double line == between N and C represents a single bond or a double bond, provided that when it is a double bond, X is absent and Y is —H, and when it is a single bond, X is selected from —H, or an amine protecting group; and Y is selected from —OR, —OCOR', —SR, —NR'R", —SO$_3$M, —SO$_2$M or —OSO$_3$M, wherein M is —H or a cation;

R is —H, an optionally substituted linear, branched or cyclic alkyl, alkenyl or alkynyl having from 1 to 10 carbon atoms or a PEG group —(CH$_2$CH$_2$O)$_n$—R$^c$, wherein n is an integer from 1 to 24, and R$^c$ is a linear or branched alkyl having 1 to 4 carbon atoms;

R' and R" are each independently selected from —H, —OH, —OR, —NRR', —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—R$^c$, and R$^{g'}$ is —H, an optionally substituted linear, branched or cyclic alkyl, alkenyl or alkynyl having from 1 to 10 carbon atoms or a PEG group —(CH$_2$CH$_2$O)$_n$—R$^c$;

X' is selected from the group consisting of —H, —OH, a substituted or unsubstituted linear, branched or cyclic alkyl, alkenyl or alkynyl having from 1 to 10 carbon atoms, phenyl, and an amine-protecting group;

Y' is selected from the group consisting of —H, an oxo group (i.e., Y' together with the carbon atom to which it is attached form a —C(=O)— group), a substituted or unsubstituted linear, branched or cyclic alkyl, alkenyl or alkynyl having from 1 to 10 carbon atoms;

A and A' are selected from —O— and —S—;

W' is absent, or selected from —O—, —N(R$^e$)—, —N(R$^e$)—C(=O)—, —N(C(=O)R$^e$)—, —S— or —CH$_2$—S—, —CH$_2$NR$^e$—;

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{11}$R$^{102}$) group or a 5- or 6-membered nitrogen containing heterocycle, wherein R$^{101}$ and R$^{102}$ are each independently a linear, branched, or cyclic alkyl, alkenyl or alkynyl having 1 to 10 carbon atoms;

G is selected from —CH— or —N—; and

R$_6$ is —H, —R, —OR, —SR, —NR'R", —NO$_2$, or halogen.

In certain embodiments, D is represented by the following structural formula:

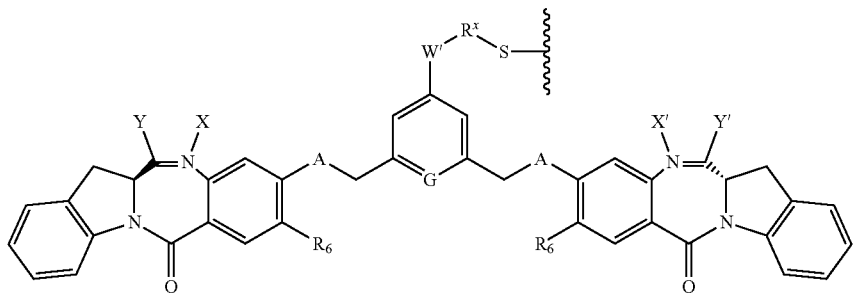

In certain embodiments:
the double line == between N and C represents a single bond or a double bond, provided that when it is a double bond, X is absent and Y is —H, and when it is a single bond, X is —H, and Y is —OH or —SO$_3$M;
M is —H or a pharmaceutically acceptable cation;
X' and Y' are both —H;

A and A' are both —O—;
R$_6$ is —OMe; and
R$^x$ is a linear or branched alkyl having 1 to 6 carbon atoms.

In certain embodiments, D is represented by the following structural formula:

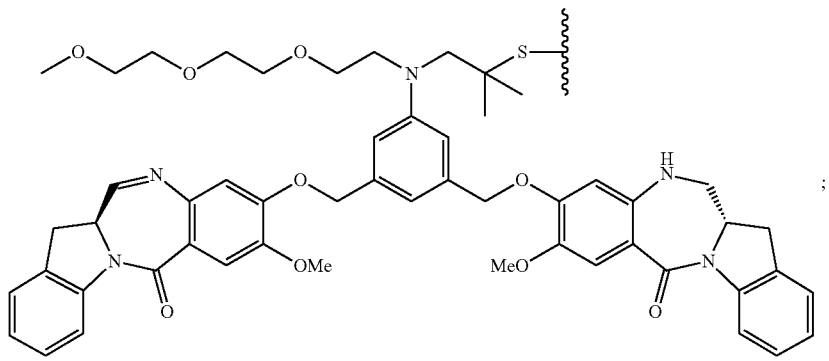

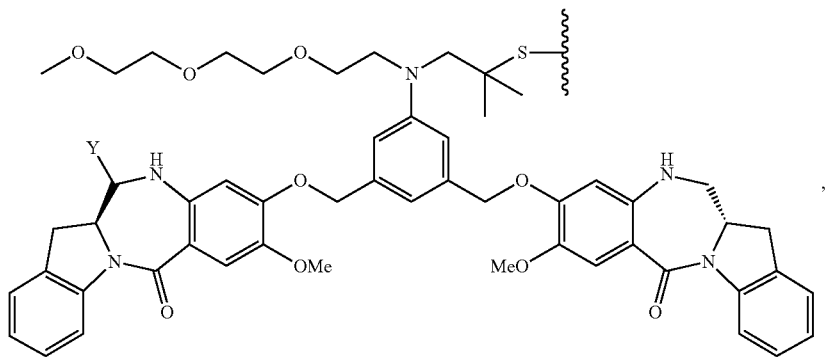

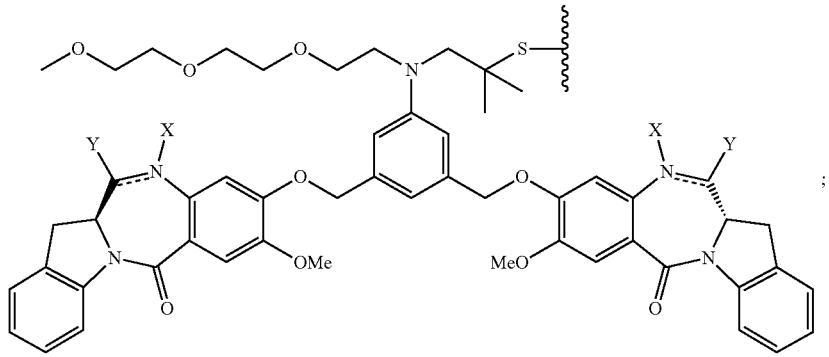

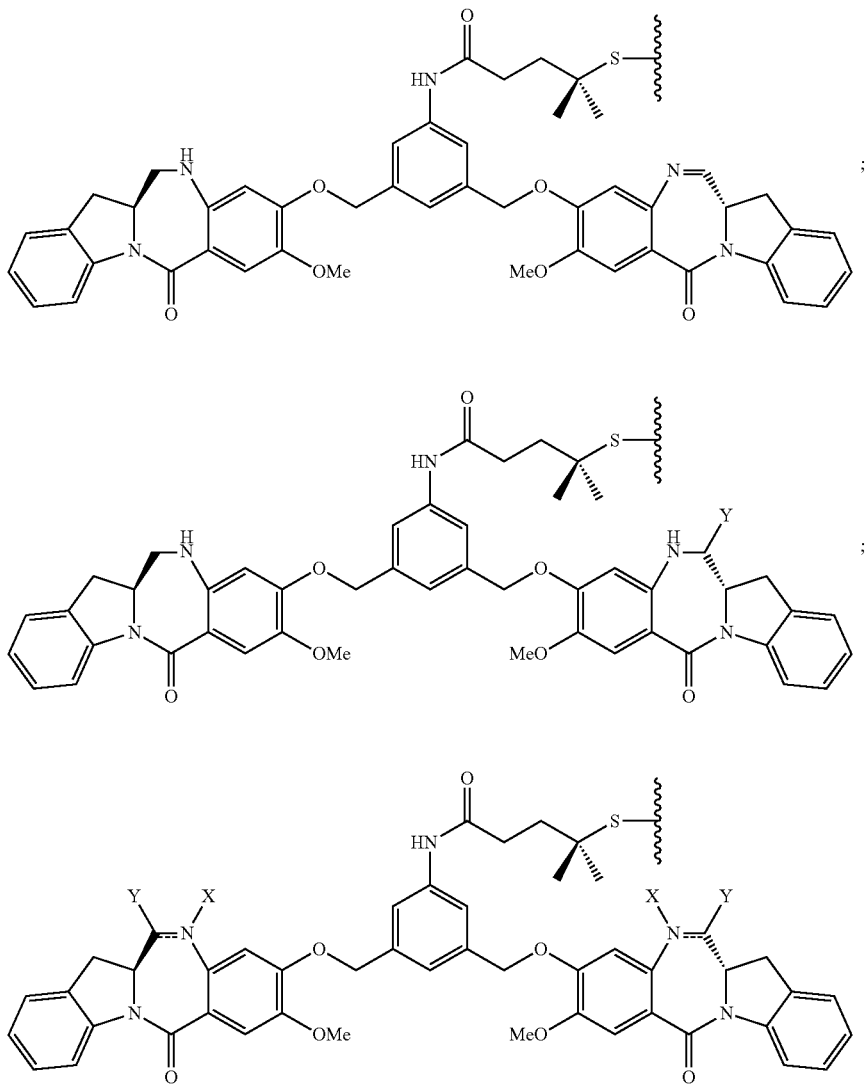

or a pharmaceutically acceptable salt thereof, wherein the double line === between N and C represents a single bond or a double bond, provided that when it is a double bond, X is absent and Y is —H, and when it is a single bond, X is —H, and Y is —SO₃M; and M is H⁺ or a pharmaceutically acceptable cation.

In certain embodiments, Y is —SO₃M, and M is H⁺, Na⁺ or K⁺.

In certain embodiments, D is represented by the following structural formula:

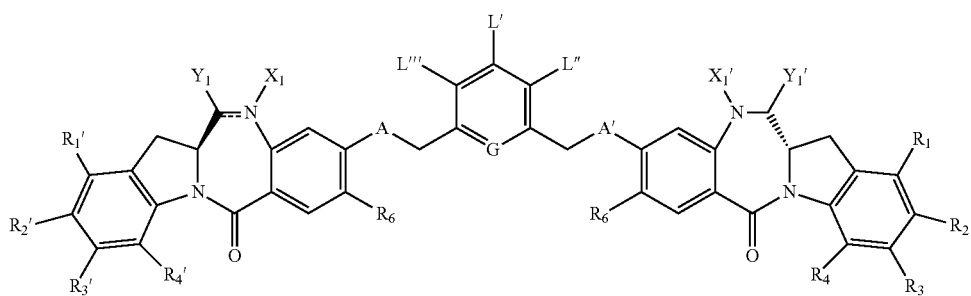

-continued

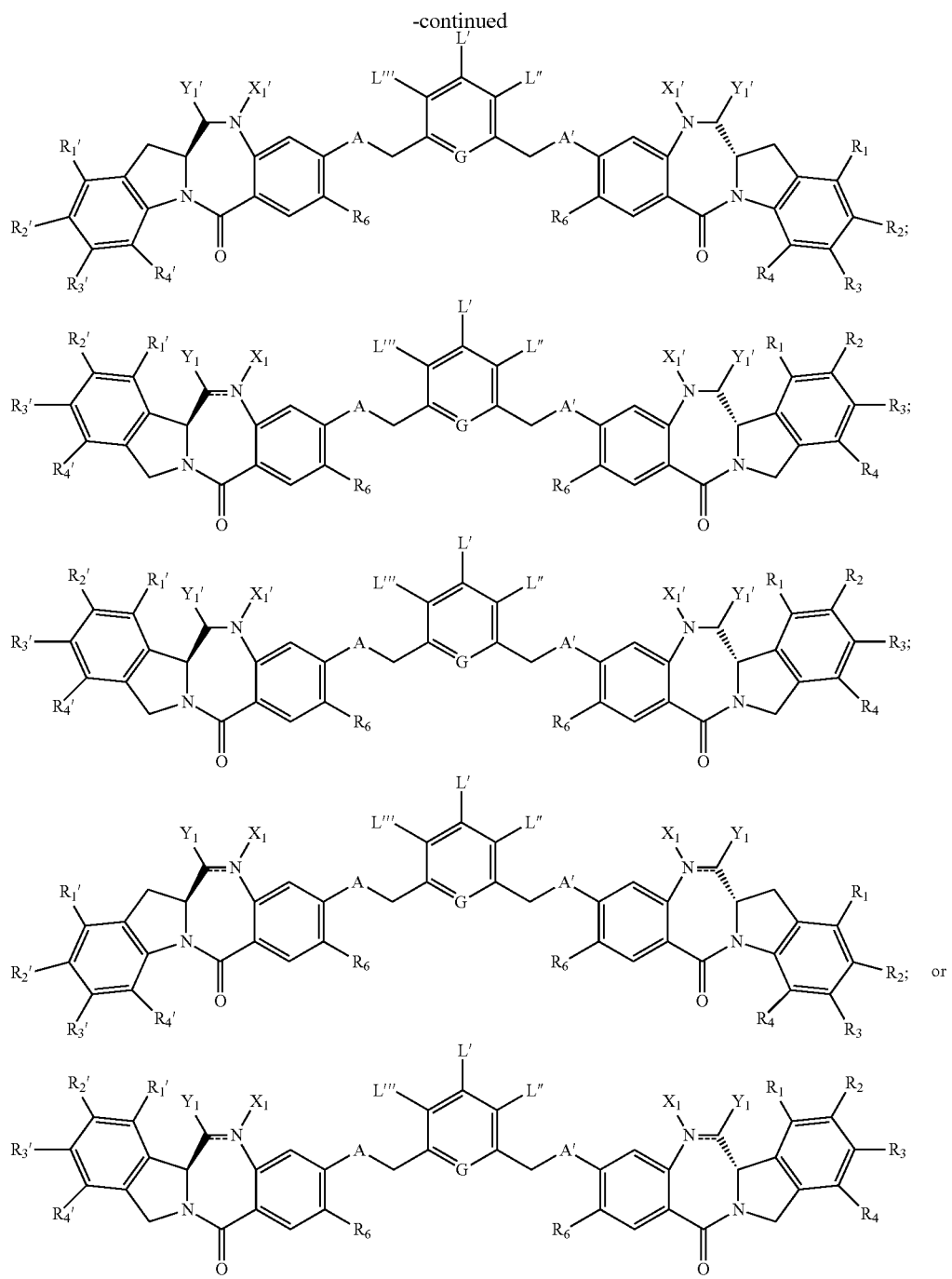

or a pharmaceutically acceptable salt thereof, wherein: one of L', L", and L''' is represented by the following formula:

$$-Z_1-P_1-Z_2-R_{x1}-C(=O)- \quad (A'), \text{ or}$$

$$-N(R^e)-R_{x1}-C(=O)- \quad (D');$$

and the other two are each independently selected from —H, an optionally substituted linear, branched or cyclic alkyl, alkenyl or alkynyl having from 1 to 10 carbon atoms, a polyethylene glycol unit —$(CH_2CH_2O)_n$—$R^c$, halogen, guanidinium [—NH(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

one of the $Z_1$ and $Z_2$ is —C(=O)—, and the other is —NR$_5$—;

$P_1$ is an amino acid residue or a peptide containing between 2 to 20 amino acid residues;

$R_{x1}$ is an optionally substituted linear, branched or cyclic alkyl, alkenyl or alkynyl having from 1 to 10 carbon atoms;

$R^e$ is —H, a linear, branched or cyclic alkyl, alkenyl or alkynyl having 1 to 10 carbon atoms or —(CH$_2$—CH$_2$—O)$_n$—$R^k$, wherein $R^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, wherein R$^{101}$ and R$^{102}$ are each independently a linear, branched, or cyclic alkyl, alkenyl or alkynyl having 1 to 10 carbon atoms;

the double line ═ between N and C represents a single bond or a double bond, provided that when it is a double bond X$_1$ is absent and Y$_1$ is —H, or a linear or branched alkyl having 1 to 4 carbon atoms, and when it is a single bond, X$_1$ is —H or an amine protecting moiety; and Y$_1$ is a leaving group selected from —OR, —OCOR', —OCOOR', —OCONR'R", —NR'R", —NR'COR", —NR'NR'R", an optionally substituted 5- or 6-membered nitrogen-containing heterocycle, a guanidinium represented by —NR'(C═NH)NR'R", an amino acid, or a peptide represented by —NRCOP', —SR, —SOR', halogen, cyano, azido, —OSO$_3$H (or a salt thereof), sulfite (—SO$_3$H or —SO$_2$H or a salt thereof), metabisulfite (H$_2$S$_2$O$_5$ or a salt thereof), mono-, di-, tri-, and tetra-thiophosphate (PO$_3$SH$_3$, PO$_2$S$_2$H$_2$, POS$_3$H$_2$, PS$_4$H$_2$ or a salt thereof), thio phosphate ester (R$^i$O)$_2$PS(OR$^i$), R'S—, R'SO, R$^i$SO$_2$, R$^i$SO$_3$, thiosulfate (HS$_2$O$_3$ or a salt thereof), dithionite (HS$_2$O$_4$ or salt thereof), phosphorodithioate (P(═S)(OR$^{k'}$)(S)(OH) or a salt thereof), hydroxamic acid (R$^{k'}$C(═O)NOH or a salt thereof), and formaldehyde sulfoxylate (HOCH$_2$SO$_2$— or a salt thereof) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

P' is an amino acid residue or a peptide containing between 2 to 20 amino acid residues, R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or an optionally substituted linear or branched alkyl having 1 to 4 carbon atoms;

n is an integer from 1 to 24;

X$_1$' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y$_1$' is selected from —H, an oxo group (i.e., Y$_1$' together with the carbon atom to which it is attached form a —C(═O)— group), an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, halogen, guanidinium [—NH(C═NH)NH$_2$], —OR, —NR'R", —NO$_2$, —NCO, —NR'COR", —SR, —SOR', —SO$_2$R', —SO$_3$—H, —OSO$_3$H, —SO$_2$NR'R", cyano, an azido, —COR', —OCOR', and —OCONR'R";

R$_6$ is —H, —R, —OR, —SR, —NR'R", —NO$_2$, or halogen;

G is —CH— or —N—;

A and A' are the same or different, and are independently selected from —O—, oxo (—C(═O)—), —CRR'O—, —CRR'—, —S—, —CRR'S—, —NR$_5$ and —CRR'N(R$_5$)—; and R$_5$ for each occurrence is independently —H or an optionally substituted linear or branched alkyl having 1 to 10 carbon atoms.

In certain embodiments, D is represented by the following structural formula:

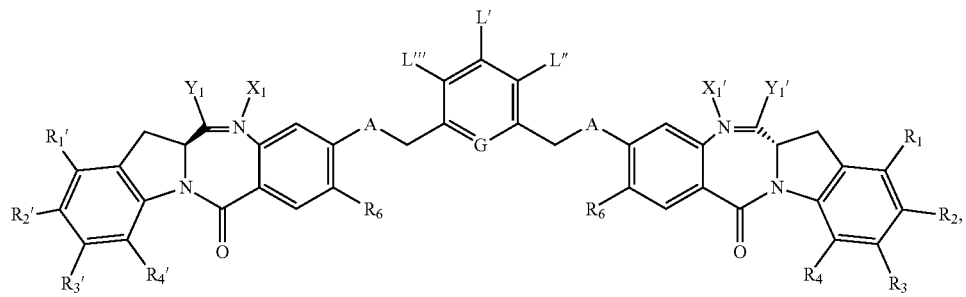

or a pharmaceutically acceptable salt thereof.

In certain embodiments, one of L', L" and L'" is represented by formula (A') or (D'), and the others are —H, an linear or branched alkyl having from 1 to 6 carbon atoms, halogen, —OH, ($C_1$-$C_6$)alkoxy, or —$NO_2$.

In certain embodiments, L' is represented by formula (A'); and L" and L'" are both —H.

In certain embodiments, L' is represented by formula (D'); and L" and L'" are both —H.

In certain embodiments, $R_{x1}$ is a linear, branched or cyclic alkyl having 1 to 6 carbon atoms optionally substituted with halogen, —OH, —$SO_3H$, ($C_1$-$C_3$)alkyl, ($C_1$-$C_3$)alkoxy, halo ($C_1$-$C_3$)alkyl, or a charged substituent or an ionizable group Q.

In certain embodiments, L' is represented by the following formula:

—$NR_5$—$P_1$—C(=O)—($CR_aR_b$)$_s$—C(=O)— (B1');

—$NR_5$—$P_1$—C(=O-Cy-($CR_aR_b$)$_{s1'}$—C(=O)— (B2');

—C(=O)—$P_1$—$NR_5$—($CR_aR_b$)$_s$—C(=O)— (C1'), or

—C(=O)—$P_1$—$NR_5$-Cy-($CR_aR_b$)$_{s1'}$—C(=O)— (C2')

wherein:
$R_a$ and $R_b$, for each occurrence, are each independently —H, ($C_1$-$C_3$)alkyl or a charged substituent or an ionizable group Q;
s is an integer from 1 to 6;
s1' is 0 or an integer from 1 to 6; and
Cy is a cyclic alkyl having 5 or 6 ring carbon atoms optionally substituted with halogen, —OH, ($C_1$-$C_3$) alkyl, ($C_1$-$C_3$)alkoxy, or halo($C_1$-$C_3$)alkyl.

In certain embodiments, $R_a$ and $R_b$ are both H; Cy in formulas (B2') and (C2') is cyclohexane; and $R_5$ is H or Me.

In certain embodiments, s1' is 0 or 1.

In certain embodiments, the charged substituent or an ionizable group Q is i) —$SO_3H$, —Z'—$SO_3H$, —$OPO_3H_2$, —Z'—$OPO_3H_2$, —$PO_3H_2$, —Z'—$PO_3H_2$, —$CO_2H$, —Z'—$CO_2H$, —$NR_{11}R_{12}$, or —Z'—$NR_{11}R_{12}$, or a pharmaceutically acceptable salt thereof; or, ii) —$N^+R_{14}R_{15}R_{16}X^-$ or —Z'—$N^+R_{14}R_{15}R_{16}X^-$; Z' is an optionally substituted alkylene, an optionally substituted cycloalkylene or an optionally substituted phenylene; $R_{14}$ to $R_{16}$ are each independently an optionally substituted alkyl; and $X^-$ is a pharmaceutically acceptable anion.

In certain embodiments, Q is —$SO_3H$ or a pharmaceutically acceptable salt thereof.

In certain embodiments, $P_1$ is a peptide containing 2 to 10 amino acid residues. For example, $P_1$ may be a peptide containing 2 to 5 amino acid residues, such as Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu, β-Ala-Leu-Ala-Leu, Gly-Phe-Leu-Gly, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, or Met-Ala. In certain embodiments, $P_1$ is Gly-Gly-Gly, Ala-Val, Ala-Ala, Ala-D-Ala, D-Ala-Ala, or D-Ala-D-Ala.

In certain embodiments, the double line == between N and C represents a double bond.

In certain embodiments, the double line == between N and C represents a single bond, $X_1$ is —H or an amine protecting group; and $Y_1$ is selected from —OR, —OCOR', —SR, —NR'R," an optionally substituted 5- or 6-membered nitrogen-containing heterocycle, —$SO_3M$, —$SO_2M$ and —$OSO_3M$, wherein M is $H^+$ or a pharmaceutically acceptable cation.

In certain embodiments, $Y_1$ is selected from —$SO_3M$, —OH, —OMe, —OEt or —NHOH.

In certain embodiments, $Y_1$ is —$SO_3M$ or —OH, wherein M is $H^+$, $Na^+$ or $K^+$.

In certain embodiments, $X_1'$ is selected from the group consisting of —H, —OH, an optionally substituted linear, branched or cyclic alkyl, alkenyl or alkynyl having from 1 to 10 carbon atoms, and phenyl.

In certain embodiments, $X_1'$ is —H, —OH, ($C_1$-$C_3$)alkyl, halo($C_1$-$C_3$)alkyl, or phenyl.

Preferably, $X_1'$ is —H, —OH or -Me. In certain embodiments, $X_1'$ is —H.

In certain embodiments, $Y_1'$ is selected from the group consisting of —H, an oxo group, an optionally substituted linear, branched or cyclic alkyl, alkenyl or alkynyl having from 1 to 10 carbon atoms. In certain embodiments, $Y_1'$ is —H, an oxo group, ($C_1$-$C_3$)alkyl or halo($C_1$—$C_3$)alkyl. In certain embodiments, $Y_1'$ is —H or oxo. In certain embodiments, $Y_1'$ is —H.

In certain embodiments, A and A' are the same or different, and are selected from —O—, —S—, —$NR_5$—, and oxo —(C=O)—. In certain embodiments, A and A' are the same or different, and are selected from —O— and —S—. In certain embodiments, A and A' are —O—.

In certain embodiments, $R_6$ is —OMe.

In certain embodiments, $R_1$, $R_2$, $R_3$, $R_4$, $R_1'$, $R_2'$, $R_3'$ and $R_4'$ are independently —H, halogen, —$NO_2$, —OH, ($C_1$-$C_3$)alkyl, halo($C_1$-$C_3$)alkyl or ($C_1$-$C_3$)alkoxy. In certain embodiments, $R_1$, $R_2$, $R_3$, $R_4$, $R_1'$, $R_2'$, $R_3'$ and $R_4'$ are all —H.

In certain embodiments, R, R', R" and $R_5$ are each independently —H or ($C_1$-$C_3$)alkyl.

In certain embodiments:
the double line == between N and C represents a single bond or double bond, provided that when it is a double bond, $X_1$ is absent and $Y_1$ is —H; and when it is a single bond, $X_1$ is —H, and $Y_1$ is —OH or —$SO_3M$;
$R_1$, $R_2$, $R_3$, $R_4$, $R_1'$, $R_2'$, $R_3'$ and $R_4'$ are all —H;
$R_6$ is —OMe;
$X_1'$ and $Y_1'$ are both —H;
A and A' are —O—; and
M is $H^+$, $Na^+$ or $K^+$.

In certain embodiments, D is represented by the following structural formula:

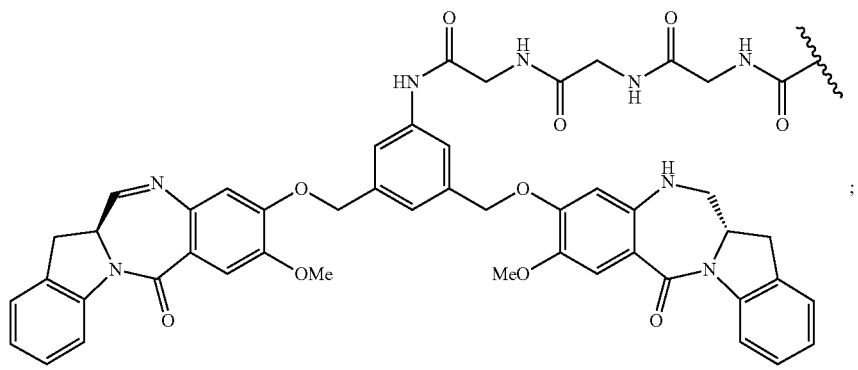
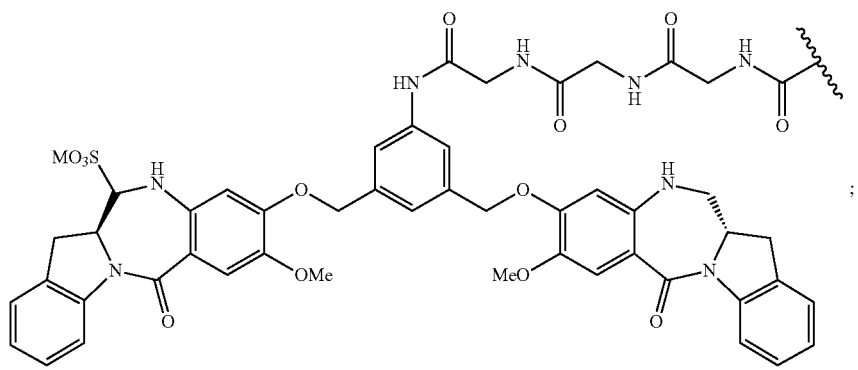
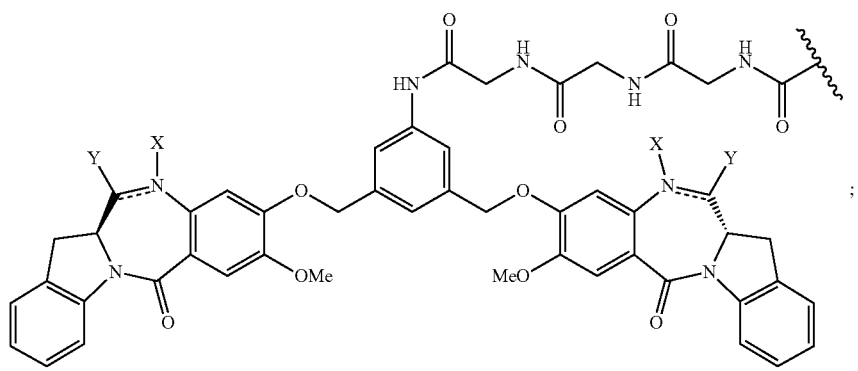
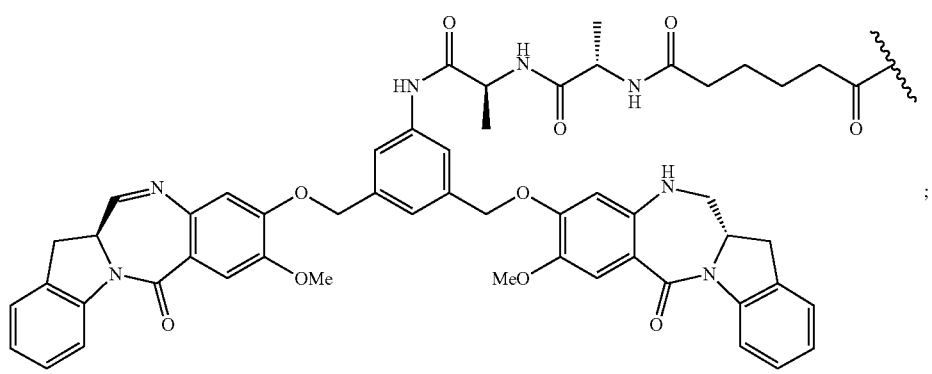

-continued
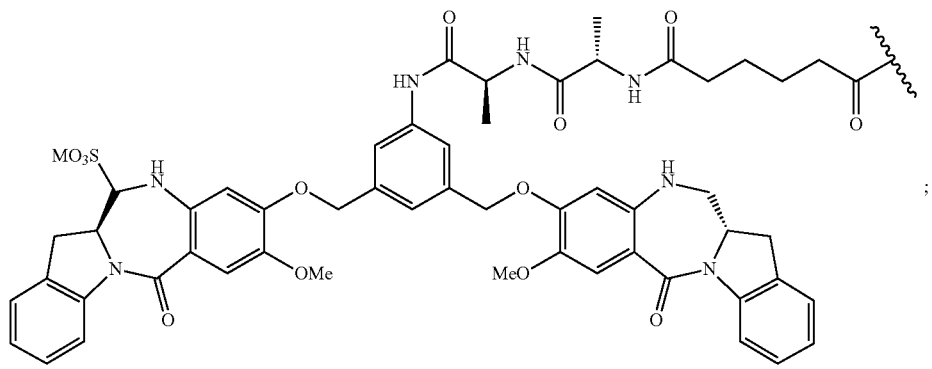
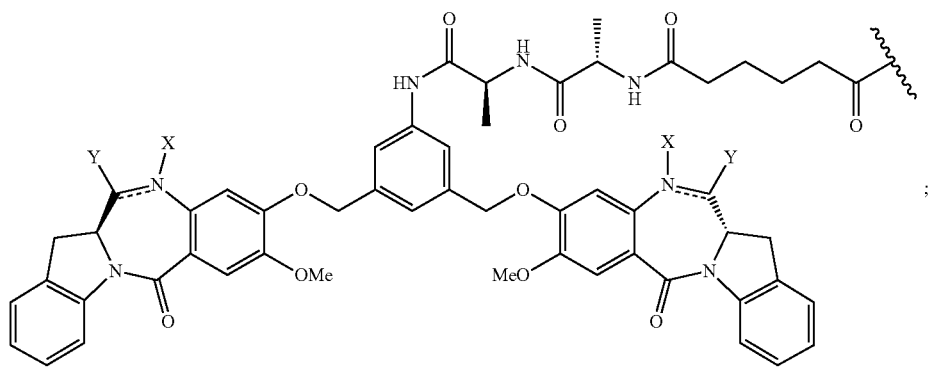
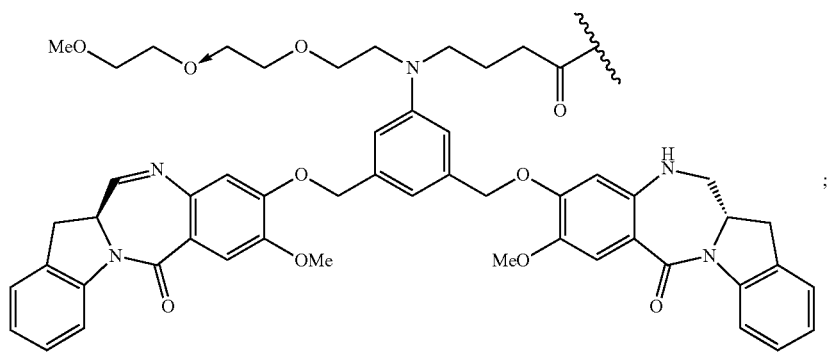
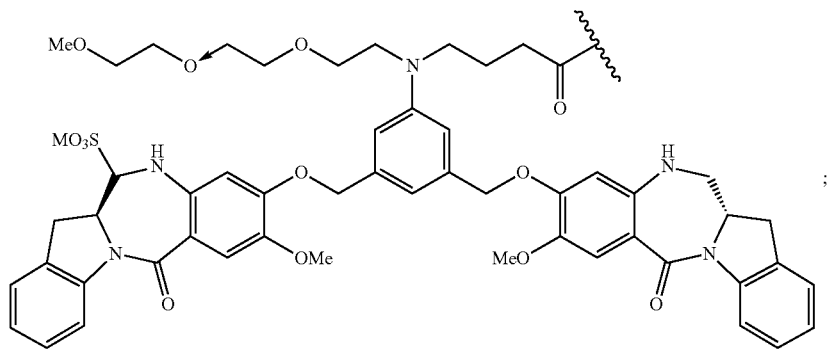

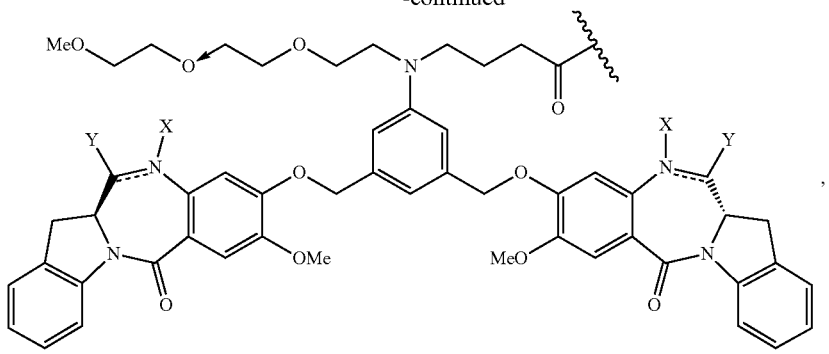

wherein the double line ═ between N and C represents a single bond or a double bond, provided that when it is a double bond, X is absent and Y is —H, and when it is a single bond, X is —H, and Y is —SO₃M; and M is H⁺ or a pharmaceutically acceptable cation; M is H⁺ or a pharmaceutically acceptable cation.

In certain embodiments, the conjugate is represented by the following structural formula:

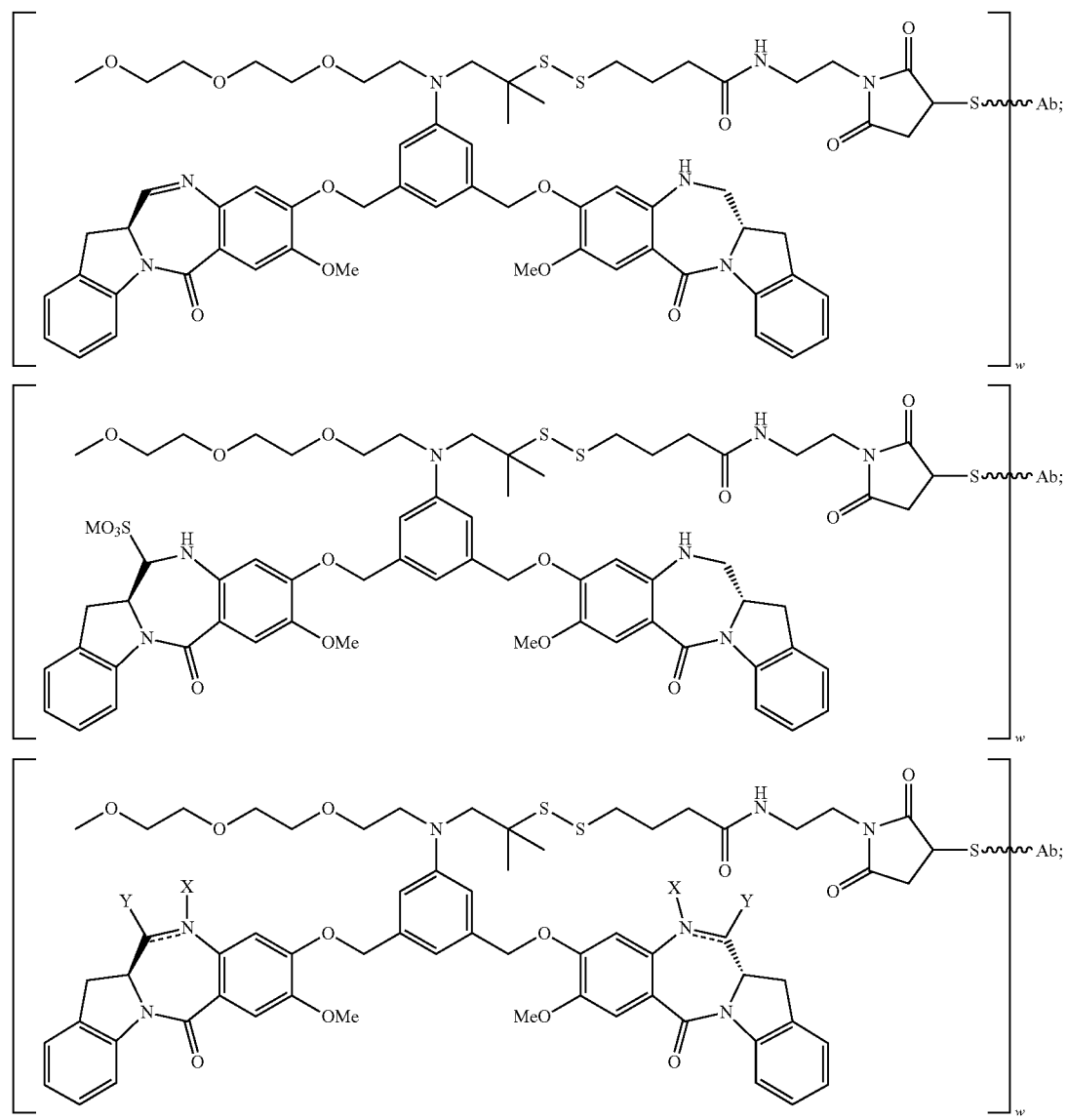

-continued
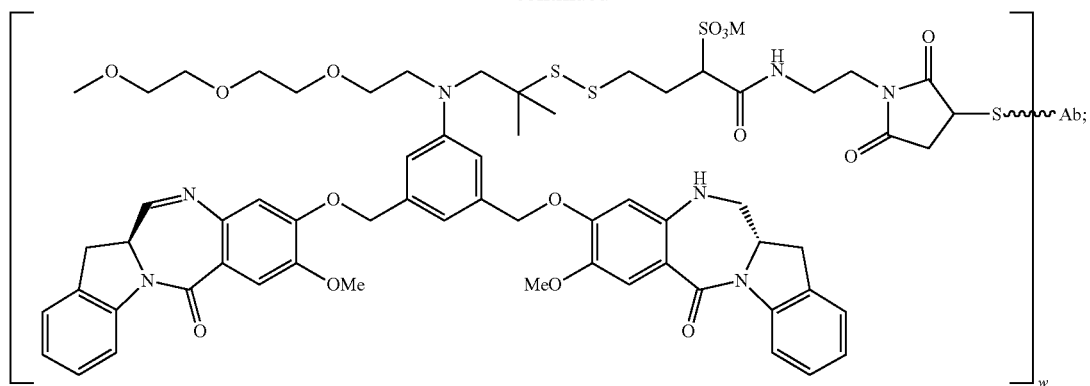
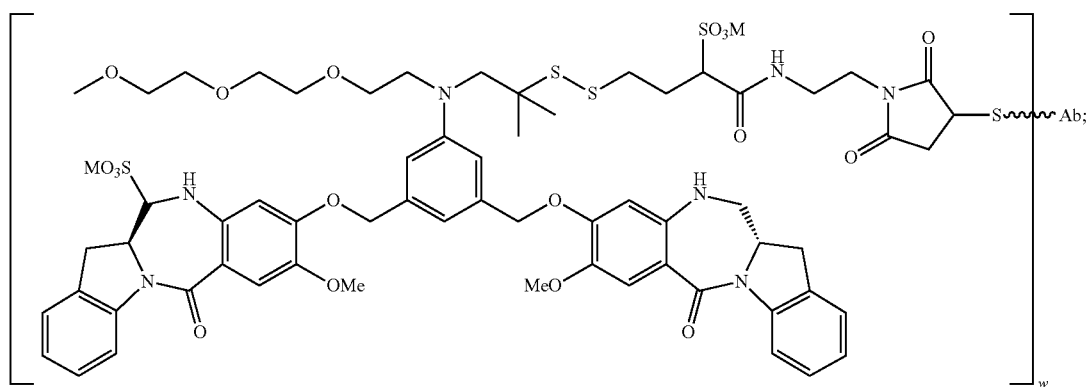
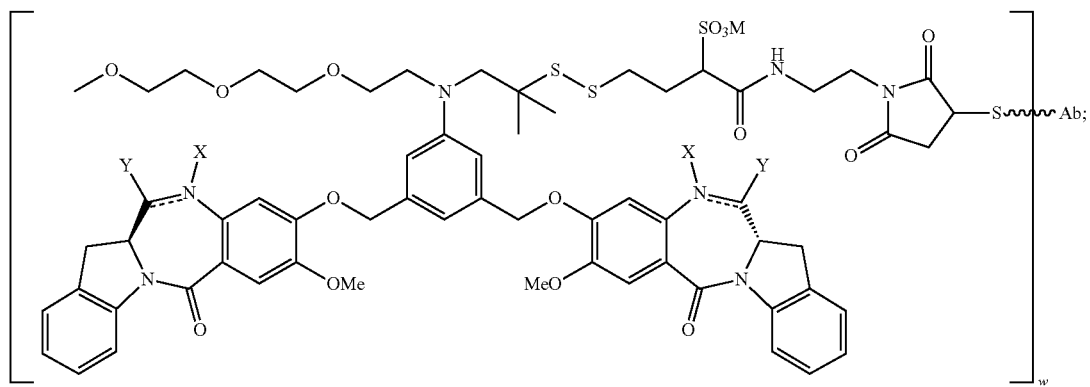
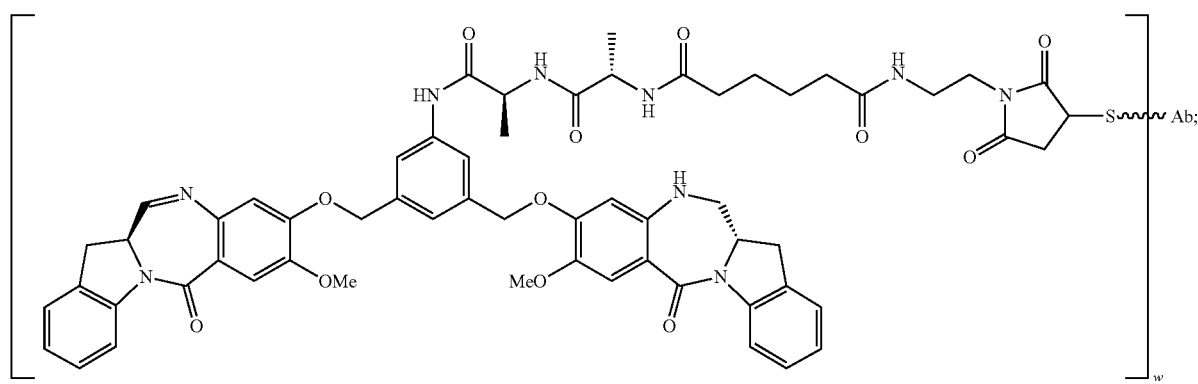

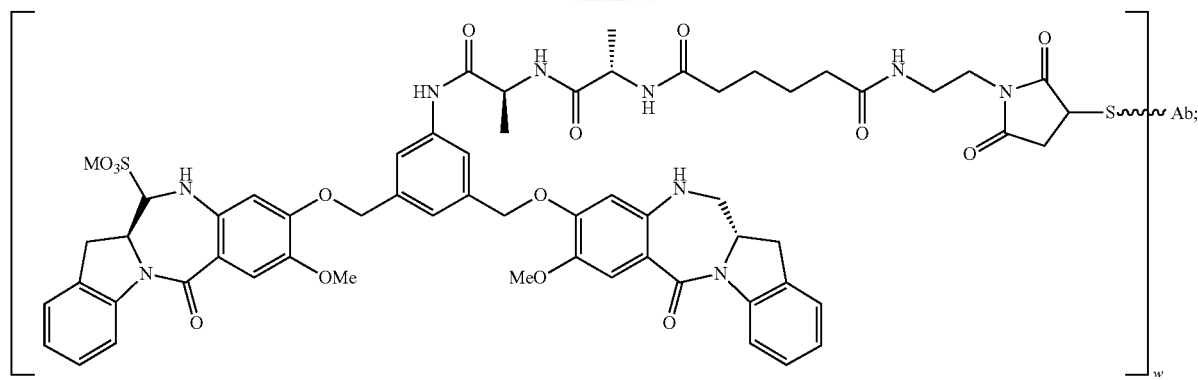
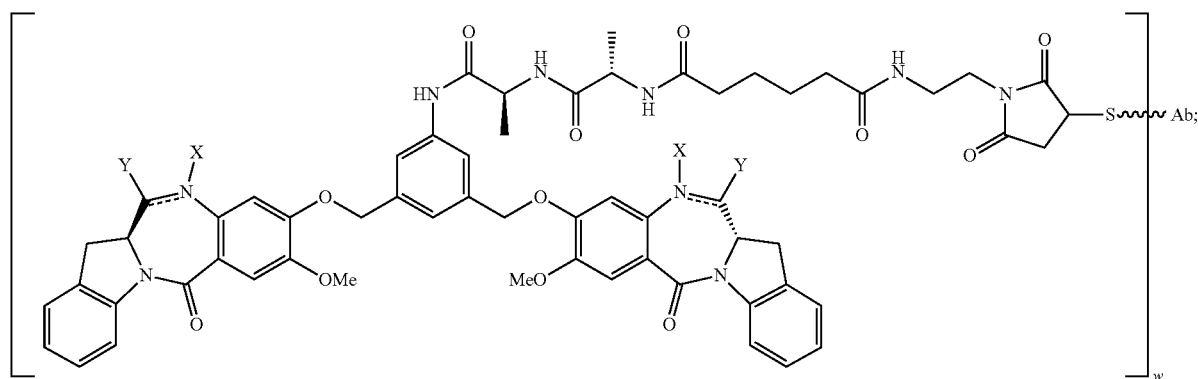
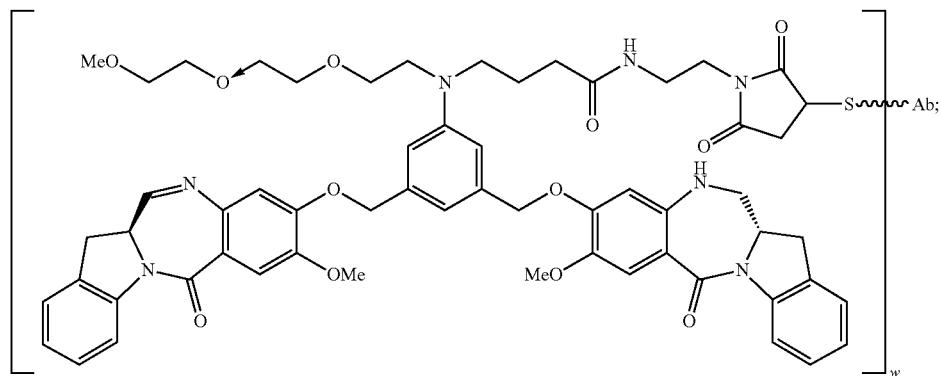
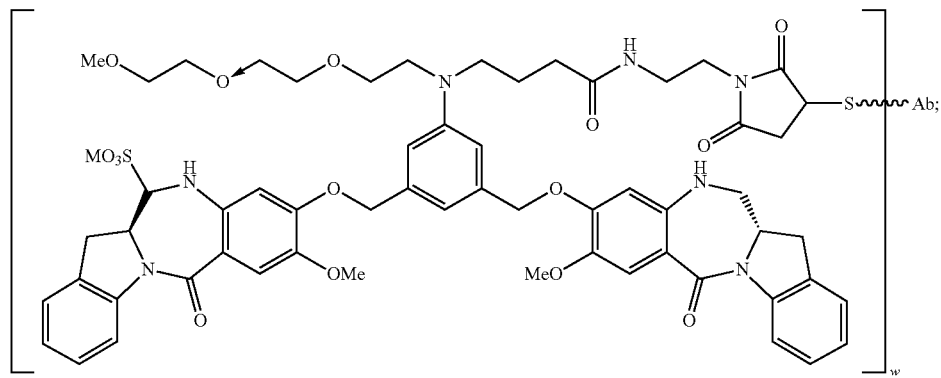

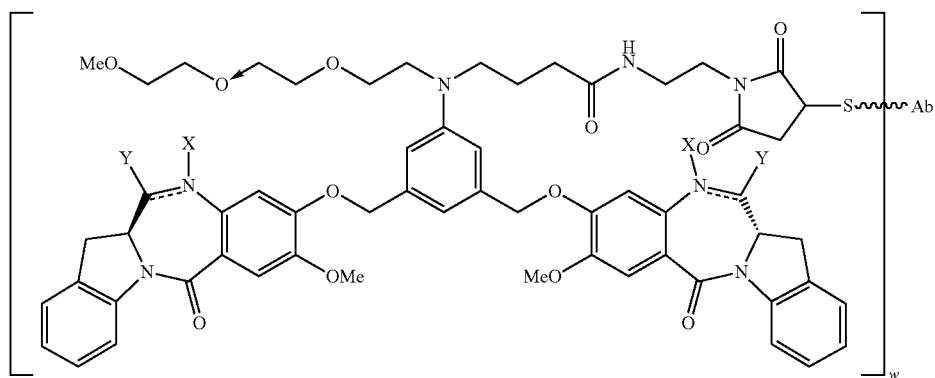
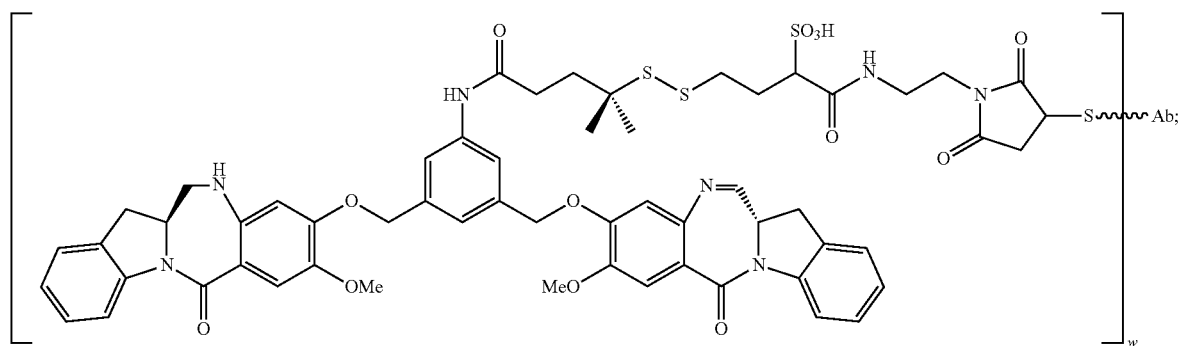
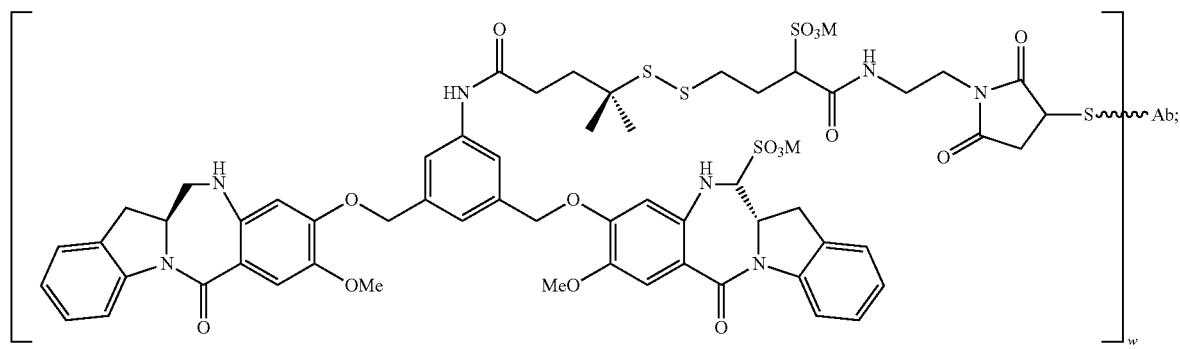
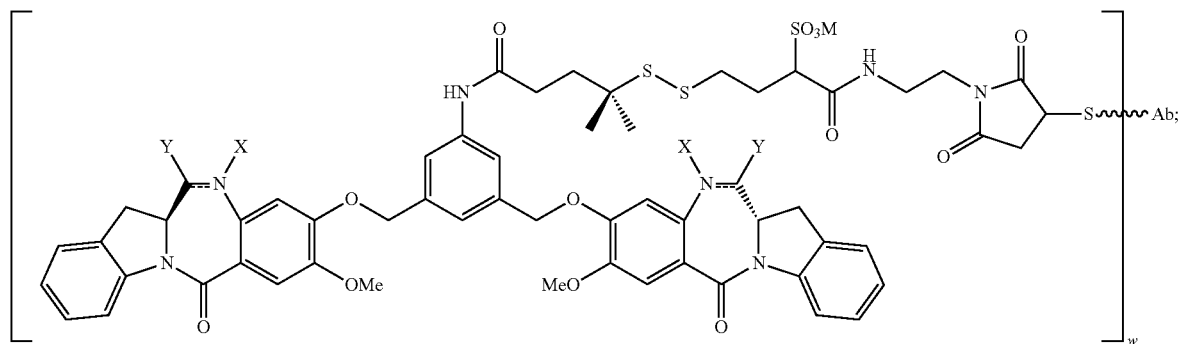

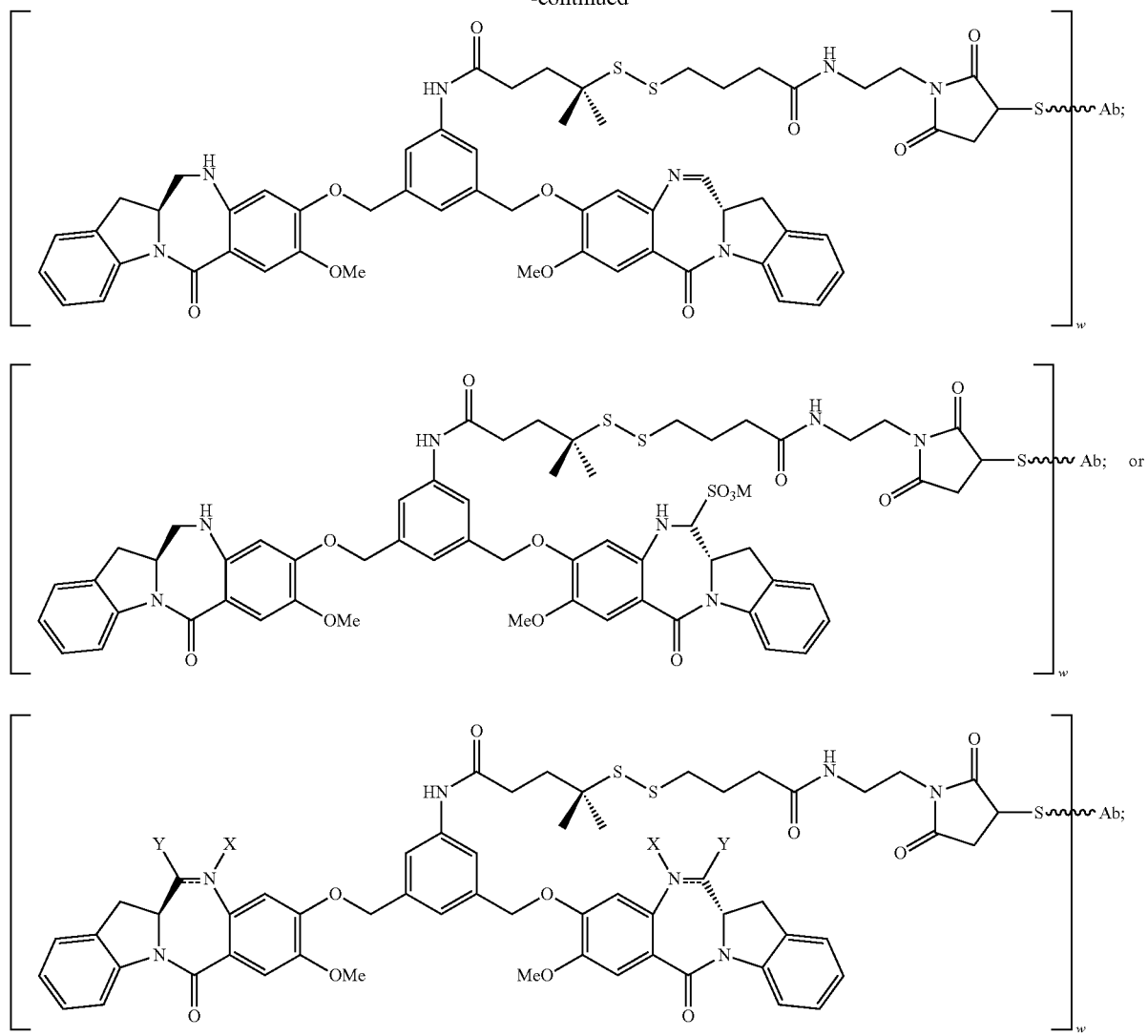

or a pharmaceutically acceptable salt thereof, wherein the double line ═ between N and C represents a single bond or a double bond, provided that when it is a double bond, X is absent and Y is —H, and when it is a single bond, X is —H, and Y is —SO₃M; and M is H⁺ or a pharmaceutically acceptable cation.

In certain embodiments, M, when present, is H⁺, Na⁺ or K⁺.

Another aspect of the invention provides a compound represented by the following structural formula:

D-L-J$_{CB}$, or a pharmaceutically acceptable salt thereof, wherein:
D is represented by the following structural formula:

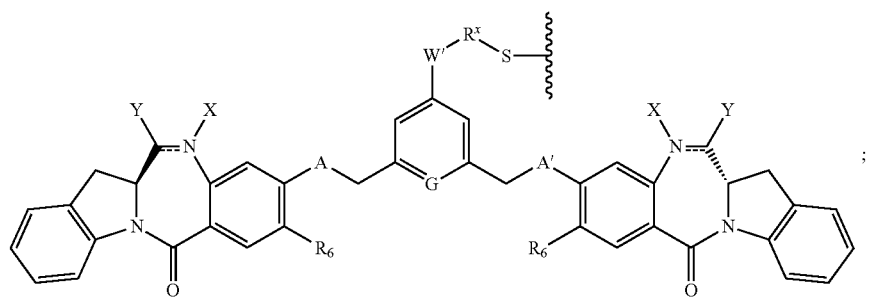

-continued

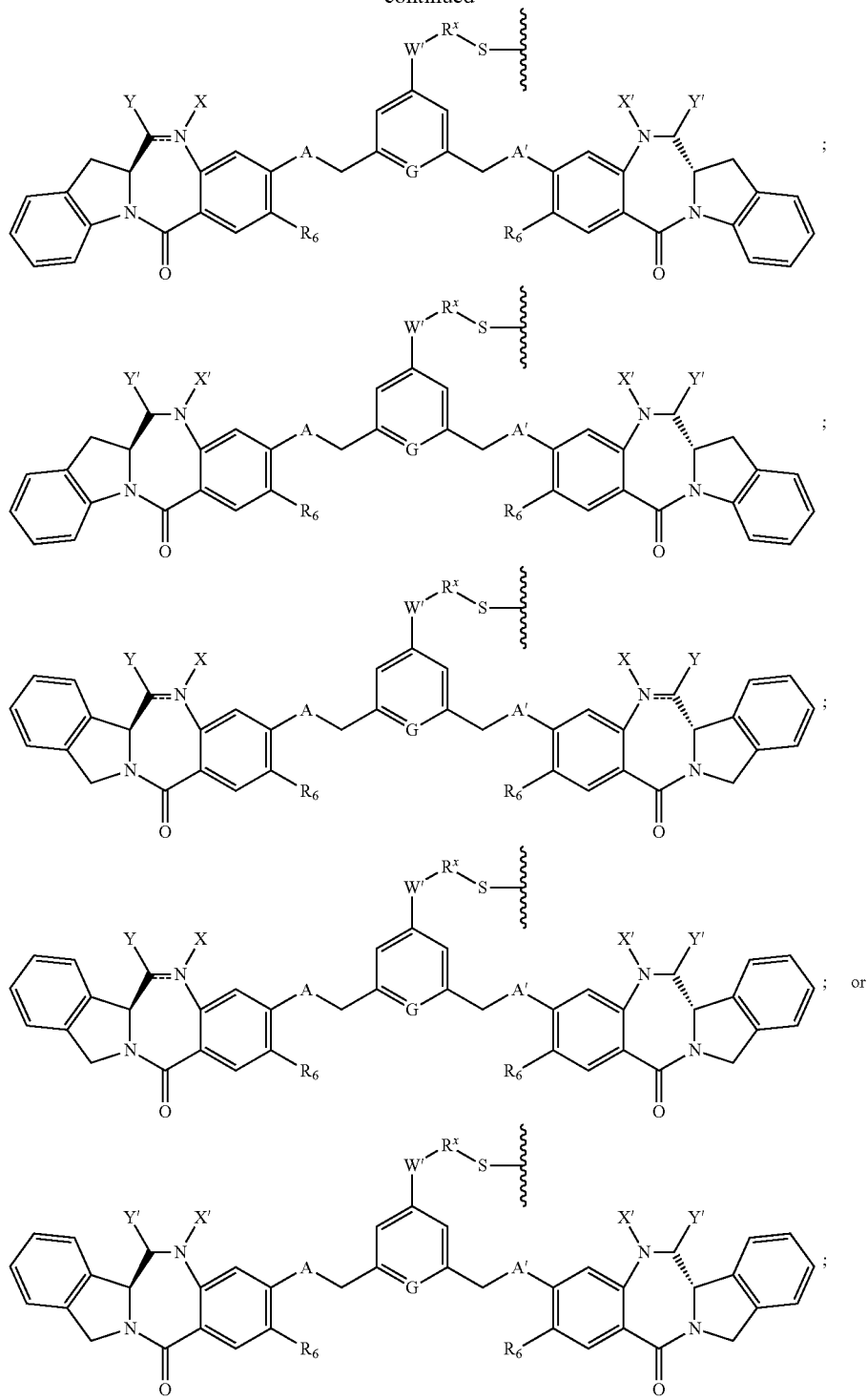

or pharmaceutically acceptable salt thereof, wherein:

the double line ═ between N and C represents a single bond or a double bond, provided that when it is a double bond, X is absent and Y is —H, and when it is a single bond, X is selected from —H, or an amine protecting group; and Y is selected from —OR, —OCOR', —SR, —NR'R", —SO$_3$M, —SO$_2$M or —OSO$_3$M, wherein M is —H or a cation;

R is —H, an optionally substituted linear, branched or cyclic alkyl, alkenyl or alkynyl having from 1 to 10 carbon atoms or a PEG group —(CH$_2$CH$_2$O)$_n$—R$^c$, wherein n is an integer from 1 to 24, and R$^c$ is a linear or branched alkyl having 1 to 4 carbon atoms;

R' and R" are each independently selected from —H, —OH, —OR, —NRR', —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—R$^c$, and R$^{g'}$ is —H, an optionally substituted linear, branched or cyclic alkyl, alkenyl or alkynyl having from 1 to 10 carbon atoms or a PEG group —(CH$_2$CH$_2$O)$_n$—R;

X' is selected from the group consisting of —H, —OH, a substituted or unsubstituted linear, branched or cyclic alkyl, alkenyl or alkynyl having from 1 to 10 carbon atoms, phenyl, and an amine-protecting group;

Y' is selected from the group consisting of —H, an oxo group, a substituted or unsubstituted linear, branched or cyclic alkyl, alkenyl or alkynyl having from 1 to 10 carbon atoms;

A and A' are selected from —O— and —S—;

W' is absent, or selected from —O—, —N(R$^e$)—, —N(R$^e$)—C(=O)—, —N(C(=O)R$^e$)—, —S— or —CH$_2$—S—, —CH$_2$NR$^e$—;

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{11}$R$^{102}$) group or a 5- or 6-membered nitrogen containing heterocycle, wherein R$^{101}$ and R$^{102}$ are each independently a linear, branched, or cyclic alkyl, alkenyl or alkynyl having 1 to 10 carbon atoms;

G is selected from —CH— or —N—;

R$_6$ is —H, —R, —OR, —SR, —NR'R", —NO$_2$, or halogen;

-L- is represented by the following structural formula:

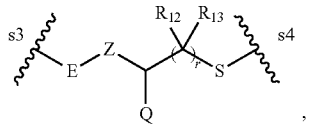

wherein:
s3 is the site covalently linked to J$_{CB}$, and s4 is the site covalently linked to D;

E is —(CR$_{10}$R$_{11}$)$_q$—, cycloalkyl or cycloalkylalkyl;

Z is absent, —SO$_2$NR$_9$—, —NR$_9$SO$_2$—, —C(=O)NR$_9$—, —NR$_9$—C(=O)—, —C(=O)—O—, —O—C(=O)—, —C(=O)—NR$_9$—(CH$_2$CH$_2$O)—, —NR$_9$—C(=O)—(CH$_2$CH$_2$O)—, —(OCH$_2$CH$_2$)$_p$—C(=O)NR$_9$—, or —(OCH$_2$CH$_2$)$_p$—NR$_9$—C(=O)—;

p is an integer from 1 to 1000;

Q is H, a charged substituent or an ionizable group;

R$_9$, R$_{10}$, R$_{11}$, R$_{12}$, and R$_{13}$, for each occurrence, are independently H or an optionally substituted alkyl;

q and r, for each occurrence, are independently an integer between 0 and 10; and J$_{CB}$ is

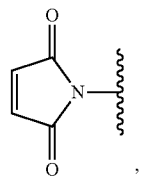 [SMILES: *N1C(=O)C=CC1=O]

X'—CR$^b$R$^c$—C(=O)—, X'—CR$^b$R$^c$—C(=O)—NR$^e$

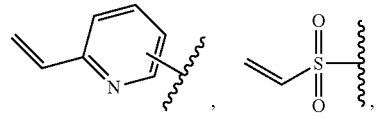

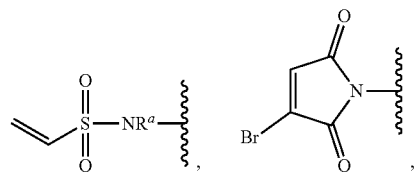

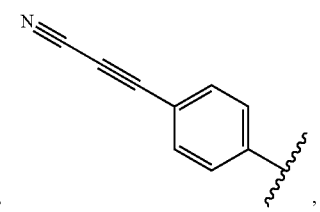

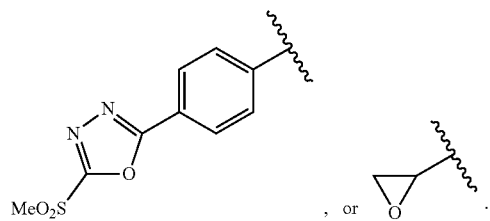

In certain embodiments, D is represented by the following structural formula:

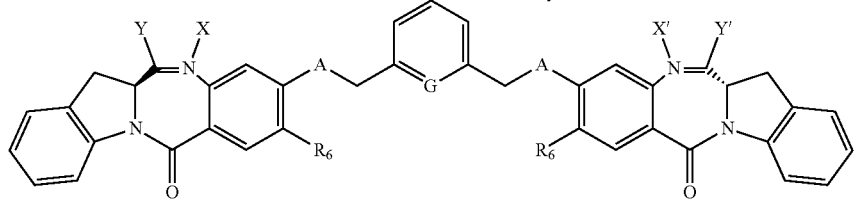

or a pharmaceutically acceptable salt thereof.

In certain embodiments, $R^a$, $R^b$, $R^c$, and $R^e$ are each H.

In certain embodiments, $J_{CB}$ is

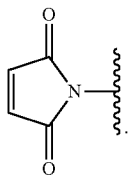

In certain embodiments:

the double line == between N and C represents a single bond or a double bond, provided that when it is a double bond X is absent and Y is —H, and when it is a single bond, X is —H; Y is —OH or —SO$_3$M;

M is —H or a pharmaceutically acceptable cation (e.g., Na$^+$);

X' and Y' are both —H;

A and A' are both —O—;

$R_6$ is —OMe; and $R^x$ is a linear or branched alkyl having 1 to 6 carbon atoms.

In certain embodiments, D is represented by the following structural formula:

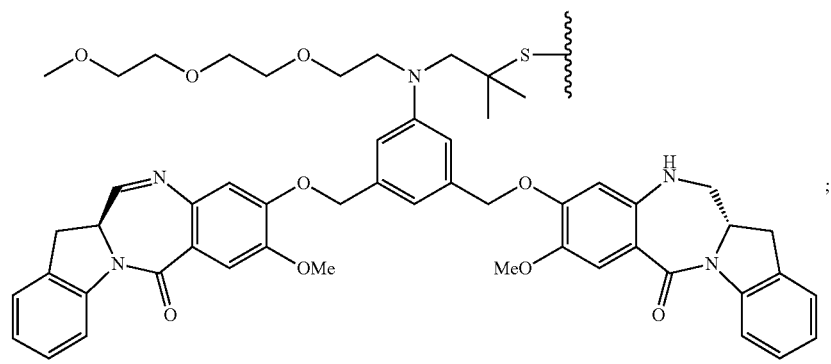

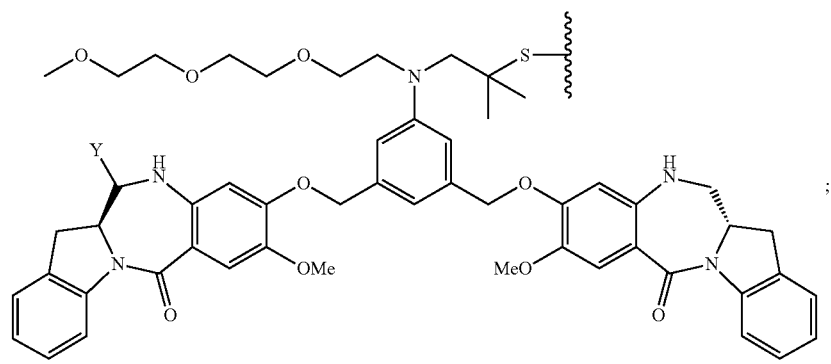

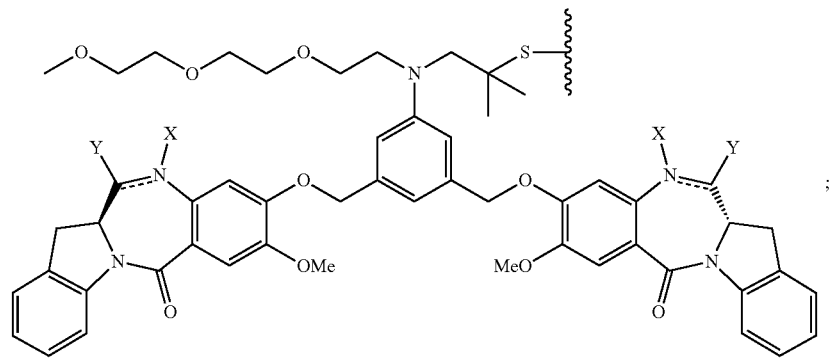

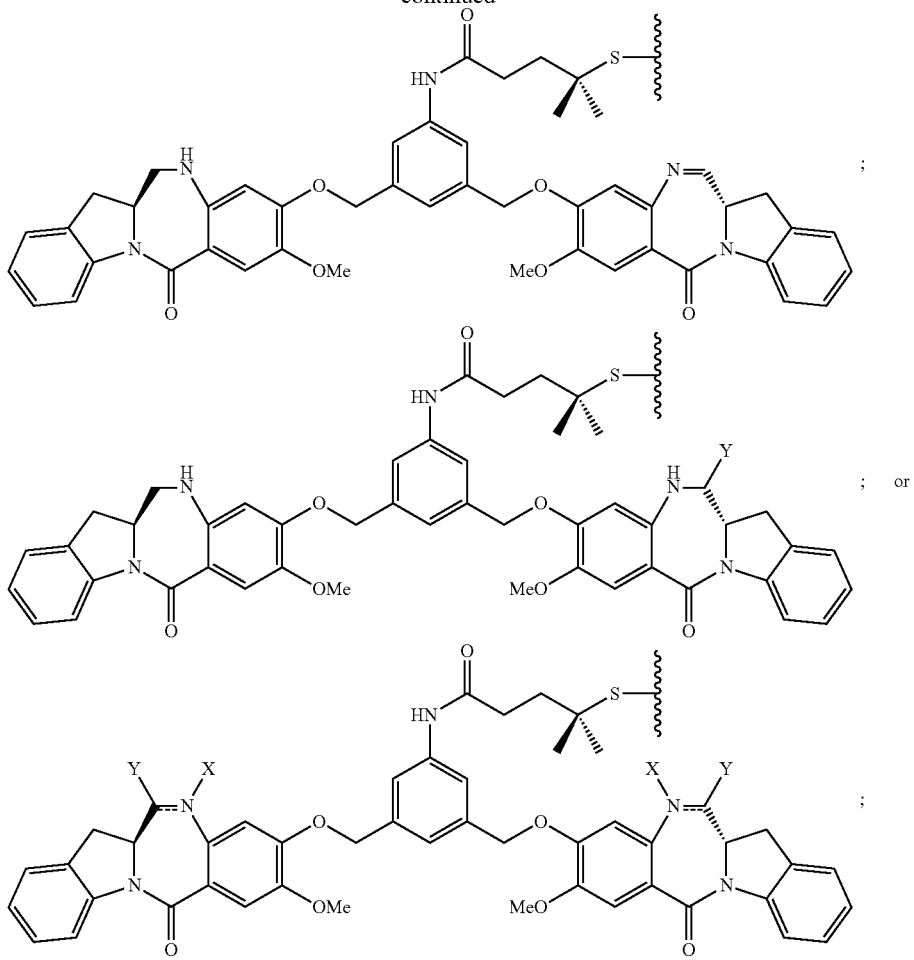

or a pharmaceutically acceptable salt thereof.

In certain embodiments, Y is —SO$_3$M; and M is H$^+$, Na$^{z+}$ or K$^+$.

In certain embodiments, E is —(CR$_{10}$R$_{11}$)$_q$—.

In certain embodiments, E is

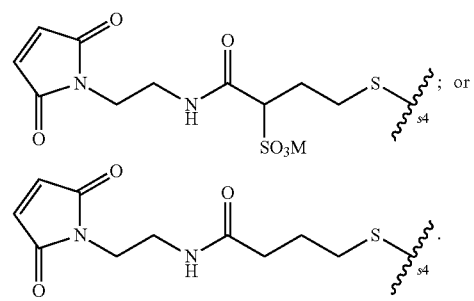

In certain embodiments, Z is —C(=O)—NR$_9$— or —NR$_9$—C(=O)—. In certain embodiments, R$_9$ is —H.

In certain embodiments, Q is:
i) H;
ii) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{14}$R$_{15}$, or a pharmaceutically acceptable salt thereof; or,
iii) —N$^+$R$_{14}$R$_{15}$R$_{16}$X$^-$ or —Z'—N$^+$R$_{14}$R$_{15}$R$_{16}$X$^-$;

Z' is an optionally substituted alkylene, an optionally substituted cycloalkylene, or an optionally substituted phenylene;

R$_{14}$, R$_{15}$ and R$_{16}$ are each independently an optionally substituted alkyl; and, X$^-$ is a pharmaceutically acceptable anion.

In certain embodiments, Z' is an optionally substituted alkylene.

In certain embodiments, Q is H, or —SO$_3$M, wherein M is H$^+$, Na$^+$ or K$^+$.

In certain embodiments, R$_9$, R$_{10}$, R$_{11}$, R$_{12}$, and R$_{13}$ are all H; and q and r are each independently an integer between 1 and 6.

In certain embodiments, -L-J$_{CB}$ is represented by the following structural formula:

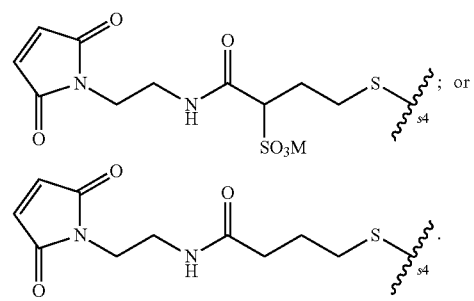

wherein M is H$^+$ or a pharmaceutically acceptable cation.

In certain embodiments, the compound is represented by the following structural formula:

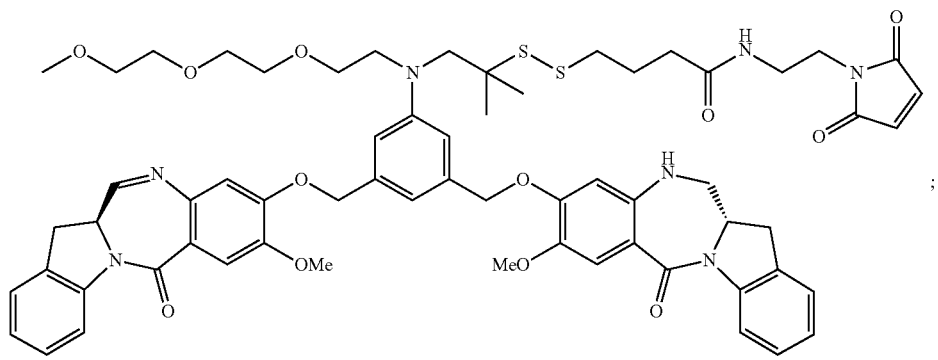
;
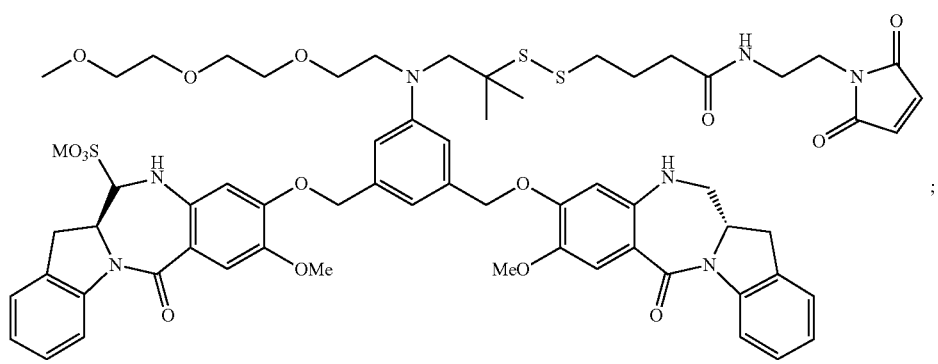
;
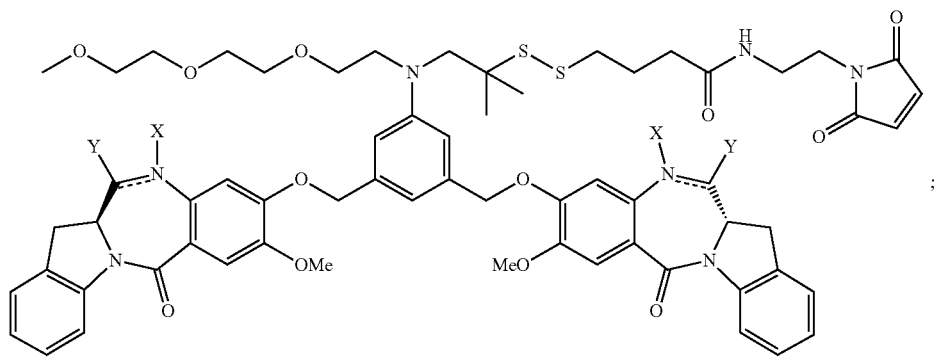
;
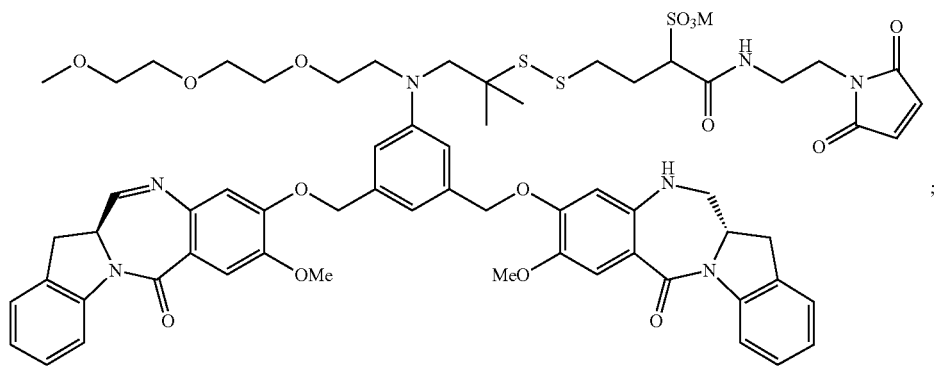
;

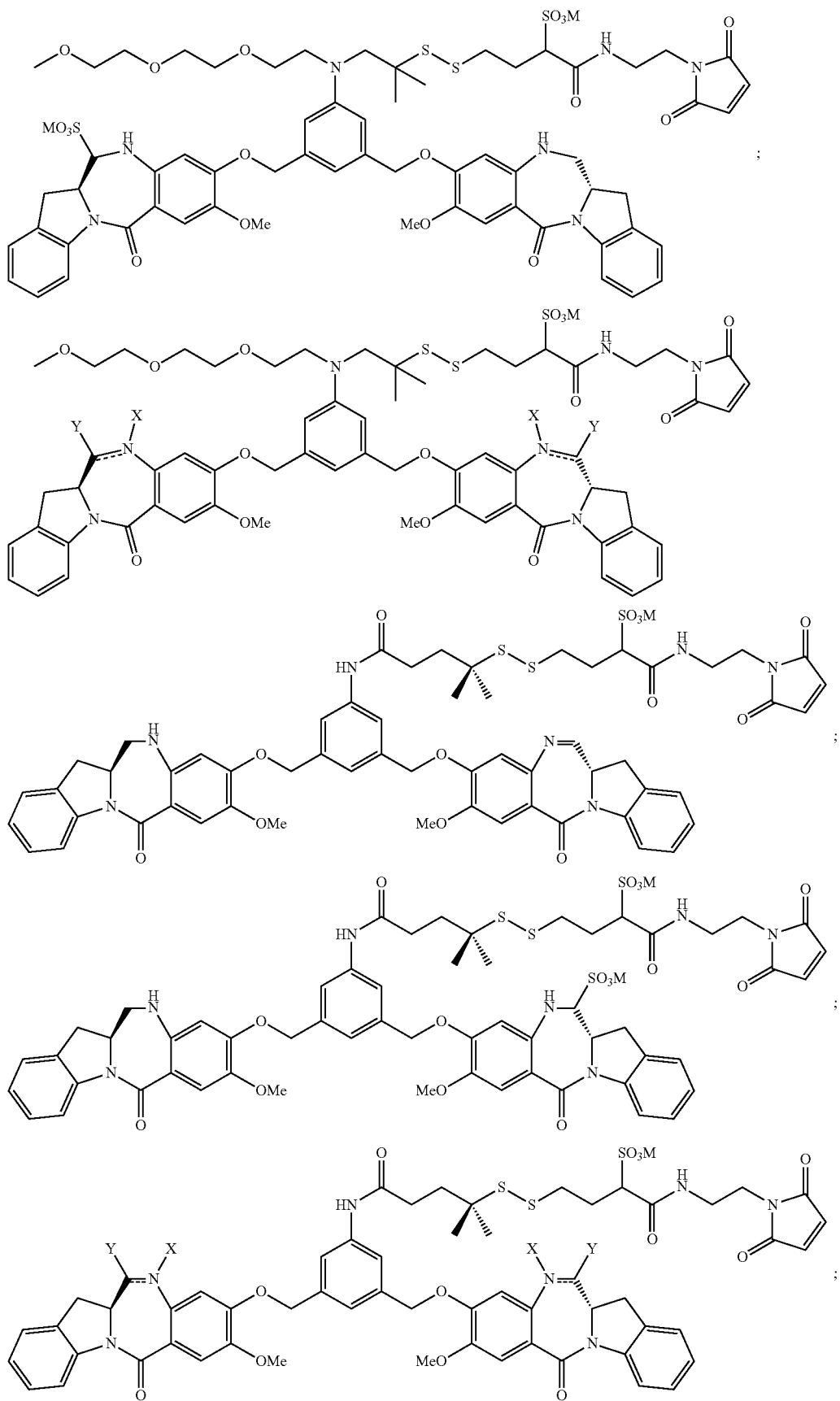

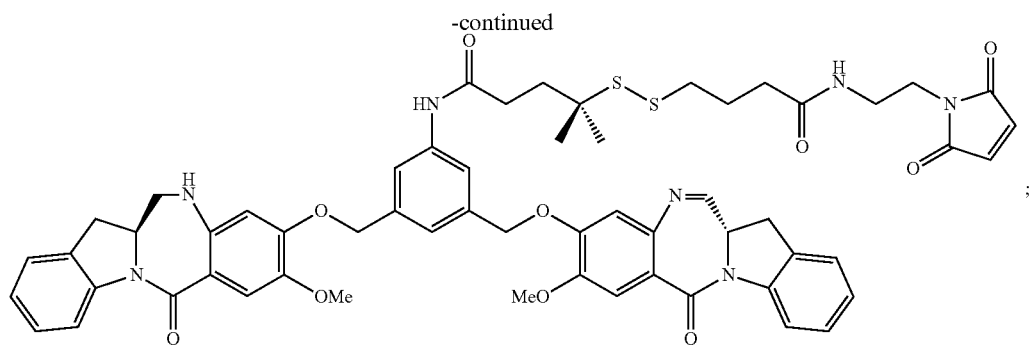

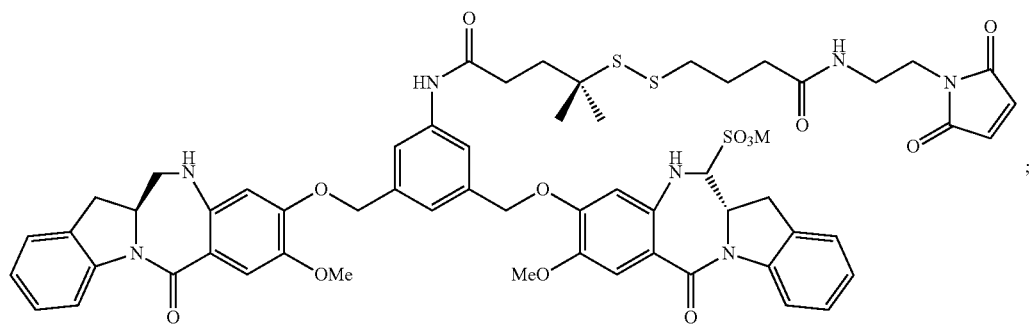

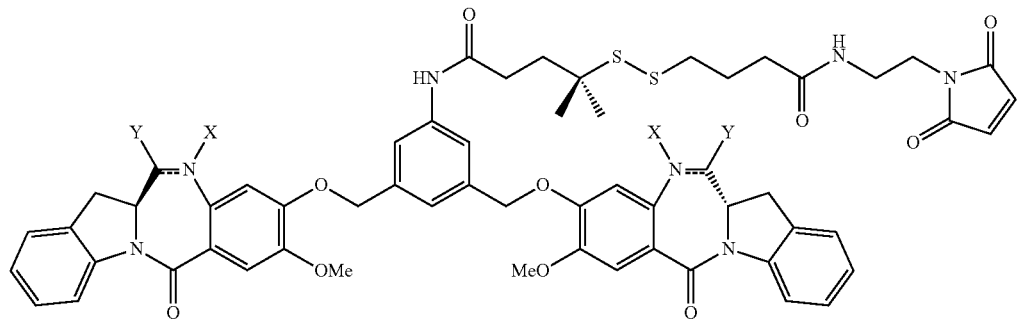

or a pharmaceutically acceptable salt thereof, wherein the double line == between N and C represents a single bond or a double bond, provided that when it is a double bond, X is absent and Y is —H, and when it is a single bond, X is —H, and Y is —SO$_3$M; and M is H$^+$ or a pharmaceutically acceptable cation.

Another aspect of the invention provides a compound represented by the following structural formula:

D-L-J$_{CB}$, or a pharmaceutically acceptable salt thereof, wherein:
D is represented by the following structural formula:

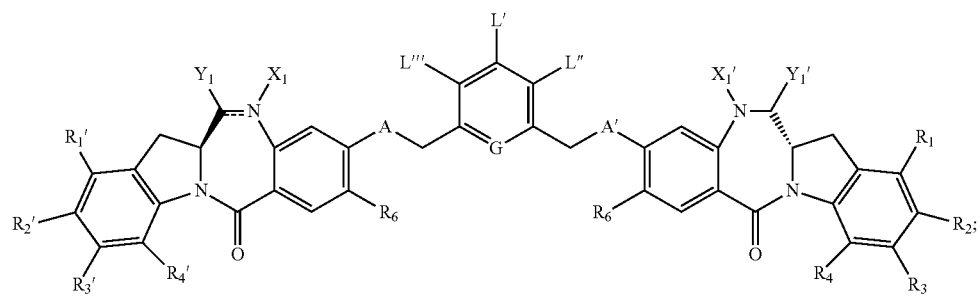

-continued

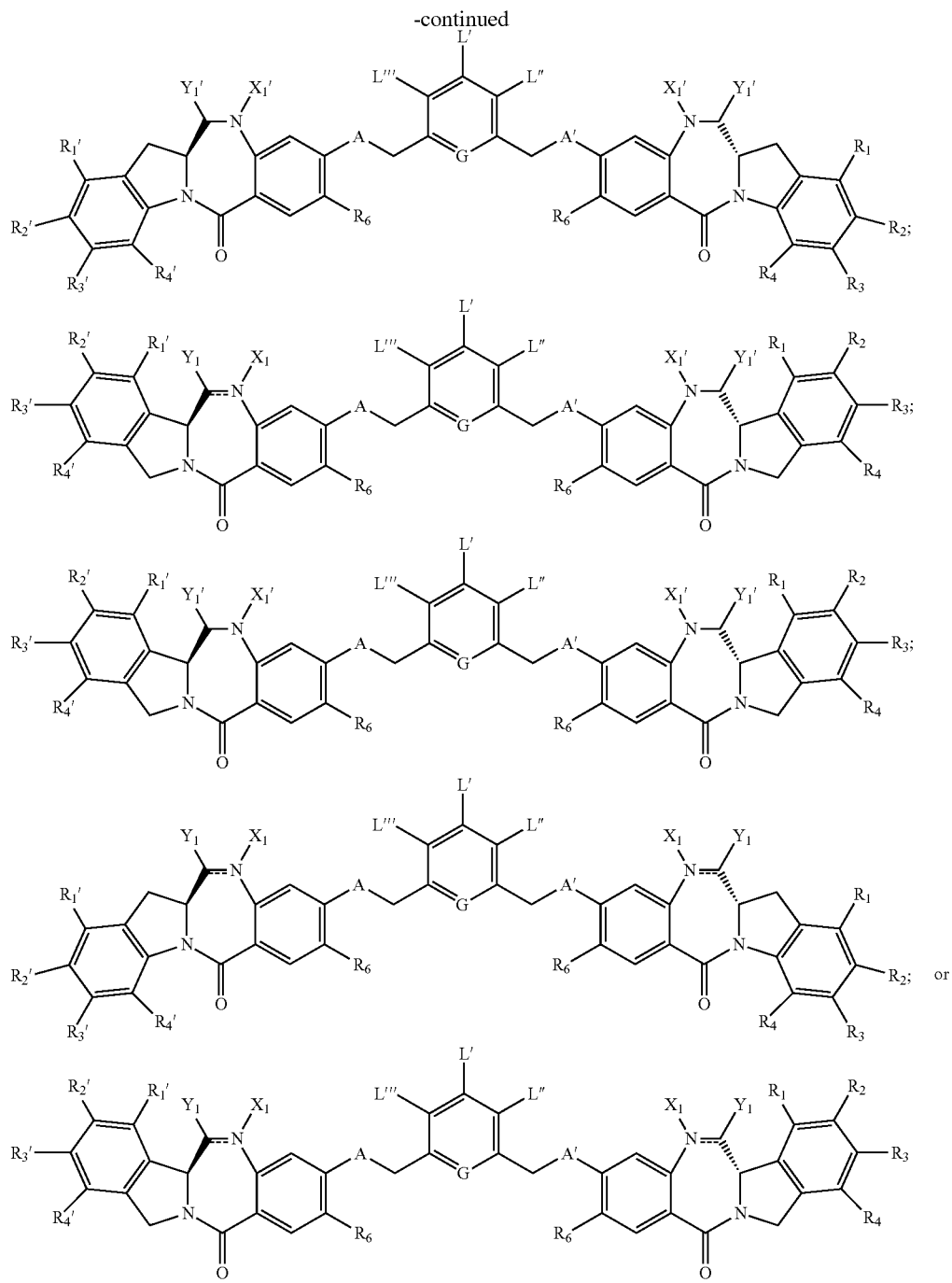

or a pharmaceutically acceptable salt thereof, wherein:
one of L', L", and L'" is represented by the following formula:

$$-Z_1-P_1-Z_2-R_{x1}-C(=O)- \quad (A'), \text{ or}$$

$$-N(R^e)-R_{x1}-C(=O)- \quad (D');$$

and the other two are each independently selected from —H, an optionally substituted linear, branched or cyclic alkyl, alkenyl or alkynyl having from 1 to 10 carbon atoms, a polyethylene glycol unit $-(CH_2CH_2O)_n-R^c$, halogen, guanidinium [—NH(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

one of the $Z_1$ and $Z_2$ is —C(=O)—, and the other is —NR$_5$—; $P_1$ is an amino acid residue or a peptide containing between 2 to 20 amino acid residues;

$R_{x1}$ is an optionally substituted linear, branched or cyclic alkyl, alkenyl or alkynyl having from 1 to 10 carbon atoms;

$R^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, wherein R$^{101}$ and R$^{102}$ are each independently a linear, branched, or cyclic alkyl, alkenyl or alkynyl having 1 to 10 carbon atoms;

the double line == between N and C represents a single bond or a double bond, provided that when it is a double bond X$_1$ is absent and Y$_1$ is —H, or a linear or branched alkyl having 1 to 4 carbon atoms, and when it is a single bond, X$_1$ is —H or an amine protecting moiety; and Y$_1$ is a leaving group selected from —OR, —OCOR', —OCOOR', —OCONR'R'', —NR'R'', —NR'COR'', —NR'NR'R'', an optionally substituted 5- or 6-membered nitrogen-containing heterocycle, a guanidinium represented by —NR'(C=NH)NR'R'', an amino acid, or a peptide represented by —NRCOP', —SR, —SOR', halogen, cyano, azido, —OSO$_3$H (or a salt thereof), sulfite (—SO$_3$H or —SO$_2$H or a salt thereof), metabisulfite (H$_2$S$_2$O$_5$ or a salt thereof), mono-, di-, tri-, and tetra-thiophosphate (PO$_3$SH$_3$, PO$_2$S$_2$H$_2$, POS$_3$H$_2$, PS$_4$H$_2$ or a salt thereof), thio phosphate ester (R$^i$O)$_2$PS(OR$^i$), R'S—, R'SO, R'SO$_2$, R$^i$SO$_3$, thiosulfate (HS$_2$O$_3$ or a salt thereof), dithionite (HS$_2$O$_4$ or salt thereof), phosphorodithioate (P(=S)(OR$^{k'}$)(S)(OH) or a salt thereof), hydroxamic acid (R$^{k'}$C(=O)NOH or a salt thereof), and formaldehyde sulfoxylate (HOCH$_2$SO$_2$— or a salt thereof) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

P' is an amino acid residue or a peptide containing between 2 to 20 amino acid residues, R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R'' are each independently selected from —H, —OH, —OR, —NHR, —NR$_2$, —COR, an optionally substituted linear, branched or cyclic alkyl, alkenyl or alkynyl having 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or an optionally substituted linear or branched alkyl having 1 to 4 carbon atoms;

n is an integer from 1 to 24;

X$_1$' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y$_1$' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, halogen, guanidinium [—NH(C=NH)NH$_2$], —OR, —NR'R'', —NO$_2$, —NCO, —NR'COR'', —SR, —SOR', —SO$_2$R', —SO$_3$—H, —OSO$_3$H, —SO$_2$NR'R'', cyano, an azido, —COR', —OCOR', and —OCONR'R'';

R$_6$ is —H, —R, —OR, —SR, —NR'R'', —NO$_2$, or halogen;

G is —CH— or —N—;

A and A' are the same or different, and are independently selected from —O—, oxo (—C(=O)—), —CRR'O—, —CRR'—, —S—, —CRR'S—, —NR$_5$ and —CRR'N(R$_5$)—; and R$_5$ for each occurrence is independently —H or an optionally substituted linear or branched alkyl having 1 to 10 carbon atoms;

-L- is represented by the following structural formula:

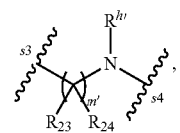

wherein:

s3 is the site covalently linked to J$_{CB}$', and s4 is the site covalently linked to D;

R$_{23}$ and R$_{24}$, for each occurrence, are independently H or an optionally substituted alkyl;

m' is an integer between 0 and 10;

R$^{h'}$ is H or an optionally substituted alkyl; and

J$_{CB}$ is

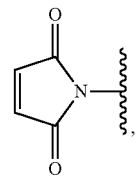 [SMILES: *N1C(=O)C=CC1=O]

X'—CR$^b$R$^c$—C(=O)—, X'—CR$^b$R$^c$—C(=O)—NR$^e$—,

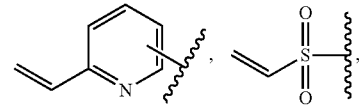

-continued

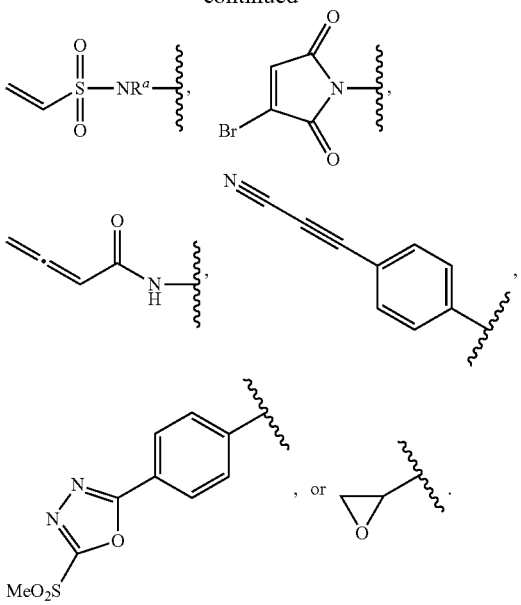

In certain embodiments, D is represented by the following structural formula:

$$-NR_5-P_1-C(=O)-(CR_aR_b)_s-C(=O)- \qquad (B1');$$

$$-NR_5-P_1-C(=O)-Cy-(CR_aR_b)_{s1'}-C(=O)- \qquad (B2');$$

$$-C(=O)-P_1-NR_5-(CR_aR_b)_s-C(=O)- \qquad (C1'), \text{ or}$$

$$-C(=O)-P_1-NR_5-Cy-(CR_aR_b)_{s1'}-C(=O)- \qquad (C2')$$

wherein:
$R_a$ and $R_b$, for each occurrence, are each independently —H, $(C_1-C_3)$alkyl or a charged substituent or an ionizable group Q;
s is an integer from 1 to 6;
s1' is 0 or an integer from 1 to 6; and
Cy is a cyclic alkyl having 5 or 6 ring carbon atoms optionally substituted with halogen, —OH, $(C_1-C_3)$alkyl, $(C_1-C_3)$alkoxy, or halo$(C_1-C_3)$alkyl.

In certain embodiments, $R_a$ and $R_b$ are both H; Cy for formulas (B2') and (C2') is cyclohexane; and $R_5$ is H or Me.

In certain embodiments, s1' is 0 or 1.

In certain embodiments, the charged substituent or an ionizable group Q is i) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a pharmaceutically acceptable salt thereof; or, ii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an

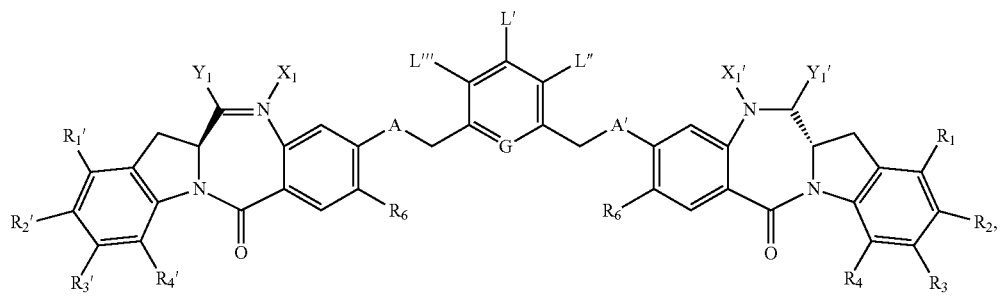

or a pharmaceutically acceptable salt thereof.

In certain embodiments, $R^a$, $R^b$, $R^c$, and $R^e$ are each H.

In certain embodiments, $J_{CB}$ is

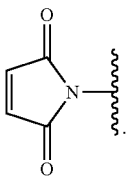

In certain embodiments, one of L', L" and L'" is represented by formula (A') or (D'), and the others are —H, an linear or branched alkyl having from 1 to 6 carbon atoms, halogen, —OH, $(C_1-C_6)$alkoxy, or —NO$_2$.

In certain embodiments, L' is represented by formula (A'); and L" and L'" are both —H.

In certain embodiments, L' is represented by formula (D'); and L" and L'" are both —H.

In certain embodiments, $R_{x1}$ is a linear, branched or cyclic alkyl having 1 to 6 carbon atoms optionally substituted with halogen, —OH, —SO$_3$H, $(C_1-C_3)$alkyl, $(C_1-C_3)$alkoxy, halo $(C_1-C_3)$alkyl, or a charged substituent or an ionizable group Q.

In certain embodiments, L' is represented by the following formula:

optionally substituted phenylene; $R_{14}$ to $R_{16}$ are each independently an optionally substituted alkyl; and X$^-$ is a pharmaceutically acceptable anion.

In certain embodiments, Q is SO$_3$H or a pharmaceutically acceptable salt thereof.

In certain embodiments, $P_1$ is a peptide containing 2 to 10 amino acid residues. For example, $P_1$ may be a peptide containing 2 to 5 amino acid residues, such as Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 14), 3-Ala-Leu-Ala-Leu (SEQ ID NO: 15), Gly-Phe-Leu-Gly (SEQ ID NO: 16), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In certain embodiments, $P_1$ is Gly-Gly-Gly, Ala-Val, Ala-Ala, Ala-D-Ala, D-Ala-Ala, and D-Ala-D-Ala.

In certain embodiments, the double line $=\!=$ between N and C represents a double bond.

In certain embodiments, the double line $=\!=$ between N and C represents a single bond, $X_1$ is —H or an amine protecting group; and $Y_1$ is selected from —OR, —OCOR', —SR, —NR'R," an optionally substituted 5- or 6-membered nitrogen-containing heterocycle, —SO$_3$M, —SO$_2$M and —OSO$_3$M, wherein M is H$^+$ or a pharmaceutically acceptable cation. In certain embodiments, Y$_1$ is selected from —SO$_3$M, —OH, —OMe, —OEt or —NHOH. In certain embodiments, Y$_1$ is —SO$_3$M or —OH, and M is H$^+$, Na$^+$ or K$^+$.

In certain embodiments, X$_1$' is selected from the group consisting of —H, —OH, an optionally substituted linear, branched or cyclic alkyl, alkenyl or alkynyl having from 1 to 10 carbon atoms, and phenyl. In certain embodiments, X$_1$' is —H, —OH, (C$_1$-C$_3$)alkyl, halo(C$_1$-C$_3$)alkyl, or phenyl. In certain embodiments, X$_1$' is —H, —OH or -Me. In certain embodiments, X$_1$' is —H.

In certain embodiments, Y$_1$' is selected from the group consisting of —H, an oxo group, an optionally substituted linear, branched or cyclic alkyl, alkenyl or alkynyl having from 1 to 10 carbon atoms. In certain embodiments, Y$_1$' is —H, an oxo group, (C$_1$-C$_3$)alkyl or halo(C$_1$-C$_3$)alkyl. In certain embodiments, Y$_1$' is —H or oxo. In certain embodiments, Y$_1$' is —H.

In certain embodiments, A and A' are the same or different, and are selected from —O—, —S—, —NR$_5$—, and oxo —(C═O)—. In certain embodiments, A and A' are the same or different, and are selected from —O— and —S—. In certain embodiments, A and A' are —O—.

In certain embodiments, R$_6$ is —OMe.

In certain embodiments, R$_1$, R$_2$, R$_3$, R$_4$, R$_1$', R$_2$', R$_3$' and R$_4$' are independently —H, halogen, —NO$_2$, —OH, (C$_1$-C$_3$)alkyl, halo(C$_1$-C$_3$)alkyl or (C$_1$-C$_3$)alkoxy. In certain embodiments, R$_1$, R$_2$, R$_3$, R$_4$, R$_1$', R$_2$', R$_3$' and R$_4$' are all —H.

In certain embodiments, R, R', R" and R$_5$ are each independently —H or (C$_1$-C$_3$)alkyl.

In certain embodiments:
the double line ═ between N and C represents a single bond or double bond, provided that when it is a double bond X$_1$ is absent and Y$_1$ is —H, and when it is a single bond, X$_1$ is —H, Y is —OH or —SO$_3$M; R$_1$, R$_2$, R$_3$, R$_4$, R$_1$', R$_2$', R$_3$' and R$_4$' are all —H;
R$_6$ is —OMe;
X$_1$' and Y$_1$' are both —H;
A and A' are —O—; and
M is H$^+$, Na$^+$ or K$^+$.

In certain embodiments, D is represented by the following structural formula:

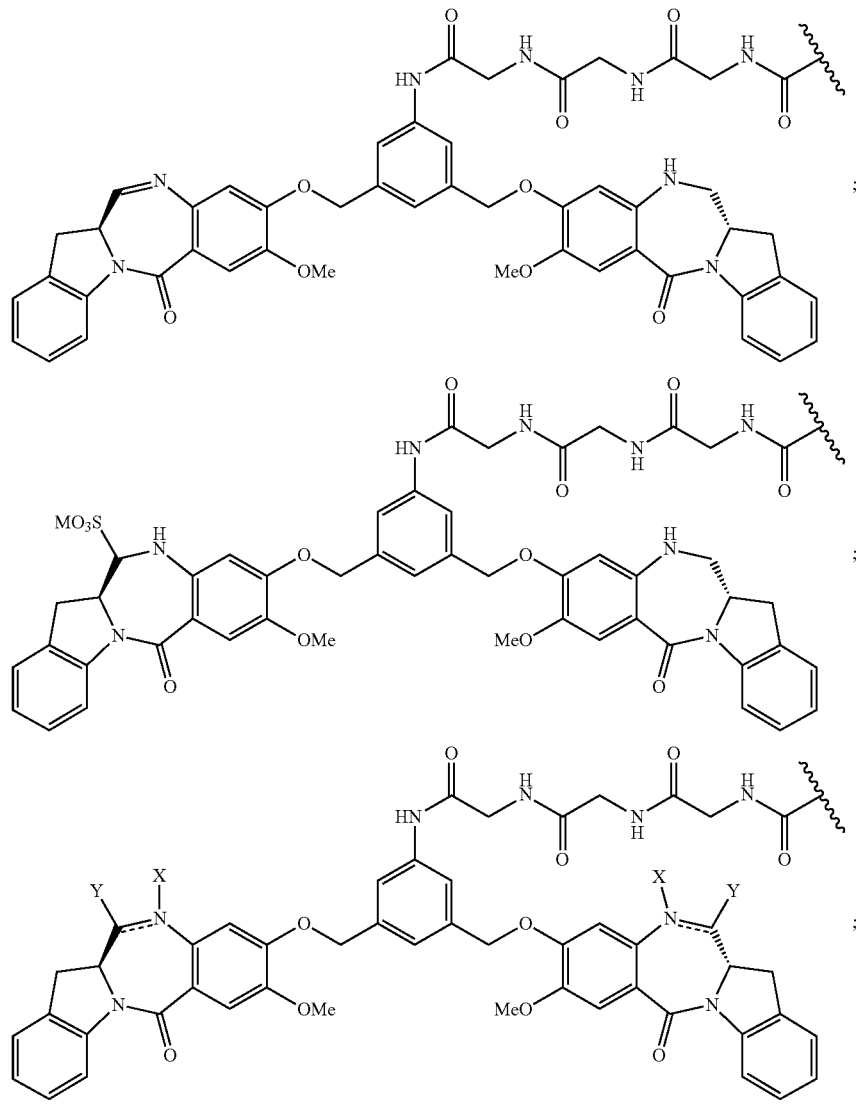

-continued
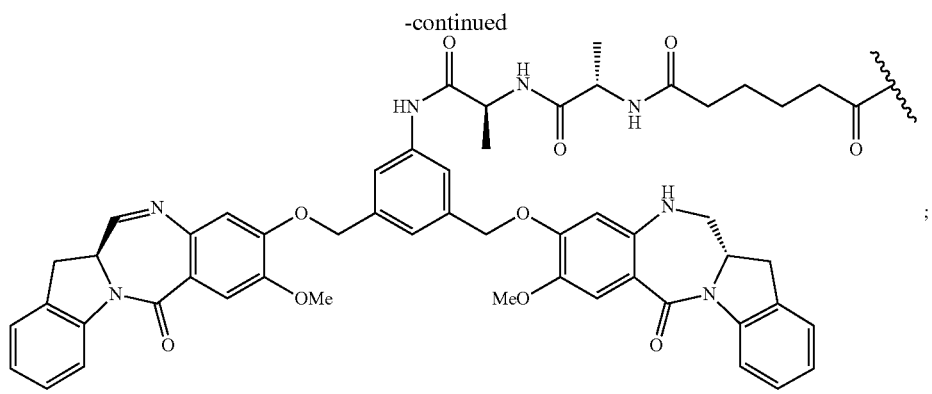
;
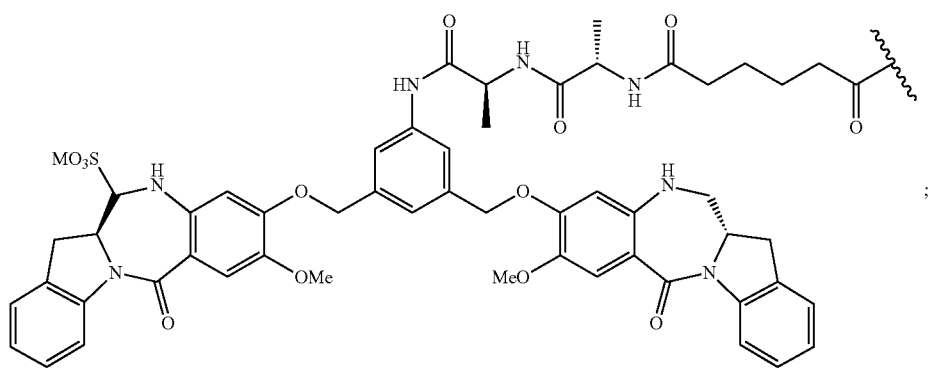
;
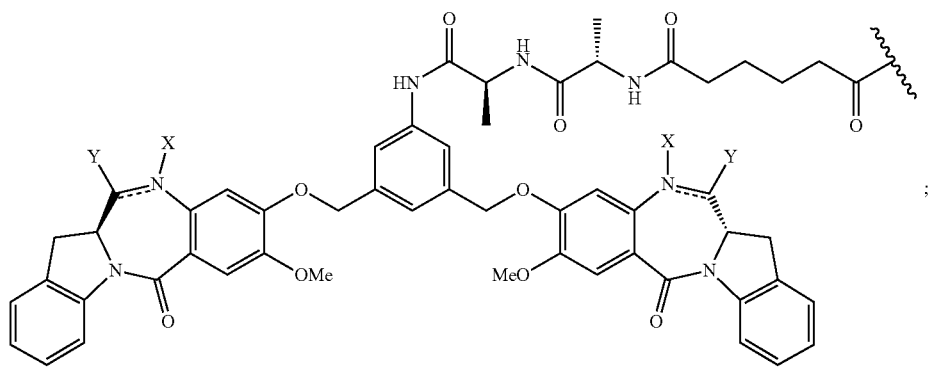
;
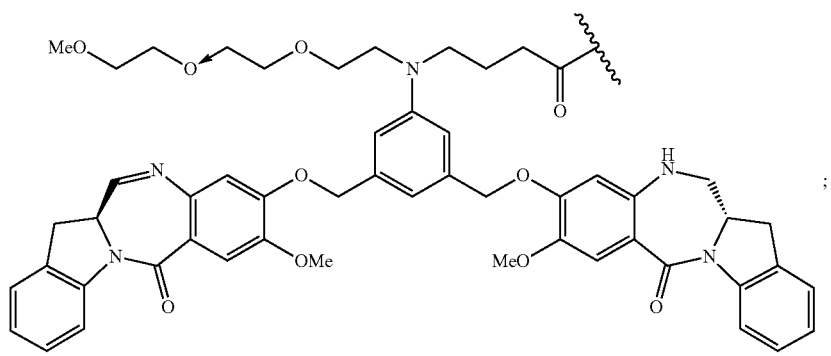
;

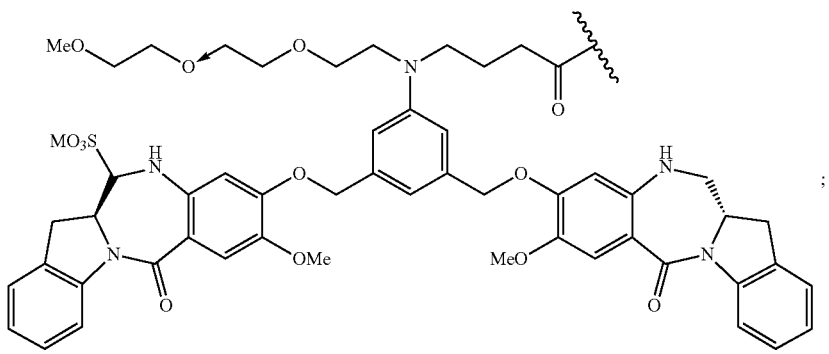

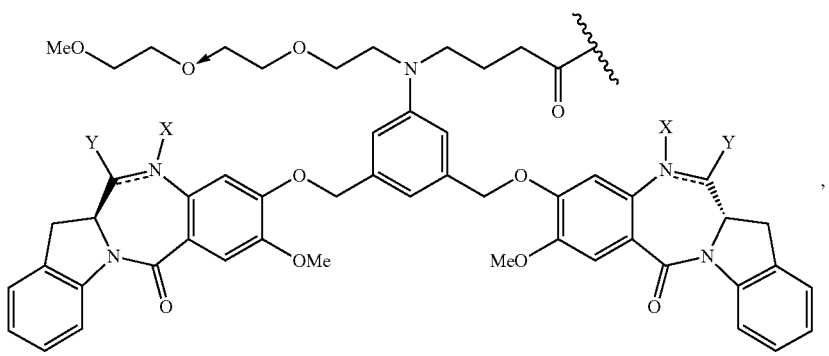

or a pharmaceutically acceptable salt thereof, wherein the double line == between N and C represents a single bond or a double bond, provided that when it is a double bond, X is absent and Y is —H, and when it is a single bond, X is —H, and Y is —SO$_3$M; and M is H$^+$ or a pharmaceutically acceptable cation.

In certain embodiments, M is H$^+$, Na$^+$ or K$^+$.

In certain embodiments, R$_{23}$ and R$_{24}$ are both H; and m' is an integer between 1 and 6. In certain embodiments, R$^{h'}$ is H.

In certain embodiments, -L-J$_{CB}$ is represented by the following structural formula:

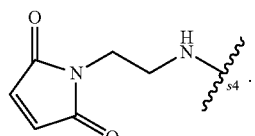

In certain embodiments, the compound is represented by the following structural formula:

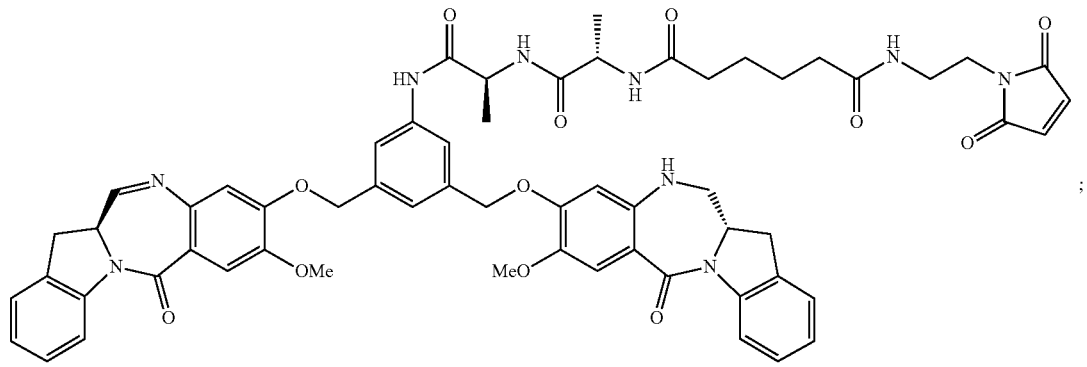

-continued
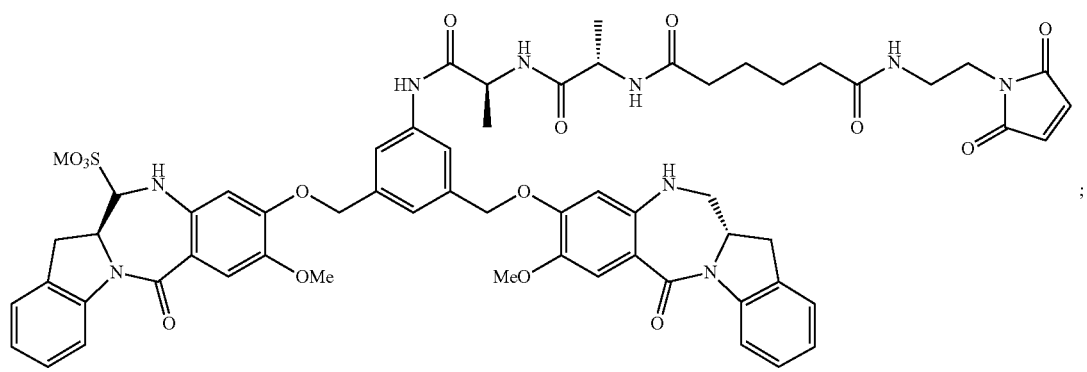
;
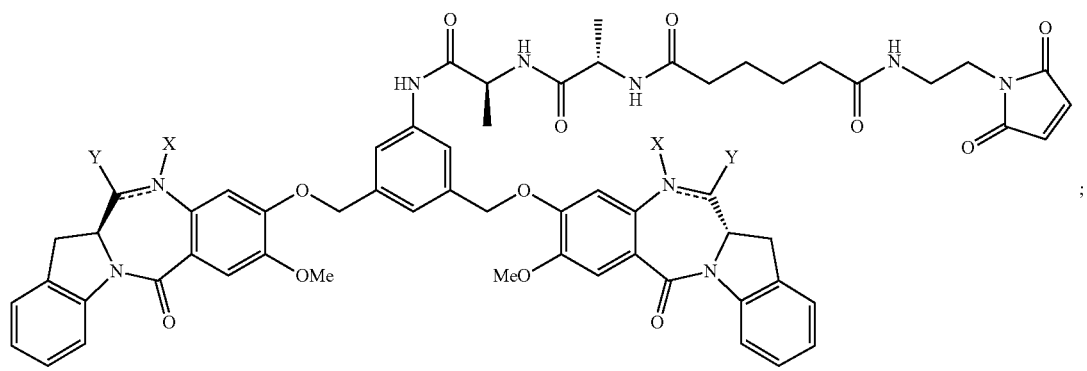
;
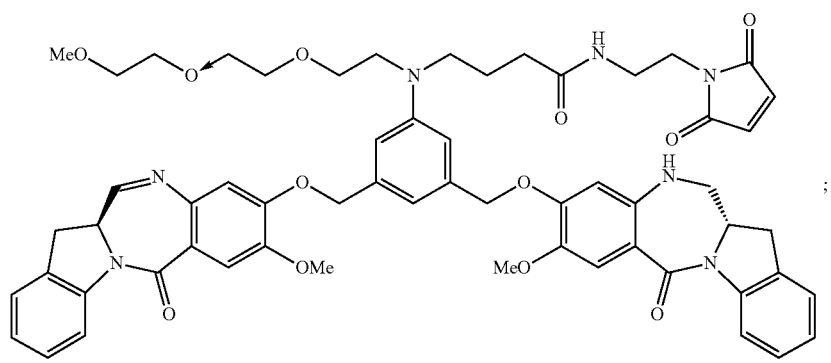
;
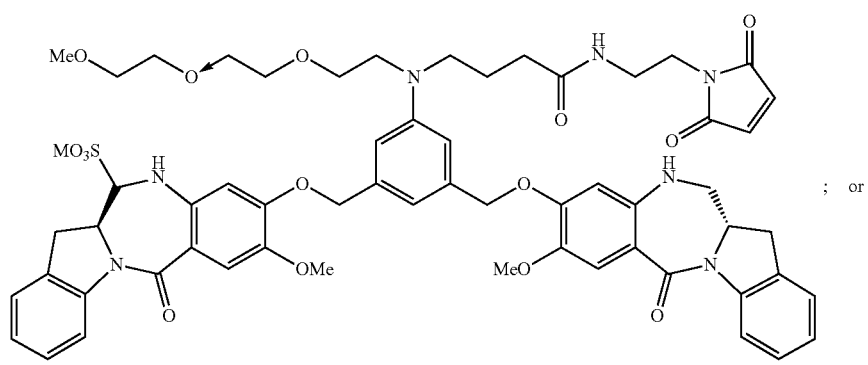
; or

-continued

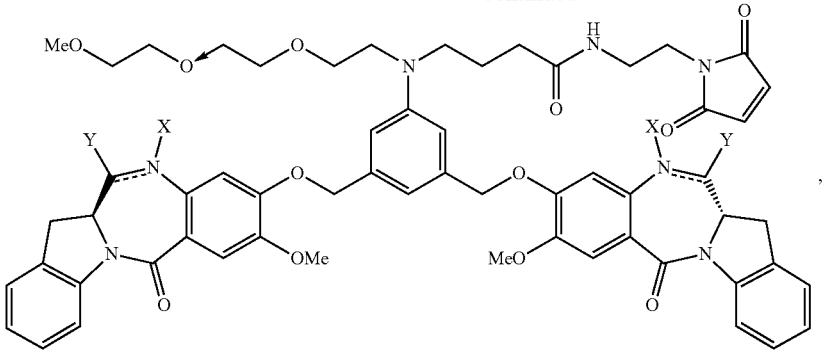

wherein the double line == between N and C represents a single bond or a double bond, provided that when it is a double bond, X is absent and Y is —H, and when it is a single bond, X is —H, and Y is —SO₃M; and M is H⁺ or a pharmaceutically acceptable cation.

In certain embodiments, M is H⁺, Na⁺ or K⁺.

Another aspect of the invention provides a pharmaceutical composition comprising a conjugate of the invention and a pharmaceutically acceptable carrier.

Another aspect of the invention provides a method of inhibiting abnormal cell growth or treating a proliferative disorder, an autoimmune disorder, destructive bone disorder, infectious disease, viral disease, fibrotic disease, neurodegenerative disorder, pancreatitis or kidney disease in a mammal, comprising administering to the mammal a therapeutically effective amount of a conjugate of the invention, and, an optionally, a second therapeutic agent.

In certain embodiments, the method inhibits abnormal cell growth or treats a proliferative disorder. In certain embodiments, the proliferative disorder is cancer, such as a hematological cancer or a solid tumor. Exemplary hematological cancer include leukemia and lymphoma. The leukemia may be acute myeloid leukemia (AML), acute lymphoblastic leukemia (ALL) such as acute B lymphoblastic leukemia (B-ALL), chronic myelogenous leukemia (CML), or chronic lymphocytic leukemia (CLL). The solid tumor may be melanoma, lung cancer (e.g., non-small cell lung cancer), ovarian cancer, endometrial cancer, peritoneal cancer, pancreatic cancer, breast cancer, prostate cancer, or cervical cancer.

It should be understood that any one embodiment described herein, including embodiments described only under one aspect of the invention but not other aspects, and including embodiments only appearing in the Examples, can be combined with any one or more other embodiments, unless explicitly disclaimed or improper.

BRIEF DESCRIPTION OF THE DRAWINGS

FIG. 1C shows LC-MS of the deglycosylated conjugate huMOV19-C442-D5, which was found to have an average of 2 mol D5/mol antibody by UV/Vis; 94.6% monomer by SEC; and 0.8% unconjugated D5 by SEC/reverse-phase HPLC.

FIG. 1D shows LC-MS of the deglycosylated conjugate huMOV19-C442-D4, which was found to have an average of 2 mol D4/mol antibody by UV-Vis; and 93.6% monomer by SEC.

FIG. 2 shows that the Cys-linked conjugates are at least as active as the Lys-linked conjugates across multiple target cell lines (e.g., the AML cell line EOL-1, the B-ALL cell line KOPN-8, and the CML cell line MOLM-1) expressing an antigen recognized by the antibody of the conjugates (i.e., CD123). The data curves linking open squares and open circles represent controls with excess unconjugated competing antibodies (i.e., chCD123-6), for curves linking filled squares and filled circles, respectively.

DETAILED DESCRIPTION OF THE INVENTION

Figure 1A:
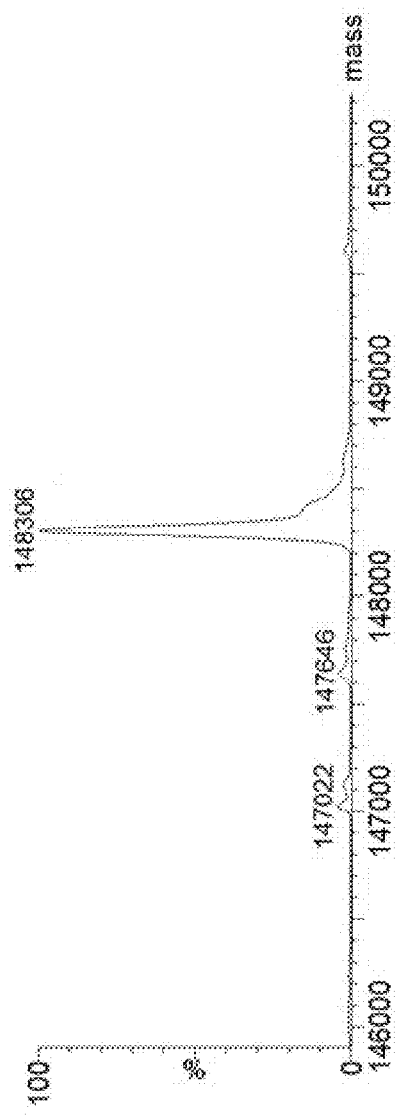
FIG. 1A shows LC-MS of the deglycosylated conjugate huMOV19-C442-Mal-CX1-1-DM1, which was found to have an average of 2 mol DM1/mol antibody by UV/Vis; 99.3% monomer by SEC; and no detectable unconjugated DM1 by HPLC on a HISEP column.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents that can be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, compound-linker molecules, conjugates, compositions, methods of making and using) and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

"Alkyl" or "linear or branched alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Alkenyl" or "linear or branched alkenyl" refers to linear or branched-chain monovalent hydrocarbon radical of two to twenty carbon atoms with at least one site of unsaturation, i.e., a carbon-carbon double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like. Preferably, the alkenyl has two to ten carbon atoms. More preferably, the alkyl has two to four carbon atoms.

"Alkynyl" or "linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The terms "cyclic alkyl" and "cycloalkyl" can be used interchangeably. They refer to a monovalent saturated carbocyclic ring radical. Preferably, the cyclic alkyl is 3 to 7 membered monocyclic ring radical. More preferably, the cyclic alkyl is cyclohexyl.

The term "cycloalklalkyl" refers to an alkyl group described above that is substituted with a cycloalkyl group.

The term "cyclic alkenyl" refers to a carbocyclic ring radical having at least one double bond in the ring structure.

The term "cyclic alkynyl" refers to a carbocyclic ring radical having at least one triple bond in the ring structure.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The terms "heterocycle," "heterocyclyl," and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle can be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco

[3.1.0]hexanyl, 3-azabicyclo[4.1.0]heptanyl, and azabicyclo [2.2.2]hexanyl. Spiro moieties are also included within the scope of this definition. Examples of a heterocyclic group wherein ring atoms are substituted with oxo (═O) moieties are pyrimidinonyl and 1,1-dioxo-thiomorpholinyl.

As used herein, a "5- or 6-membered nitrogen containing heterocycle" refers to a heterocycle having 5 or 6 ring atoms with at least one nitrogen ring atom. It can optionally further comprise 1 to 3 heteroatoms selected from O, N and S.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur.

Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups can be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclcyl include the oxidized forms such as NO, SO, and $SO_2$.

The term "halo" or "halogen" refers to F, Cl, Br or I.

As used herein, the term "haloalkyl" refers to an alkyl, as defined herein, that is substituted by one or more halo groups as defined herein. The haloalkyl can be monohaloalkyl, dihaloalkyl or polyhaloalkyl. A monohaloalkyl can have one fluoro, chloro, bromo, or iodo substituent. Dihaloalkyl or polyhaloalkyl can be substituted with two or more of the same halo atoms or a combination of different halo groups. Examples of haloalkyl include, but are not limited to, flouromethyl, difluoromethyl, trifluoromethyl, chloroamethyl, dichloromethyl, trichloromethyl, pentafluoroethyl, heptafluoropropyl, difluorochloromethyl, dichlorofluoromethyl, difluoroehtyl, diflosoropropyl, dichloroethyl and dichloropropyl.

"Alkoxy" used herein refers to alkyl-O—, wherein alkyl is defined herein above. Examples of alkoxy include, not are not limited to, methoxy, ethoxy, propoxy, 2-propoxy, butoxy, tert-butoxy, pentyloxy, hexyloxy, and the like.

The alkyl, haloalkyl, alkoxy, alkenyl, alkynyl, cyclic alkyl, cyclic alkenyl, cyclic alkynyl, carbocyclyl, aryl, heterocyclyl and heteroaryl described above can be optionally substituted with one or more (e.g., 2, 3, 4, 5, 6 or more) substituents.

If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated).

If a substituent is described as being "optionally substituted," the substituent can be either (1) not substituted, or (2) substituted. If a carbon of a substituent is described as being optionally substituted with one or more of a list of substituents, one or more of the hydrogens on the carbon (to the extent there are any) can separately and/or together be replaced with an independently selected optional substituent. If a nitrogen of a substituent is described as being optionally substituted with one or more of a list of substituents, one or more of the hydrogens on the nitrogen (to the extent there are any) can each be replaced with an independently selected optional substituent. One exemplary substituent can be depicted as —NR'R", wherein R' and R" together with the nitrogen atom to which they are attached, can form a heterocyclic ring. The heterocyclic ring formed from R' and R" together with the nitrogen atom to which they are attached can be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group can include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent can be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocycyclyl, halogen, guanidinium [—NH(C═NH)$NH_2$], —$OR^{100}$, $NR^{101}R^{102}$, —$NO_2$, —$NR^{101}COR^{102}$, —$SR^{100}$, a sulfoxide represented by —$SOR^{101}$, a sulfone represented by —$SO_2R^{101}$, a sulfonate —$SO_3M$, a sulfate-$OSO_3M$, a sulfonamide represented by —$SO_2NR^{101}R^{102}$, cyano, an azido, —$COR^{101}$, —$OCOR^{101}$, —OCONR$^{101}$R$^{102}$ and a polyethylene glycol unit (—OCH$_2$CH$_2$)$_n$R$^{101}$ wherein M is H or a cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclcyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocycycl, —SR$^{101}$, —SOR$^{101}$, —SO$_2$R$^{11}$ and —SO$_3$M.

The number of carbon atoms in a group can be specified herein by the prefix "C$_{x\text{-}xx}$" or "C$_x$-C$_{xx}$", wherein x and xx are integers. For example, "C$_{1\text{-}4}$alkyl" or "C1-C4 alkyl" is an alkyl group having from 1 to 4 carbon atoms.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "linkable to a cell binding agent" as used herein refers to the compounds described herein or derivatives thereof comprising at least one linking group or a precursor thereof suitable to bond these compounds or derivatives thereof to a cell binding agent.

The term "precursor" of a given group refers to any group that can lead to that group by any deprotection, a chemical modification, or a coupling reaction.

The term "chiral" refers to molecules that have the property of non-superimposability of the mirror image partner, while the term "achiral" refers to molecules that are superimposable on their mirror image partner.

The term "stereoisomer" refers to compounds that have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as crystallization, electrophoresis and chromatography.

"Enantiomers" refer to two stereoisomers of a compound that are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies that are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

One preferred form of prodrug of the invention includes compounds (with or without any linker groups) and conjugates of the invention comprising an adduct formed between an imine bond of the compounds/conjugates and an imine reactive reagent. Another preferred form of prodrug of the invention includes compounds such as those of formula (I)-(IV), wherein when the double line $=\!=$ between N and C represents a single bond, X is H or an amine protecting group, and the compound becomes a prodrug. A prodrug of the invention can contain one or both forms of prodrugs described herein (e.g., containing an adduct formed between an imine bond of the compounds/conjugates and an imine reactive reagent, and/or containing a Y leaving group when X is —H).

The term "imine reactive reagent" refers to a reagent that is capable of reacting with an imine group. Examples of imine reactive reagent includes, but is not limited to, sulfites (H$_2$SO$_3$, H$_2$SO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono, di, tri, and tetra-thiophosphates (PO$_3$SH$_3$, PO$_2$S$_2$H$_3$, POS$_3$H$_3$, PS$_4$H$_3$ or a salt of PO$_3$S$_3^-$, PO$_2$S$_2^{3-}$, POS$_3^{3-}$ or PS$_4^{3-}$ formed with a cation), thio phosphate esters (($R^i$O)$_2$PS(O$R^i$)), $R^i$SH, $R^i$SOH, $R^i$SO$_2$H, $R^i$SO$_3$H), various amines (hydroxyl amine (e.g., NH$_2$OH), hydrazine (e.g., NH$_2$NH$_2$), NH$_2$O—$R^i$, $R^i$, NH—$R^i$, NH$_2$—$R^i$), NH$_2$—CO—NH$_2$, NH$_2$—C(=S)—NH$_2$' thiosulfate (H$_2$S$_2$O$_3$ or a salt of S$_2$O$_3^{2-}$ formed with a cation), dithionite (H$_2$S$_2$O$_4$ or a salt of S$_2$O$_4^{2-}$ formed with a cation), phosphorodithioate (P(=S)(O$R^k$)(SH)(OH) or a salt thereof formed with a cation), hydroxamic acid ($R^k$C(=O)NHOH or a salt formed with a cation), hydrazide ($R^k$CONHNH$_2$), formaldehyde sulfoxylate (HOCH$_2$SO$_2$H or a salt of HOCH$_2$SO$_2^-$ formed with a cation, such as HOCH$_2$SO$_2^-$Na$^+$), glycated nucleotide (such as GDP-mannose), fludarabine or a mixture thereof, wherein $R^i$ and $R^{i'}$ are each independently a linear or branched alkyl having 1 to 10 carbon atoms and are substituted with at least one substituent selected from —N($R^j$)$_2$, —CO$_2$H, —SO$_3$H, and —PO$_3$H; $R^i$ and $R^{i'}$ can be further optionally substituted with a substituent for an alkyl described herein; $R^i$ is a linear or branched alkyl having 1 to 6 carbon atoms; and $R^k$ is a linear, branched or cyclic alkyl, alkenyl or alkynyl having 1 to 10 carbon atoms, aryl, heterocyclyl or heteroaryl (preferably, $R^k$ is a linear or branched alkyl having 1 to 4 carbon atoms; more preferably, $R^k$ is methyl, ethyl or propyl). Preferably, the cation is a monovalent cation, such as Na$^+$ or K$^+$. Preferably, the imine reactive reagent is selected from sulfites, hydroxyl amine, urea and hydrazine. More preferably, the imine reactive reagent is NaHSO$_3$ or KHSO$_3$.

As used herein, a "benzodiazepine" compound is a compound having a benzodiazepine core structure. The benzodiazepine core can be substituted and/or fused with one or more ring structures. It also includes a compound having two benzodiazepine core linked by a linker. The imine functionality (—C=N—) as part of benzodiazepine core can be reduced.

As used herein, a "indolinobenzodiazepine" (IBD) compound is a compound having an indolinobenzodiazepine core structure. The indolinobenzodiazepine can be substituted. It also includes a compound having two indolinobenzodiazepine core linked by a linker. The imine functionality (—C=N—) as part of indolinobenzodiazepine core can be reduced.

The phrase "pharmaceutically acceptable salt" as used herein, refers to pharmaceutically acceptable organic or inorganic salts of a compound of the invention.

Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt can involve the inclusion of another molecule such as an acetate ion, a succinate ion or other counter ion. The counter ion can be any organic or inorganic moiety that stabilizes the charge on the parent compound. Furthermore, a pharmaceutically acceptable salt can have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt can be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt can be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound that further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or precancerous cells.

A "therapeutic agent" encompasses a biological agent, such as an antibody, a peptide, a protein, an enzyme, or a chemotherapeutic agent. The therapeutic agent also encompasses immuno-conjugates of cell-binding agents (CBAs) and chemical compounds, such as antibody-drug conjugates (ADCs). The drug in the conjugates can be a cytotoxic agent, such as one described herein.

A "chemotherapeutic agent" is a chemical compound useful in the treatment of cancer.

A "metabolite" or "catabolite" is a product produced through metabolism or catabolism in the body of a specified compound, a derivative thereof, or a conjugate thereof, or salt thereof.

Metabolites of a compound, a derivative thereof, or a conjugate thereof, can be identified using routine techniques known in the art and their activities determined using tests such as those described herein. Such products can result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "bifunctional crosslinking agent," "bifunctional linker" or "crosslinking agents" refers to modifying agents that possess two reactive groups; one of which is capable of reacting with a cell binding agent while the other one reacts with the cytotoxic compound to link the two moieties together. Such bifunctional crosslinkers are well known in the art (see, for example, Isalm and Dent in *Bioconjugation* chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N-(3-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy) sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent can comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety can contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

In one embodiment, the linking group with a reactive group attached at one end, such as a reactive ester, is selected from the following:

—O(CR$_{20}$R$_{21}$)$_m$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—O(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—O(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—O(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—O(CR$_{20}$R$_{21}$)$_m$(pyrrolo)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—O(CR$_{20}$R$_{21}$)$_m$A''$_{m''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—S(CR$_{20}$R$_{21}$)$_m$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—S(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—S(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—S(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—S(CR$_{20}$R$_{21}$)$_m$(pyrrolo)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—S(CR$_{20}$R$_{21}$)$_m$A''$_{m''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—NR$_{33}$(C=O)$_{p''}$(CR$_{20}$R$_{21}$)$_m$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—NR$_{33}$(C=O)$_{p''}$(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—NR$_{33}$(C=O)$_{p''}$(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—NR$_{33}$(C=O)$_{p''}$(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X,
—NR$_{33}$(C=O)$_{p''}$(CR$_{20}$R$_{21}$)$_m$(pyrrolo)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—NR$_{33}$(C=O)$_{p''}$(CR$_{20}$R$_{21}$)$_m$A''$_{m''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X,
—(CR$_{20}$R$_{21}$)$_m$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—(CR$_{20}$R$_{21}$)$_m$A''$_{m''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—(CR$_{20}$R$_{21}$)$_m$(CR$_{29}$=N—NR$_{30}$)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—(CR$_{20}$R$_{21}$)$_m$(CR$_{29}$=N—NR$_{30}$)$_{n'}$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',
—(CR$_{20}$R$_{21}$)$_m$(CR$_{29}$=N—NR$_{30}$)$_{n'}$(alkynyl)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$—(CO)$_t$X'',
—(CR$_{20}$R$_{21}$)$_m$(CR$_{29}$=N—NR$_{30}$)$_{n'}$A''$_{m''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', wherein:

m, n, p, q, m', n', t' are integer from 1 to 10, or are optionally 0;

t, m'', n'', and p'' are 0 or 1;

X'' is selected from OR$_{36}$, SR$_{37}$, NR$_{38}$R$_{39}$, wherein R$_{36}$, R$_{37}$, R$_{38}$, R$_{39}$ are H, or linear, branched or cyclic alkyl, alkenyl or alkynyl having from 1 to 20 carbon atoms and, or, a polyethylene glycol unit —(OCH$_2$CH$_2$)$_n$, R$_{37}$, optionally, is a thiol protecting group when t=1, COX'' forms a reactive ester selected from N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide bond formation;

Y'' is absent or is selected from O, S, S—S or NR$_{32}$, wherein R$_{32}$ has the same definition as given above for R; or when Y'' is not S—S and t=0, X'' is selected from a maleimido group, a haloacetyl group or SR$_{37}$, wherein R$_{37}$ has the same definition as above;

A'' is a residue of an amino acid or a polypeptide containing between 2 to 20 amino acid units;

R$_{20}$, R$_{21}$, R$_{22}$, R$_{23}$, R$_{24}$, R$_{25}$, R$_{26}$, and R$_{27}$ are the same or different, and are —H or a linear or branched alkyl having from 1 to 5 carbon atoms;

R$_{29}$ and R$_{30}$ are the same or different, and are —H or alkyl from 1 to 5 carbon atoms;

R$_{33}$ is —H or linear, branched or cyclic alkyl, alkenyl or alkynyl having from 1 to 12 carbon atoms, a polyethylene glycol unit R—(OCH$_2$CH$_2$)$_n$—, or R$_{33}$ is —COR$_{34}$, —CSR$_{34}$, —SOR$_{34}$, or —SO$_2$R$_{34}$, wherein R$_{34}$ is H or linear, branched or cyclic alkyl, alkenyl or alkynyl having from 1 to 20 carbon atoms or, a polyethylene glycol unit —(OCH$_2$CH$_2$)$_n$; and one of R$_{40}$ and R$_{41}$ is optionally a negatively or positively charged functional group and the other is H or alkyl, alkenyl, alkynyl having 1 to 4 carbon atoms.

Any of the above linking groups can be present in any of the compounds, drug-linker compounds, or conjugates of the invention, including replacing the linking groups of any of the formulas described herein.

The term "amino acid" refers to naturally occurring amino acids or non-naturally occurring amino acid. In one embodiment, the amino acid is represented by NH$_2$—C(R$^{aa}$R$^{aa'}$)—C(=O)OH, wherein R$^{aa}$ and R$^{aa'}$ are each independently H, an optionally substituted linear, branched or cyclic alkyl, alkenyl or alkynyl having 1 to 10 carbon atoms, aryl, heteroaryl or heterocyclyl or R$^{aa}$ and the N-terminal nitrogen atom can together form a heteroycyclic ring (e.g., as in proline). The term "amino acid residue" refers to the corresponding residue when one hydrogen atom is removed from the amine and/or carboxy end of the amino acid, such as —NH—C($R^{aa\prime}R^{aa}$)—C(=O)O—.

The term "cation" refers to an ion with positive charge. The cation can be monovalent (e.g., $Na^+$, $K^+$, etc.), bi-valent (e.g., $Ca^{2+}$, $Mg^{2+}$, etc.) or multi-valent (e.g., $Al^{3+}$ etc.). Preferably, the cation is monovalent.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of a compound or a conjugate can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

The term "cysteine engineered antibody" includes an antibody with at least one Cys that is not normally present at a given residue of the antibody light chain or heavy chain. Such Cys, which may also be referred to as "engineered Cys," can be introduced, for example, by standard recombinant technology (e.g., by replacing the coding sequence for a non-Cys residue at the target residue with a coding sequence for Cys). In certain embodiments, the Cys engineered antibody of the invention has an engineered Cys in the heavy chain. In certain embodiments, the engineered Cys is in or near the $CH_3$ domain of the heavy chain. In certain embodiments, the engineered Cys is at residue 442 of the heavy chain (EU/OU numbering).

As used herein, all antibody amino acid residues described herein are numbered according to the EU index, Kabat et al., *Sequences of Proteins of Immunological Interest*, 5th Ed., NIH publication No. 91-3242, 1991 (EU/OU numbering, entire content incorporated herein by reference). The common isotypes are referred to as G1, G2, G4, etc.

Certain examples below refer to various humanized anti-CD123 antibodies, the nomenclature of such antibodies are briefly described here. One class of huCD123-6 antibodies are humanized by grafting the 6 CDRs from the heavy and light chains of the murine anti-CD123 antibody muCD123-6. In those antibodies, the letter "G" immediately follows the clone designation (i.e., huCD123-6), which is in turn followed by a version number that designates the origin of the human light chain and heavy chain variable region sequences. Thus huCD123-6Gv4.6 refers to the humanized CD123 antibody based on grafting ("G") the 6 CDR regions from the corresponding muCDR123-6 antibody, onto the human light chain variable region Gv4 and the heavy chain variable region Gv6. Similarly, -Gv4.7 comprises human light chain variable region Gv4 and heavy chain variable region Gv7.

Another class of huCD123-6 antibodies are humanized by way of resurfacing. The resurfaced antibody having the resurfaced heavy chain sequence huCD123-6rhv1.1 and the resurfaced light chain sequence huCD123-6rlv1.0 is huCD123-6Rv1.1.

When any of the anti-CD123 antibody comprising an engineered Cys residue as described above, the antibody may contain the designation CysMab or C442, such as huCD123-6Gv4.7-C442. The C442 residue can be conjugated with a cytotoxic drug/agent through the free thiol group of the C442 residue, such as through reacting with a thiol-reactive agent of the cytotoxic drug (e.g., a maleimido group). A representative list of such cytotoxic drugs with thiol-reactive groups—D4-D7—and their synthesis, are described in Example 1 and listed in the table below. Additional related compounds D1, D2, DGN462, and D3, which have the same core structures as D4, D5, D6, and D7, respectively, but do not have thiol-reactive group, are also listed below. D1-D3 and DGN462 are not able to link to C442 for lack of the Maleimido thiol-reactive group.

| Compound No. in patent application | Structure |
|---|---|
| D1 | 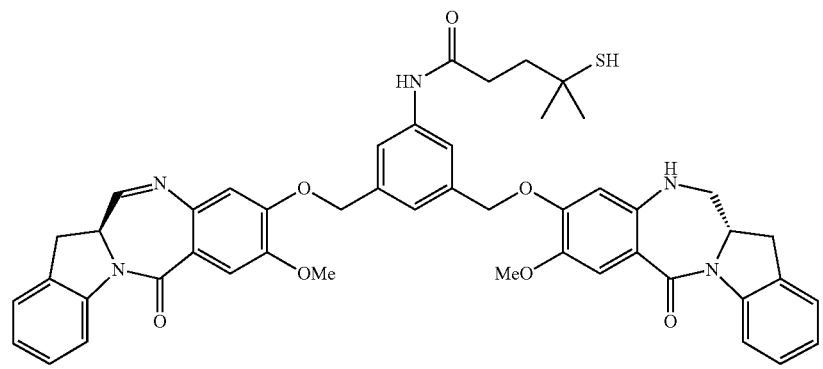 [SMILES: COc1cc2c(cc1OCc1cc(COc3cc4c(cc3OC)C(=O)N3c5ccccc5C[C@H]3CN4)cc(NC(=O)CCC(C)(C)S)c1)N=C[C@@H]1Cc3ccccc3N1C2=O] |

-continued
| Compound No. in patent application | Structure |
|---|---|
| D2 | 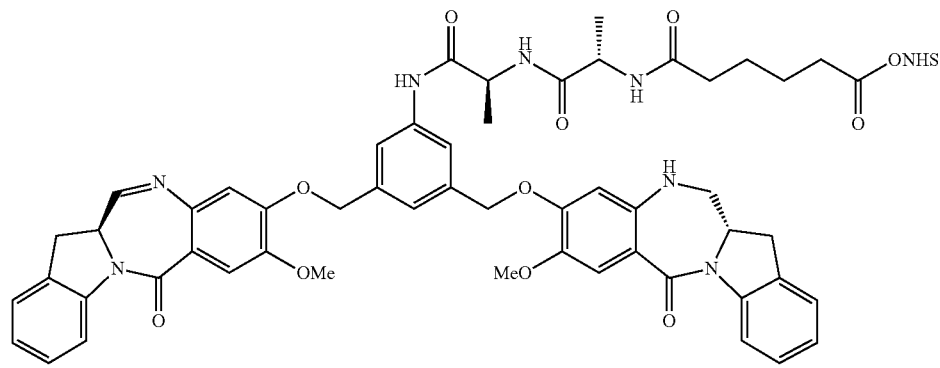 |
| DGN462 | 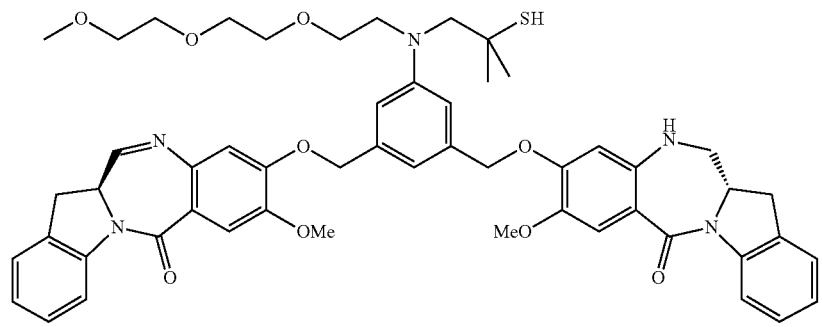 [SMILES: COCCOCCOCCN(CC(C)(C)S)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1] |
| D3 | 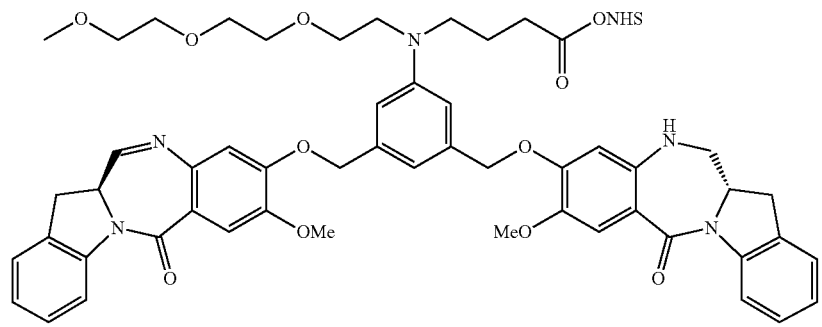 |
| D4 | 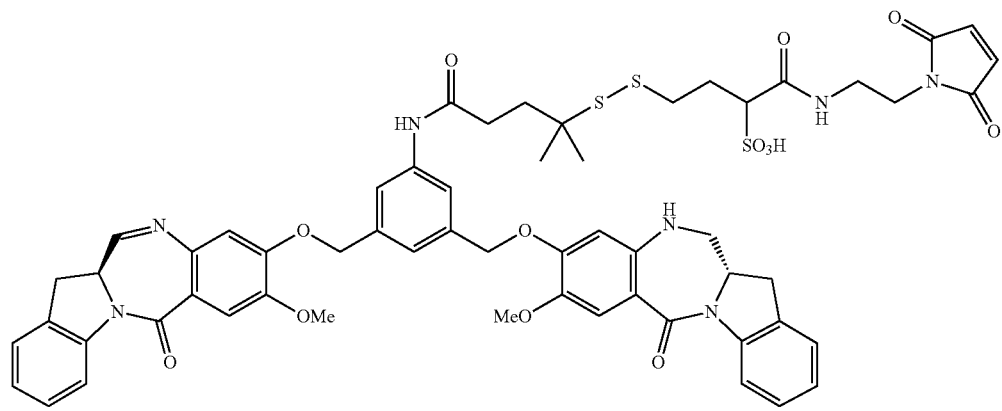 [SMILES: COc1cc2c(cc1OCc1cc(COc3cc4c(cc3OC)C(=O)N3c5ccccc5C[C@H]3CN4)cc(NC(=O)CCC(C)(C)SSCCC(C(=O)NCCN3C(=O)C=CC3=O)S(=O)(=O)O)c1)N=C[C@@H]1Cc3ccccc3N1C2=O] |

| Compound No. in patent application | Structure |
|---|---|
| D5 | 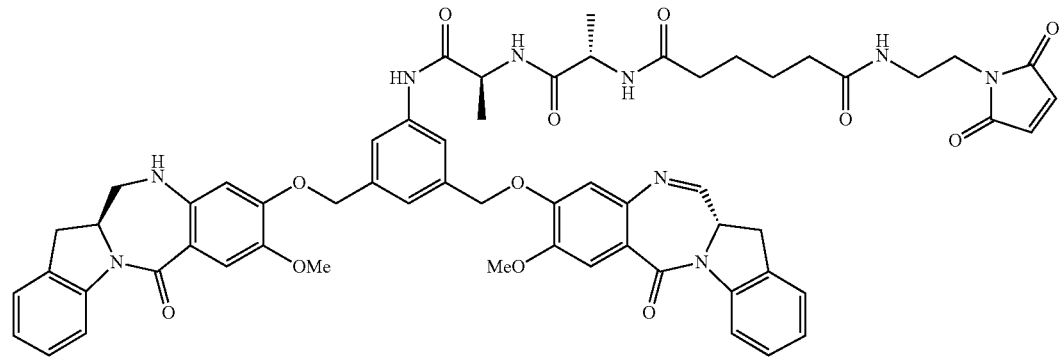 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O] |
| D6 | 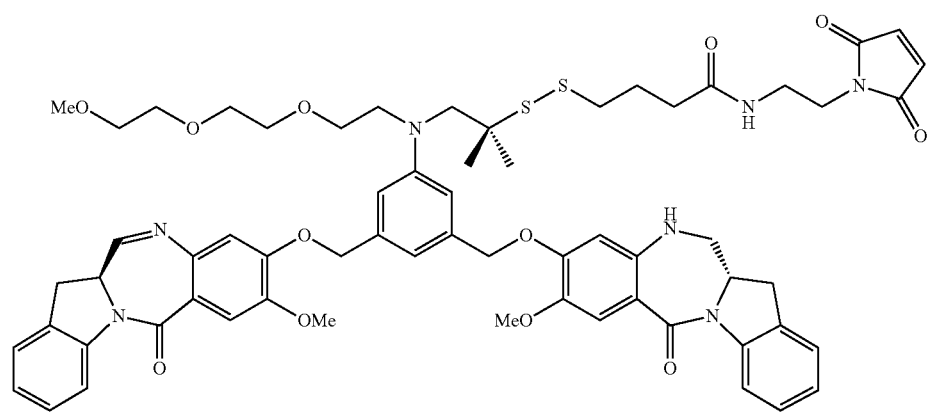 |
| D7 | 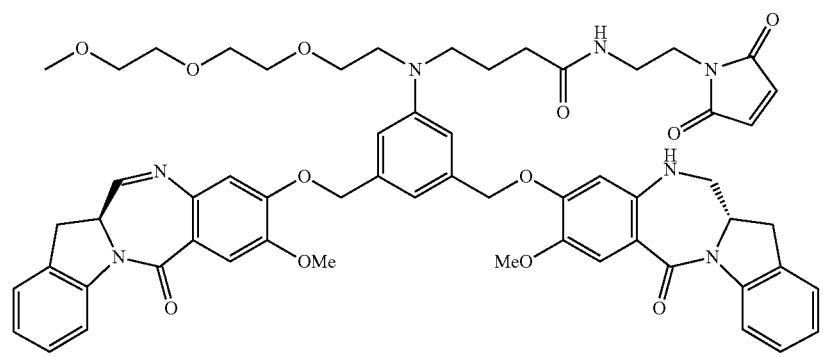 [SMILES: COCCOCCOCCN(CCCC(=O)NCCN1C(=O)C=CC1=O)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1] |
| D5' | 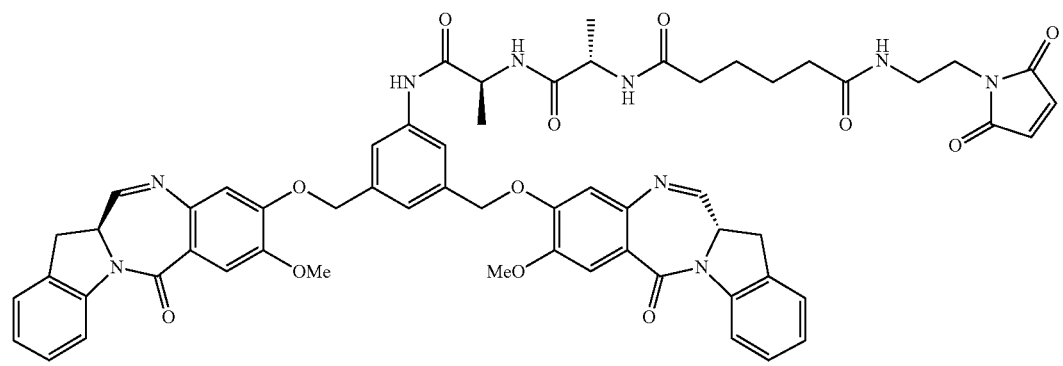 [SMILES: COc1cc2c(cc1OCc1cc(COc3cc4c(cc3OC)C(=O)N3c5ccccc5C[C@H]3C=N4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O] |

Conjugates between the antibodies of the invention with D4-D7 through the free thiol group simply recite the name of the antibody and the linked cytotoxic drug. For example, huCD123-6Gv4.7-C442-D5 is a conjugate of compound D5 and the huCD123-6Gv4.7 through the C442 thiol group, and huMov19-C442-D5 is a conjugate of compound D5 and the huMov19 antibody through the C442 thiol group. In certain embodiments, compounds such as D1 requires an additional linker (e.g., a sulfo-SPDB linker, or sSPDB) to be conjugated to an antibody, such as to the Lys side chain amino groups. The structure of the Lys-linked conjugate huCD123-6Gv4.7-sulfo-SPDB-D1 (or huCD123-6Gv4.7-sulfo-SPDB-D1) is shown below.

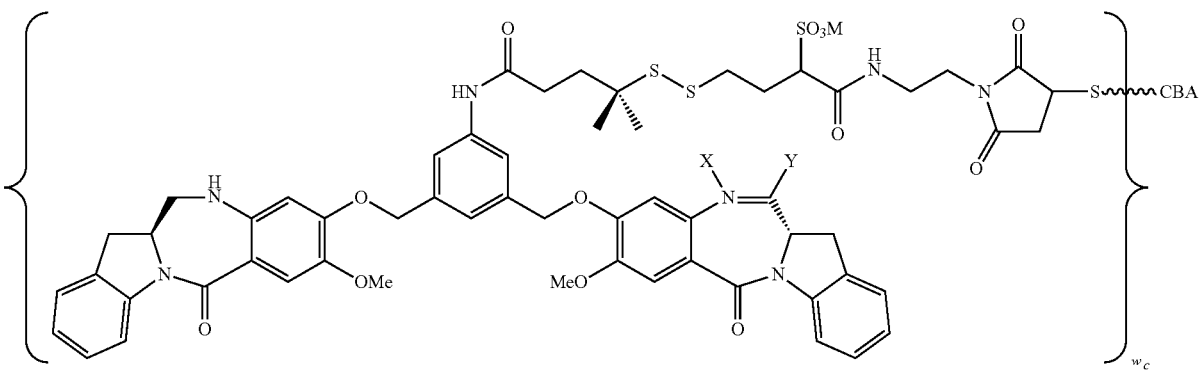

Note that certain CD123 antibodies has "S2" and/or "S3" in the name of such antibodies or immuno-conjugates thereof, which should not be confused with the "s2" or "s3" designations in chemical formulae that represent sites of connection or covalent bond formation.

Conjugates and Compounds of the Present Invention

In a first aspect, the present invention provides cell-binding agent-cytotoxic agent conjugates, wherein the cell-binding agent (CBA) is covalently linked to the cytotoxic agent through a thiol (—SH) group located on the CBA. In certain embodiments, the free thiol group is on an engineered Cys residue in the heavy chain $CH_3$ region of an antibody, at the EU/OU numbering position 442 of that heavy chain (or C442 for short).

Thus in one embodiment, the antibody-cytotoxic agent conjugate of the present invention comprises an antibody having a cysteine residue (e.g., at the EU/OU numbering position 442 of the heavy chain) and a cytotoxic agent, wherein the antibody is covalently linked to the cytotoxic agent through the cysteine residue (e.g., C442). The conjugate is represented by the following formula:

wherein:

Ab is the antibody having a cysteine residue at position 442 (EU/OU numbering) of the heavy chain;

$S_{442}$ represents the thiol group from the cysteine residue at position 442 of the heavy chain of the antibody that is covalently linked to the $J_{CB}'$ group;

$J_{CB}'$ is a linking moiety connecting the cysteine residue with the group L;

L is a linker connecting the cytotoxic agent and the $J_{CB}'$ moiety;

D is a cytotoxic agent covalently linked to the group L; and w is 1 or 2.

In one embodiment, the cysteine residue at position 442 is recombinantly introduced into said Ab.

In a second aspect, the present invention provides a cytotoxic agent-linker compound that are capable of reacting with the antibodies of the present invention having a free cysteine residue to form the conjugates of the present invention.

In one embodiment, the cytotoxic agent-linker compound of the present invention is represented by the following structural formula:

wherein:

$J_{CB}$ is a linking group capable of forming a covalent bond with the antibody described herein;

L is a linker connecting the cytotoxic agent represented by D and $J_{CB}$ group; and D is a cytotoxic agent covalently linked to the group L.

In one embodiment, $J_{CB}$ is a thiol-reactive group.

The following describes certain embodiments and specific embodiments for the first and second aspects of the invention.

In a $1^{st}$ embodiment, for conjugates of formula (I) in the first aspect of the invention, $J_{CB}'$ is

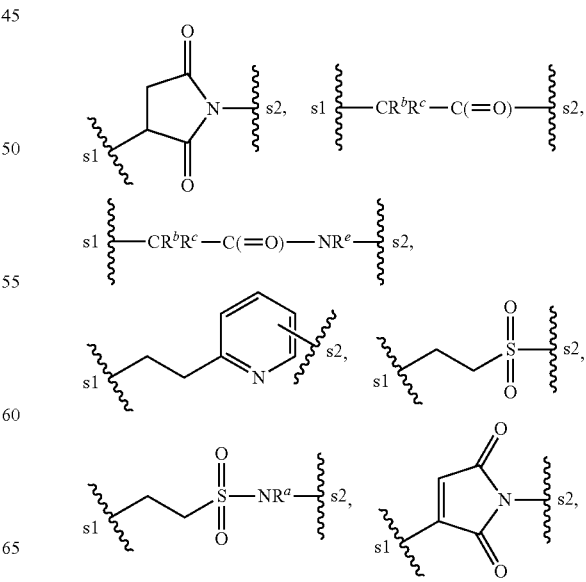

-continued

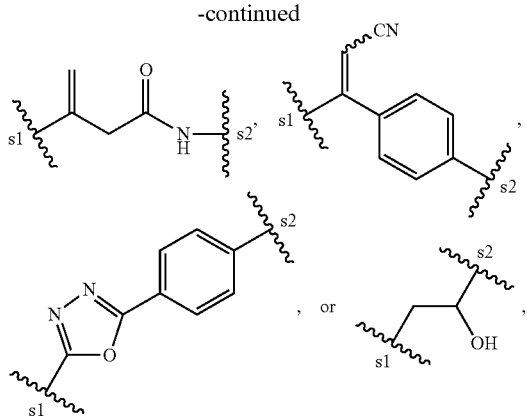

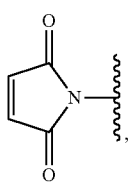

wherein s1 is the site covalently linked to the cysteine residue of the antibody and s2 is the site covalently linked to the group L; and $R^a$, $R^b$, $R^c$, and $R^e$, for each occurrence, are independently H or an optionally substituted alkyl; and the remaining variables are as described above for formula (I). In a specific embodiment, $R^a$, $R^b$, $R^c$, and $R^e$, for each occurrence, are independently H or a $C_{1-3}$alkyl. In another specific embodiment, $R^a$, $R^b$, $R^c$, and $R^e$ are all H.

Also in the 1$^{st}$ embodiment, for compounds of formula (II) in the second aspect of invention, $J_{CB}$ is

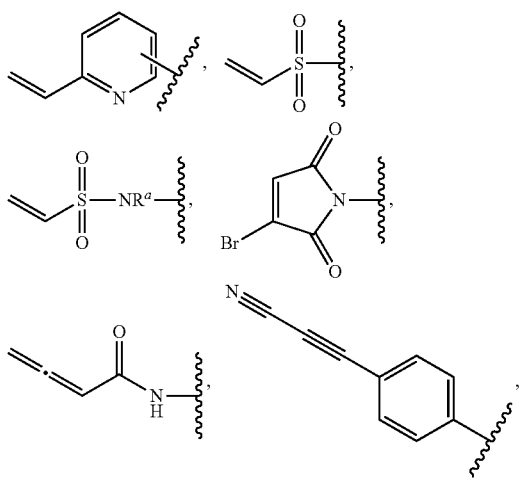

$R^a$, $R^b$, $R^c$, and $R^e$, for each occurrence, are independently H or an optionally substituted alkyl; and the remaining variables are as described above for formula (II).

In a 2$^{nd}$ embodiment, for conjugates of formula (I) in the first aspect of the invention, $J_{CB}'$ is

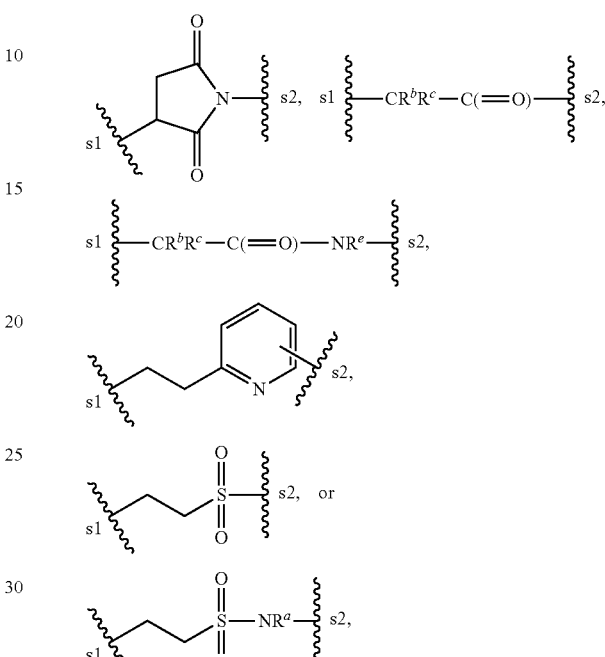

wherein s1 is the site covalently linked to the cysteine residue of the antibody and s2 is the site covalently linked to the group L; and $R^a$, $R^b$, $R^c$, and $R^e$, for each occurrence, are independently H or an optionally substituted alkyl; and the remaining variables are as described above for formula (I) in the 1$^{st}$ embodiment. In a specific embodiment, $R^a$, $R^b$, $R^c$, and $R^e$, for each occurrence, are independently H or a $C_1$-3alkyl. In another specific embodiment, $R^a$, $R^b$, $R^c$, and $R^e$ are all H.

Also in the 2$^{nd}$ embodiment, for compounds of formula (II) in the second aspect of invention, $J_{CB}$ is

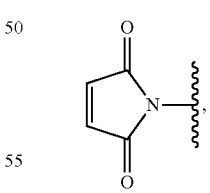

X'—CR$^b$R$^c$—C(=O)—, X'—CR$^b$R$^c$—C(=O)—NR$^e$—

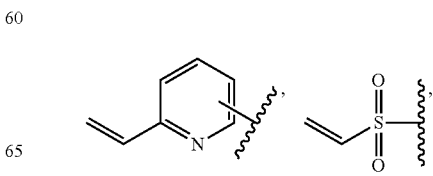

-continued

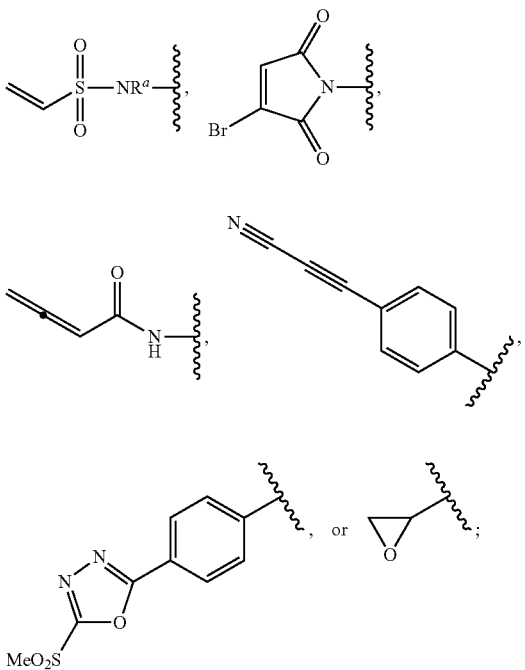

$R^a$, $R^b$, $R^c$, and $R^e$, for each occurrence, are independently H or an optionally substituted alkyl; and the remaining variables are as described above for formula (II) in the $1^{st}$ embodiment.

In a $3^{rd}$ embodiment, for conjugates of formula (I) in the first aspect of the invention, $J_{CB}'$ is

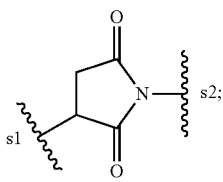 [SMILES: *C1CC(=O)N(*)C1=O]

and the remaining variables are as described above for formula (I).

Also in the $3^{rd}$ embodiment, for compounds of formula (II) in the second aspect of invention, $J_{CB}'$ is

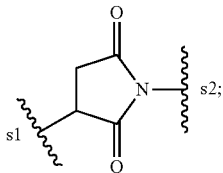 [SMILES: *C1CC(=O)N(*)C1=O]

and the remaining variables are as described above for formula (II).

In a $4^{th}$ embodiment, for conjugates of formula (I) of the first aspect of invention and compounds of formula (II) of the second aspect of the invention, -L- is represented by the following structural formula:

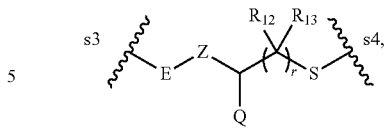

(L1)

wherein:
s3 is the site covalently linked to the $J_{CB}'$ group and s4 is the site covalently linked to the group D;
E is $-(CR_{10}R_{11})_q-$, a cycloalkyl or a cycloalkylalkyl;
Z is absent, $-SO_2NR_9-$, $-NR_9SO_2-$, $-C(=O)-NR_9-$, $-NR_9-C(=O)-$, $-C(=O)-O-$, $-O-C(=O)-$, $-C(=O)-NR_9-(CH_2CH_2O)_p-$, $-NR_9-C(=O)-(CH_2CH_2O)-$, $-(OCH_2CH_2)-C(=O)NR_9-$, or $-(OCH_2CH_2)_p-NR_9-C(=O)-$;
p is an integer from 1 to 24;
Q is H, a charged substituent or an ionizable group;
$R_9$, $R_{10}$, $R_{11}$, $R_{12}$, and $R_{13}$, for each occurrence, are independently H or an optionally substituted alkyl; and
q and r, for each occurrence, are independently an integer between 0 and 10. The remaining variables in formula (I) or formula (II) are as described above in the first embodiment, the $1^{st}$, $2^{nd}$ or $3^{rd}$ embodiment or any more specific embodiments described therein.

In a specific embodiment, q and r, are independently an integer from 1 to 6, more specifically, 1 to 3.

In another specific embodiment, $R_9$, $R_{10}$, $R_{11}$, $R_{12}$, and $R_{13}$, for each occurrence, are independently H or a $C_{1-3}$alkyl. More specifically, $R_9$, $R_{10}$, $R_{11}$, $R_{12}$, and $R_{13}$ are all H.

In another specific embodiment, p is an integer from 2 to 14. More specifically, p is an integer from 2 to 8, 2 to 6 or 2 to 4.

In a specific embodiment, E is $-(CR_{10}R_{11})_q-$; and the remaining variables in formula (L1) are as described above in the $4^{th}$ embodiment.

In another specific embodiment, E is

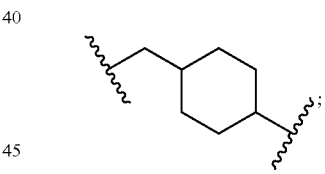

and the remaining variables in formula (L) are as described above in the $4^{th}$ embodiment.

In yet another specific embodiment, Z is $-C(=O)-NR_9-$ or $-NR_9-C(=O)-$; and the remaining variables in formula (L) are as described above in the $4^{th}$ embodiment or any more specific embodiments described above. Even more specifically, $R_9$ is H or Me. Alternatively, $R_9$ is H.

In yet another specific embodiment, Q is i) H; ii) $-SO_3H$, $-Z'-SO_3H$, $-OPO_3H_2$, $-Z'-OPO_3H_2$, $-PO_3H_2$, $-Z'-PO_3H_2$, $-CO_2H$, $-Z'-CO_2H$, $-NR_{14}R_{15}$, or $-Z'-NR_{14}R_{15}$, or a pharmaceutically acceptable salt thereof; or, iii) $-N^+R_{14}R_{15}R_{16}X^-$ or $-Z'-N^+R_{14}R_{15}R_{16}X^-$; Z' is an optionally substituted alkylene, an optionally substituted cycloalkylene or an optionally substituted phenylene; $R_{14}$ to $R_{16}$ are each independently an optionally substituted alkyl; and $X^-$ is a pharmaceutically acceptable anion; and the remaining variables in formula (L) are as described above in the $4^{th}$ specific embodiment or any more specific embodiments described above. In one embodiment, Z' is an optionally substituted alkylene. In yet another embodiment, Z' is a $C_{1-3}$alkylene (e.g., —CH$_2$); and $R_{14}$ to $R_{16}$ are each independently a $C_{1-4}$alkyl.

In yet another specific embodiment, Q is H, or —SO$_3$M, wherein M is a pharmaceutically acceptable cation (e.g., H$^+$, Na$^+$ or K$^+$); and the remaining variables in formula (L1) are as described above in the 4$^{th}$ embodiment or any more specific embodiments described above.

In a 5$^{th}$ embodiment, for conjugates of formula (I) of the first aspect of the invention, -J$_{CB}$'-L- is represented by any one of the following structural formulae:

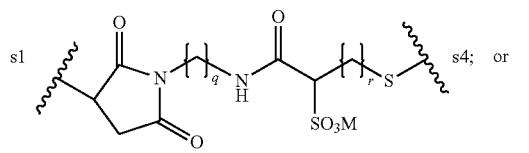
(L1a)

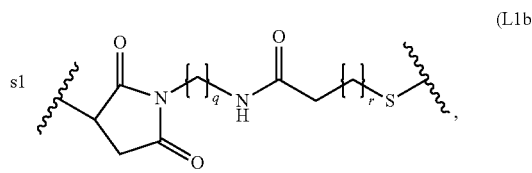
(L1b)

wherein q and r are each independently an integer from 1 to 6; M is a pharmaceutically acceptable cation; and the remaining variables are as describe above for formula (I). More specifically, q and r are each independently an integer from 1 to 3. In another more specific embodiment, M is H$^+$, Na$^+$ or K$^+$.

Also, in the 5$^{th}$ embodiment, for compounds of formula (II) in the second aspect of the invention, J$_{CB}$-L- is represented by any one of the following structural formulae:

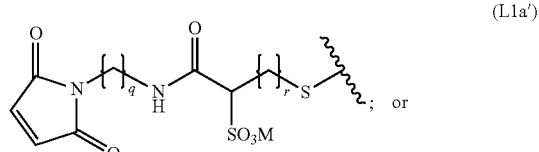
(L1a')

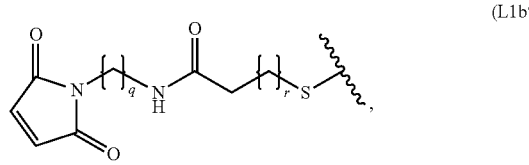
(L1b')

wherein q and r are each independently an integer from 1 to 6; M is a pharmaceutically acceptable cation; and the remaining variables are as describe above for formula (II). More specifically, q and r are each independently an integer from 1 to 3. In another more specific embodiment, M is H$^+$, Na$^+$ or K$^+$.

In a 6$^{th}$ embodiment, for conjugates of formula (I) in the first aspect, -J$_{CB}$'-L- is represented by any one of the following structural formulae:

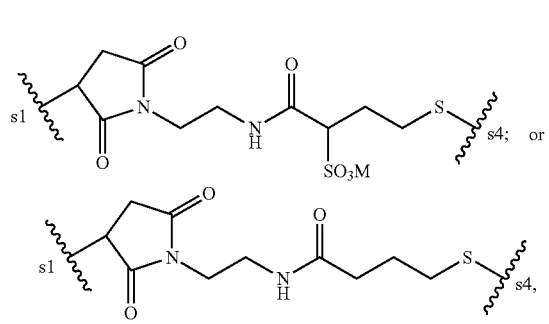

wherein M is a pharmaceutically acceptable cation and the remaining variables are as describe above for formula (I). More specifically, M is H$^+$, Na$^+$ or K$^+$.

Also in the 6$^{th}$ embodiment, for compounds of formula (I) in the second aspect, J$_{CB}$-L- is represented by any one of the following structural formulae:

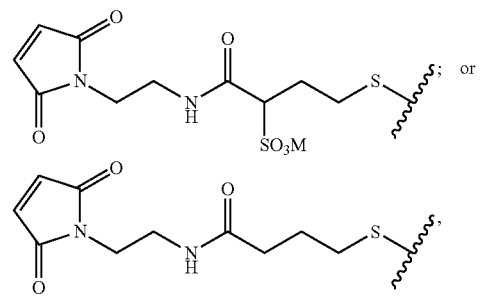

wherein M is a pharmaceutically acceptable cation, and the remaining variables are as describe above for formula (II). More specifically, M is H$^+$, Na$^+$ or K$^+$.

In a 7$^{th}$ specific embodiment, for conjugates of formula (I) in the first aspect and compounds of formula (II) in the second aspect, -L- is represented by the following structural formula:

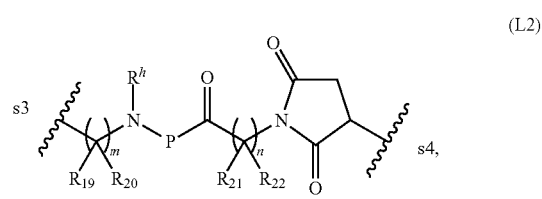
(L2)

wherein:
s3 is the site covalently linked to the J$_{CB}$' group and s4 is the site covalently linked to the group D;
$R_{19}$ to $R_{22}$, for each occurrence, are independently H or an optionally substituted alkyl;
m and n are each independently an integer between 0 and 10;
$R^h$ is H or an optionally substituted alkyl;
P is an optionally substituted alkylene, —(CH$_2$—CH$_2$—O)$_j$—, —(O—CH$_2$—CH$_2$)$_j$—, an amino acid residue or a peptide containing 2-20 amino acid residues; and
j is an integer from 1 to 24;
and the remaining variables are as described above for formula (I) or formula (II), the 1$^{st}$ 2$^{nd}$ or 3$^{rd}$ embodiment, or any more specific embodiments described therein.

In a 8th embodiment, for formula (L2), $R_{19}$, $R_{20}$, $R_{21}$ and $R_{22}$ are each H or a $C_{1-3}$alkyl; m and n are each independently an integer between 1 and 6; and the remaining variables are as described above in the $7^{th}$ embodiment. More specifically, $R_{19}$, $R_{20}$, $R_{21}$ and $R_{22}$ are all H. Even more specifically, $R_{19}$, $R_{20}$, $R_{21}$ and $R_{22}$ are all H; and m and n are each independently an integer between 1 and 3.

In $9^{th}$ specific embodiment, for formula (L2), P is an amino acid residue or a peptide containing 2 to 10 amino acid residues; and the remaining variables are as described above in the $7^{th}$ or $8^{th}$ embodiment. More specifically, P is a peptide containing 2 to 5 amino acid residues.

In one embodiment, each amino acid residue is the residue of an amino acid independently selected from: a naturally occurring amino acid, a synthetic amino acid, an amino acid analog, and an amino acid mimetic that functions in a manner similar to the naturally occurring amino acids.

In another embodiment, each amino acid residue is the residue of an amino acid independently selected from the group consisting of: Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Proline, Serine, Tyrosine, N-methyl-Histidine, N-methyl-Alanine, N-methyl-Isoleucine, N-methyl-Arginine, N-methyl-Leucine, N-methyl-Asparagine, N-methyl-Lysine, N-methyl-Aspartic acid, N-methyl-Methionine, N-methyl-Cysteine, N-methyl-Phenylalanine, N-methyl-Glutamic acid, N-methyl-Threonine, N-methyl-Glutamine, N-methyl-Tryptophan, N-methyl-Glycine, N-methyl-Valine, N-methyl-Proline, N-methyl-Serine, N-methyl-Tyrosine, hydroxyproline, γ-carboxyglutamate, selinocysteine, O-phosphoserine, homoserine, norleucine, methionine sulfoxide, methionine methyl sulfonium, citrulline, Ornithine, cysteine sulfonic acid, cysteine sulfinic acid, 3-aminoalanine, 3-dimethylaminoalanine, 2-amino-4-(dimethylamino)butanoic acid, 2,4-diaminobutanoic acid, 2-amino-6-(dimethylamino)hexanoic acid, 2-amino-5-(dimethylamino)pentanoic acid, and 3-alanine, each independently as an L or D isomer. More specifically, each amino acid residue is the residue of an independently selected glycine or alanine.

In another embodiment, P is a peptide cleavable by a protease. More specifically, P is a peptide cleavable by a protease expressed in tumor tissue. Alternatively, P is a peptide cleavable by a lysosomal protease.

In yet another embodiment, P is selected from the group consisting of: Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 14), β-Ala-Leu-Ala-Leu (SEQ ID NO: 15), Gly-Phe-Leu-Gly (SEQ ID NO: 16), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, and D-Ala-D-Ala., Gly-Gly-Gly, Ala-Ala-Ala, D-Ala-Ala-Ala, Ala-D-Ala-Ala, Ala-Ala-D-Ala, Ala-Val-Cit, Ala-Val-Ala, and β-Ala-Gly-Gly-Gly. More specifically, P is Gly-Gly-Gly, Ala-Ala-Ala, D-Ala-Ala-Ala, Ala-D-Ala-Ala, Ala-Val-Ala, or β-Ala-Gly-Gly-Gly.

In a $10^{th}$ embodiment, for conjugates of formula (I) in the first aspect, -J$_{CB}$'-L- is represented by the following structural formula:

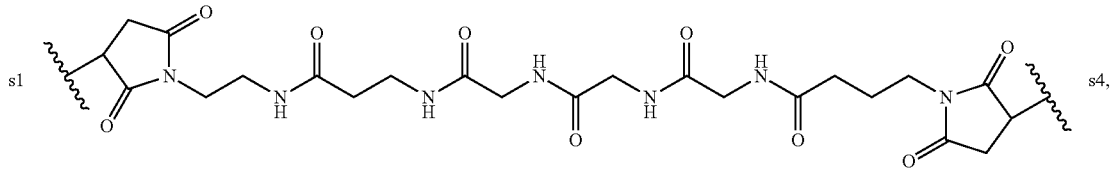 [SMILES: *C1CC(=O)N(CCCC(=O)NCC(=O)NCC(=O)NCC(=O)NCCC(=O)NCCN2C(=O)CC(*)C2=O)C1=O]

and the remaining variables are as described above for formula (I).

Also in the $10^{th}$ embodiment, for compounds of formula (II) in the second aspect, J$_{CB}$-L- is represented by the following structural formula:

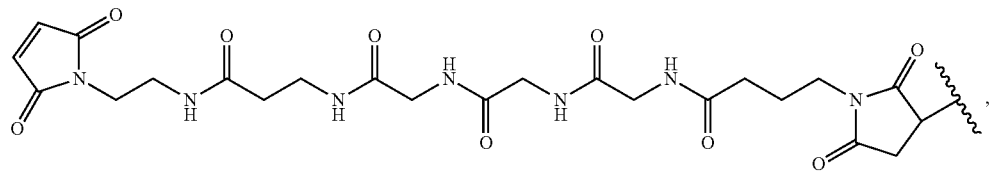 [SMILES: *C1CC(=O)N(CCCC(=O)NCC(=O)NCC(=O)NCC(=O)NCCC(=O)NCCN2C(=O)C=CC2=O)C1=O]

and the remaining variables are as described above for formula (II).

In a $11^{th}$ embodiment, for conjugates of formula (I) and compounds of formula (II), -L- is represented by the following structural formula:

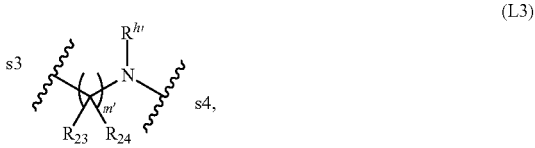

(L3)

wherein:

s3 is the site covalently linked to J$_{CB}$', and s4 is the site covalently linked to D;

$R_{23}$ and $R_{24}$, for each occurrence, are independently H or an optionally substituted alkyl;

m' is an integer between 0 and 10; and $R^{h'}$ is H or an optionally substituted alkyl;

and the remaining variables are as described above for formula (I) or formula (II), the $1^{st}$, $2^{nd}$ or $3^{rd}$ embodiment, or any specific embodiments described therein.

In a specific embodiment, m' is an integer from 1 to 6. Even more specifically, m' is an integer from 1 to 3.

In another specific embodiment, $R_{23}$ and $R_{24}$, for each occurrence, are independently H or a $C_{1-3}$alkyl. Even more specifically, $R_{23}$ and $R_{24}$ are both H.

In another specific embodiment, $R^{h''}$ is H or a $C_{1-3}$alkyl. More specifically, $R^{h''}$ is H.

In another specific embodiment, $R_{23}$ and $R_{24}$ are both H; m' is an integer from 1 to 6. Even more specifically, m' is an integer from 1 to 3.

In a 12$^{th}$ embodiment, for conjugates of formula (I) in the first aspect, -$J_{CB}$'-L- is represented by the following structural formula:

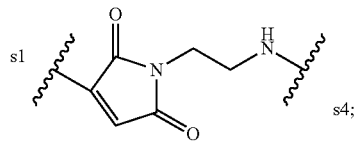 [SMILES: *NCCN1C(=O)C=C(*)C1=O]

and the remaining variables are as described above for formula (I).

Also in the 12$^{th}$ embodiment, for compounds of formula (II) in the second aspect, $J_{CB}$-L- is represented by the following structural formula:

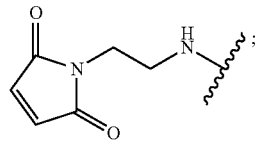 [SMILES: *NCCN1C(=O)C=CC1=O]

and the remaining variables are as described above for formula (II).

In another embodiment, for conjugates of formula (I) or compounds of formula (II), the cytotoxic agent represented by D is a maytansinoid; and the remaining variables are as described for formula (I) or (II), any one of the 1$^{st}$-12$^{th}$ embodiments described above, or any more specific embodiments described therein.

In another embodiment, for conjugates of formula (I) or compounds of formula (II), the cytotoxic agent represented by D is a benzodiazepine; and the remaining variables are as described for formula (I) or (II), any one of the 1$^{st}$-12$^{th}$ embodiments described above, or any more specific embodiments described therein.

In a 13$^{th}$ embodiment, for conjugates of formula (I) or compounds of formula (II), D is a maytansinoid represented by the following structural formula:

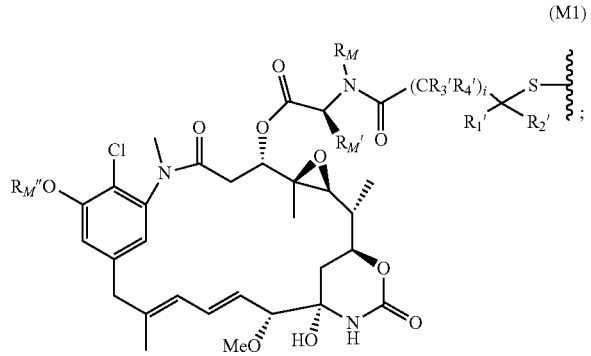

wherein:
$R_M$, $R_M'$, and $R_M''$, for each occurrence, are independently H or an optionally substituted alkyl;
$R_1'$, $R_2'$, $R_3'$ and $R_4'$ for each occurrence, are independently H, an optionally substituted an optionally substituted alkyl, an optionally substituted alkenyl, an optionally substituted cycloalkyl, an optionally substituted heterocyclyl, an optionally substituted aryl, or an optionally substituted heteroaryl; and
i is an integer between 0 and 15;
and the remaining variables are as described above for formula (I) or (II), any one of the 1$^{st}$-10$^{th}$embodiments described above or any specific embodiments described therein.

More specifically, D is represented by the following structural formula:

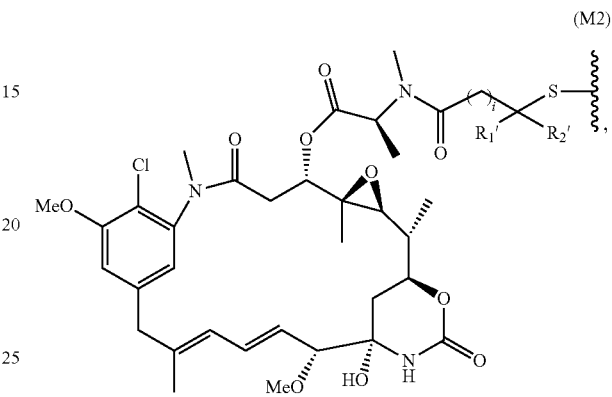

wherein i is 1 or 2; and $R_1'$ and $R_2'$ are each independently H or $C_{1-3}$alkyl; and the remaining variables are as described in the 13$^{th}$ embodiment.

In a 14$^{th}$ specific embodiment, for conjugates of formula (I) or compounds of formula (II), D is a maytansinoid represented by the following structural formula:

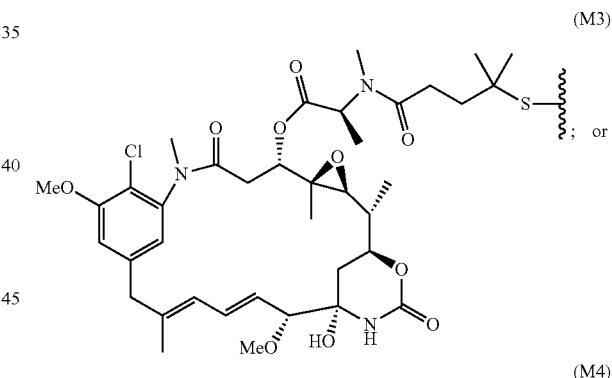

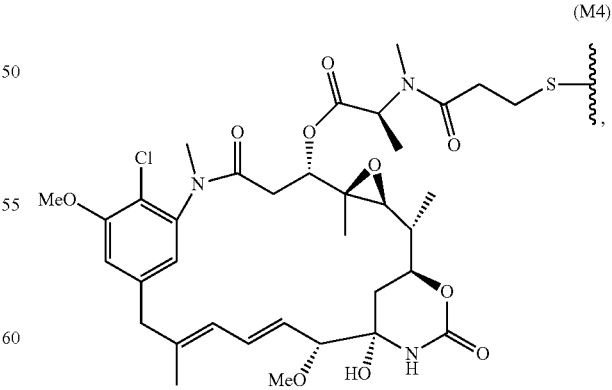

and the remaining variables are as described above for formula (I) or (II), any one of the 1$^{st}$-10$^{th}$embodiments describe above or any specific embodiments described therein.

In a 15th embodiment, for conjugates of formula (I) or compounds of formula (II), D is represented by the following structural formula:
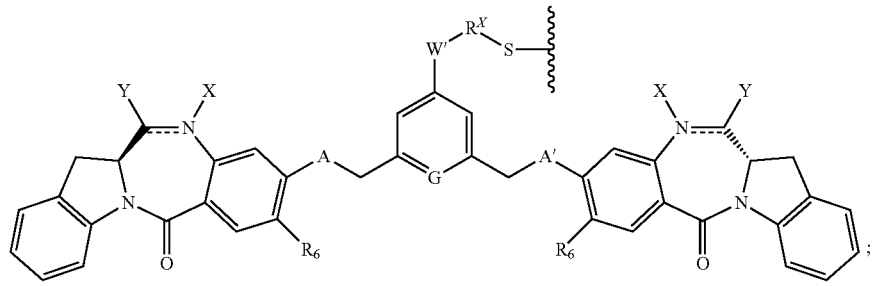
(IBD1)
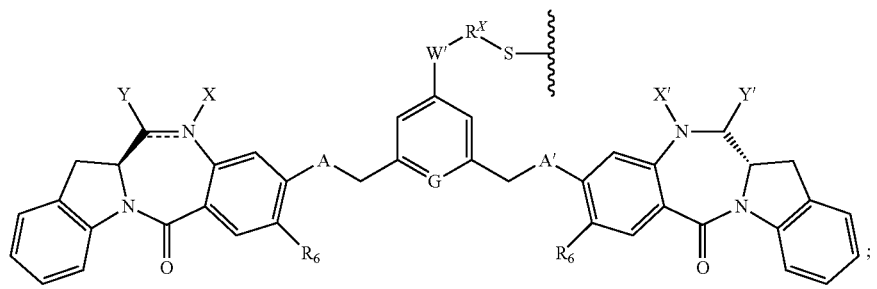
(IBD2)
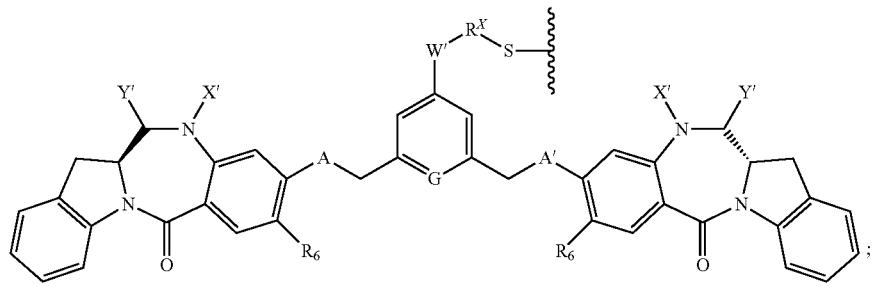
(IBD3)
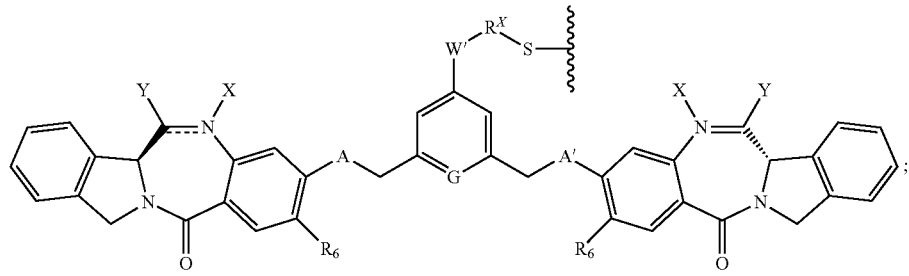
(IBD4)
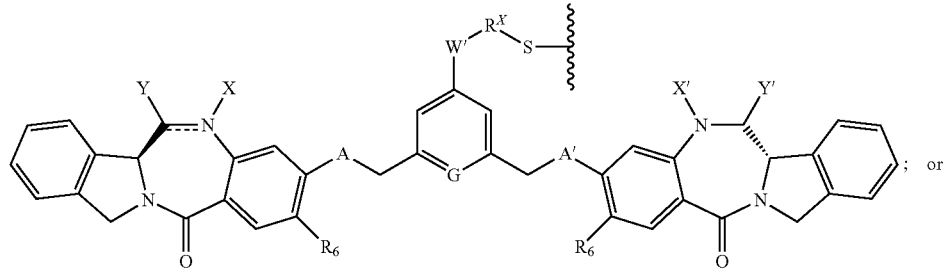
(IBD5)
; or -continued (IBD6)

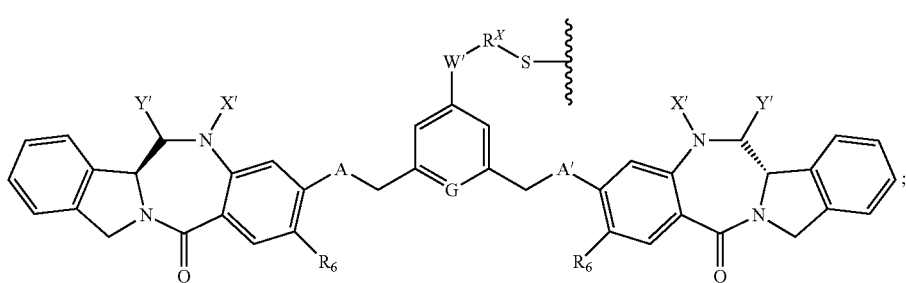

or a pharmaceutically acceptable salt thereof, wherein:

the double line == between N and C represents a single bond or a double bond, provided that when it is a double bond, X is absent and Y is —H, and when it is a single bond, X is selected from —H, or an amine protecting group (preferably X is —H); and Y is selected from —OR, —OCOR', —SR, —NR'R", —SO$_3$M, —SO$_2$M or —OSO$_3$M, wherein M is —H or a cation (such as Na$^+$ or K$^+$);

R is —H, an optionally substituted linear, branched or cyclic alkyl, alkenyl or alkynyl having from 1 to 10 carbon atoms or a PEG group —(CH$_2$CH$_2$O)$_n$—R$^c$, wherein n is an integer from 1 to 24, and R$^c$ is a linear or branched alkyl having 1 to 4 carbon atoms;

R' and R" are each independently selected from —H, —OH, —OR, —NRR', —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—R$^c$, and R$^{g'}$ is —H, an optionally substituted linear, branched or cyclic alkyl, alkenyl or alkynyl having from 1 to 10 carbon atoms or a PEG group —(CH$_2$CH$_2$O)$_n$—R$^c$;

X' is selected from the group consisting of —H, —OH, a substituted or unsubstituted linear, branched or cyclic alkyl, alkenyl or alkynyl having from 1 to 10 carbon atoms, phenyl, and an amine-protecting group;

Y' is selected from the group consisting of —H, an oxo group, a substituted or unsubstituted linear, branched or cyclic alkyl, alkenyl or alkynyl having from 1 to 10 carbon atoms;

A and A' are selected from —O— and —S—;

W' is absent, or selected from —O—, —N(R$^e$)—, —N(R$^e$)—C(═O)—, —N(C(═O)R$^e$)—, —S— or —CH$_2$—S—, —CH$_2$NR$^e$—;

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

G is selected from —CH— or —N—; and

R$_6$ is —H, —R, —OR, —SR, —NR'R", —NO$_2$, or halogen;

and the remaining variables are as described above for formula (I) or (II), any one of the 1$^{st}$-10$^{th}$ embodiments or any specific embodiments described therein.

In a specific embodiment, D is represented by formula (IBD1) above, or a pharmaceutically acceptable salt thereof.

In another specific embodiment, for formulas (IBD1)-(IBD6):

the double line == between N and C represents a single bond or a double bond, provided that when it is a double bond, X is absent and Y is —H, and when it is a single bond, X is —H, and Y is —OH or —SO$_3$M;

M is —H or a pharmaceutically acceptable cation (e.g., Na$^+$);

X' and Y' are both —H;

A and A' are both —O—;

R$_6$ is —OMe; and

R$^x$ is a linear or branched alkyl having 1 to 6 carbon atoms.

In a 16$^{th}$ embodiment, for conjugates of formula (I) or compounds of formula (II), D is represented by the following structural formula:

(IBD7)

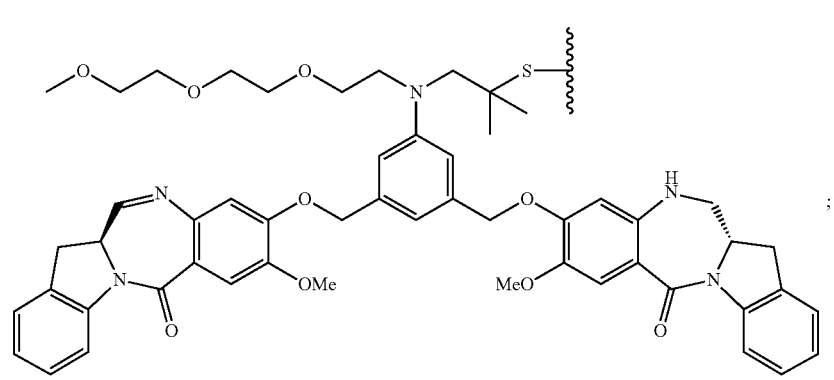

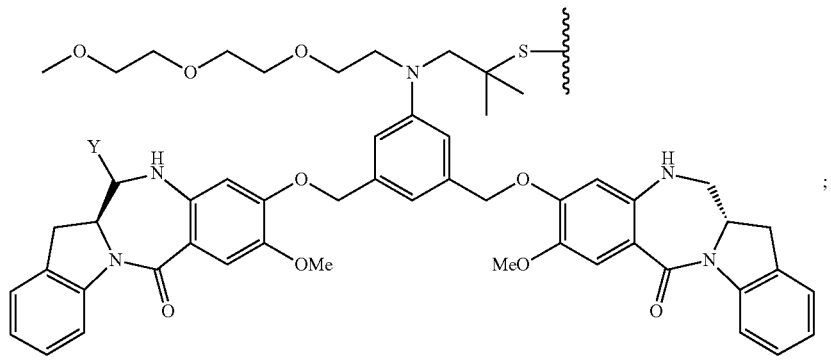
(IBD8)
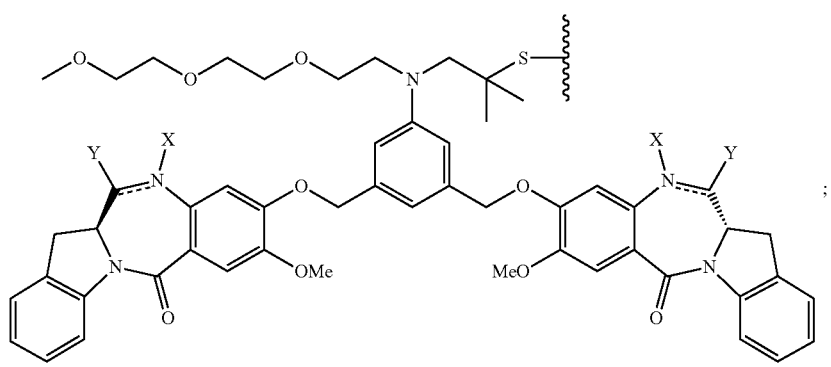
(IBD7a)
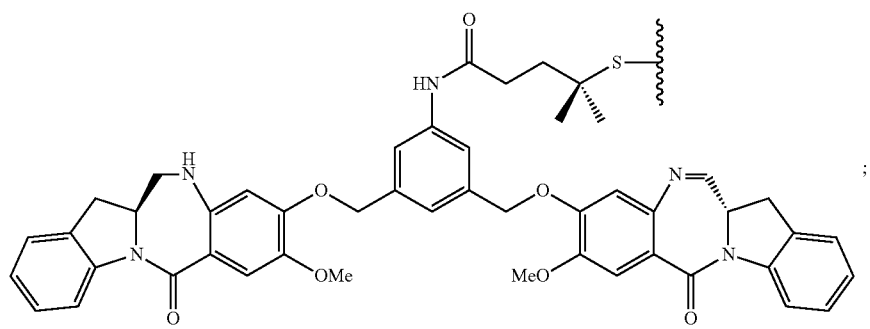
(IBD9)
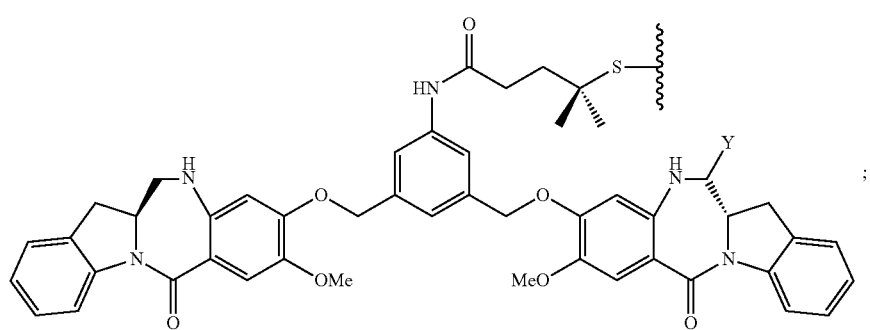
(IBD10)

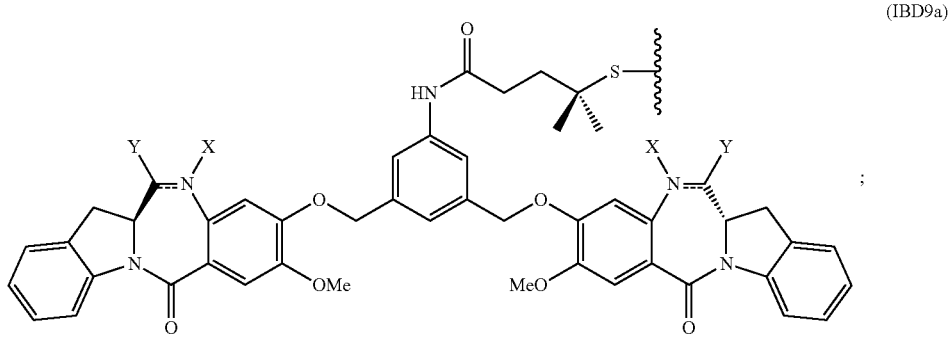

(IBD9a)

or a pharmaceutically acceptable salt thereof, wherein the double line ═ between N and C represents a single bond or a double bond, provided that when it is a double bond, X is absent and Y is —H, and when it is a single bond, X is —H, and Y is —OH or —SO$_3$M; and the remaining variables are as described above for formula (I) or (II), any one of the 1$^{st}$-10$^{th}$ embodiments or any specific embodiments described therein.

In a specific embodiment, for formulas (IBD7)-(IBD10) and (IBD7a) and (IBD9a), above, Y is —SO$_3$M, and M is H$^+$, Na$^+$ or K$^+$.

In a 17$^{th}$ embodiment, for conjugates of formula (I) or compounds of formula (II), D is represented by the following structural formula:

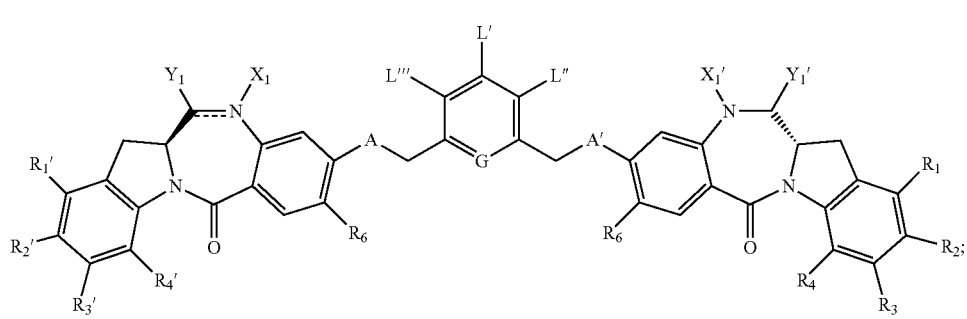

(IBD11)

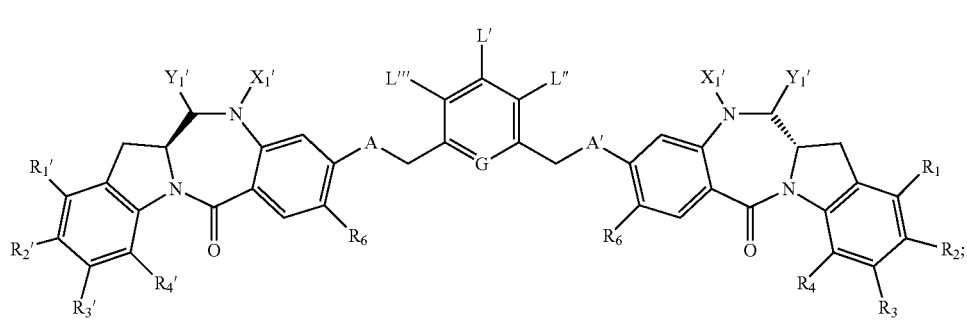

(IBD12)

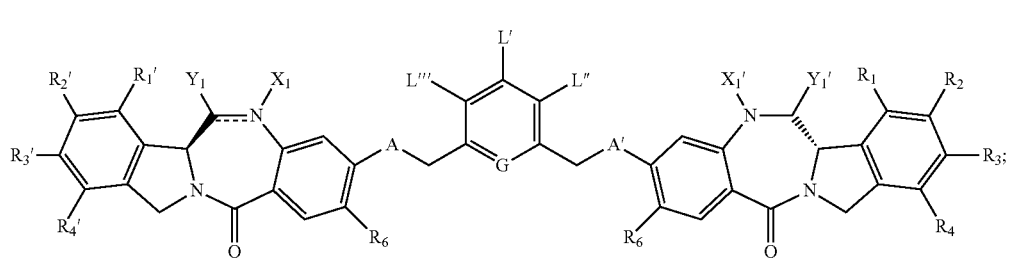

(IBD13)

-continued

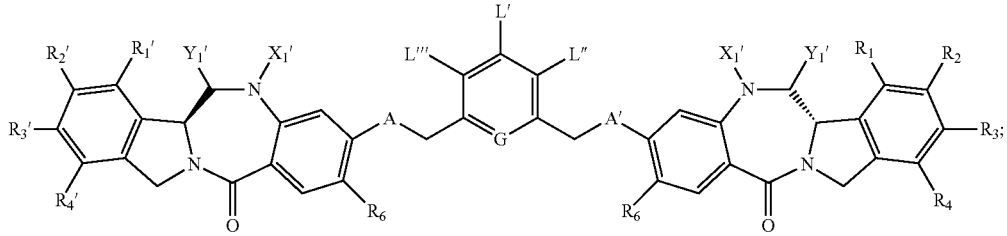

(IBD14)

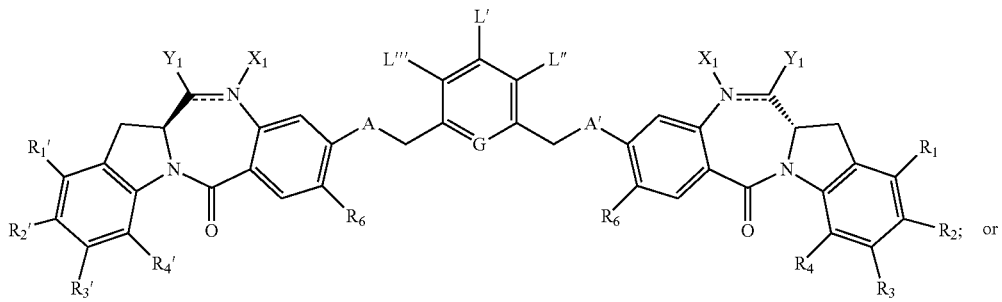

(IBD15)

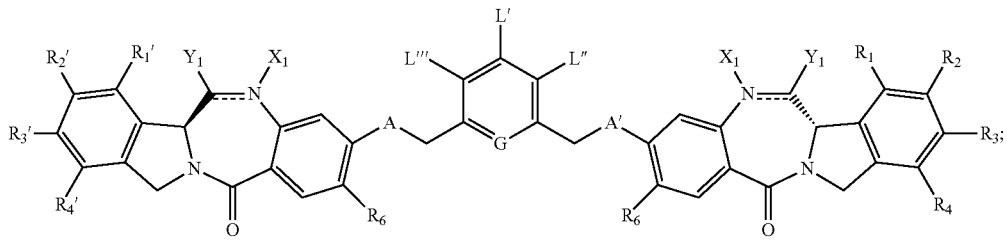

(IBD16)

or a pharmaceutically acceptable salt thereof, wherein:

one of L', L", and L'" is represented by the following formula:

 (A'), or

 (D');

and the other two are each independently selected from —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, halogen, guanidinium [—NH(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

one of the Z$_1$ and Z$_2$ is —C(=O)—, and the other is —NR$_5$—;

P$_1$ is an amino acid residue or a peptide containing between 2 to 20 amino acid residues;

R$_{x1}$ is an optionally substituted linear, branched or cyclic alkyl, alkenyl or alkynyl having from 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

the double line $=\!=$ between N and C represents a single bond or a double bond, provided that when it is a double bond X$_1$ is absent and Y$_1$ is —H, or a linear or branched alkyl having 1 to 4 carbon atoms, and when it is a single bond, X$_1$ is —H or an amine protecting moiety; and Y$_1$ is a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc. attached through the nitrogen atom), a guanidinium represented by —NR'(C=NH)NR'R", an amino acid, or a peptide represented by —NRCOP', —SR, —SOR', halogen, cyano, azido, —OSO$_3$H (or a salt thereof), sulfite (—SO$_3$H or —SO$_2$H or a salt thereof), metabisulfite (H$_2$S$_2$O$_5$ or a salt thereof), mono-, di-, tri-, and tetra-thiophosphate (PO$_3$SH$_3$, PO$_2$S2H$_2$, POS$_3$H$_2$, PS$_4$H$_2$ or a salt thereof), thio phosphate ester (R$^i$O)$_2$PS(OR$^i$), R'S—, R$^i$SO, R$^i$SO$_2$, R$^i$SO$_3$, thiosulfate (HS$_2$O$_3$ or a salt thereof), dithionite (HS$_2$O$_4$ or salt thereof), phosphorodithioate (P(=S)(OR$^{k'}$)(S)(OH) or a salt thereof), hydroxamic acid (R$^{k'}$C(=O)NOH or a salt thereof), and formaldehyde sulfoxylate (HOCH$_2$SO$_2$— or a salt thereof) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

P' is an amino acid residue or a peptide containing between 2 to 20 amino acid residues, R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or an optionally substituted linear or branched alkyl having 1 to 4 carbon atoms;

n is an integer from 1 to 24;

X$_1$' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y$_1$' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, halogen, guanidinium [—NH(C=NH)NH$_2$], —OR, —NR'R", —NO$_2$, —NCO, —NR'COR", —SR, —SOR', —SO$_2$R', —SO$_3$—H, —OSO$_3$H, —SO$_2$NR'R", cyano, an azido, —COR', —OCOR', and —OCONR'R";

R$_6$ is —H, —R, —OR, —SR, —NR'R", —NO$_2$, or halogen;

G is —CH— or —N—;

A and A' are the same or different, and are independently selected from —O—, oxo (—C(=O)—), —CRR'O—, —CRR'—, —S—, —CRR'S—, —NR$_5$ and —CRR'N (R$_5$)—; and R$_5$ for each occurrence is independently —H or an optionally substituted linear or branched alkyl having 1 to 10 carbon atoms;

and the remaining variables are as described for formula (I) or (II), the 1$^{st}$, 2$^{nd}$, 3$^{rd}$, 11$^{th}$ or 12$^{th}$ specific embodiment or any more specific embodiments described therein.

In a more specific embodiment, D is represented by formula (IBD11).

In another more specific embodiment, for formulas (IBD11)-(IBD16), one of L', L" and L'" is represented by formula (A') or (D'), and the others are —H, an linear or branched alkyl having from 1 to 6 carbon atoms, halogen, —OH, (C$_1$-C$_6$)alkoxy, or —NO$_2$.

In another more specific embodiment, for formulas (IBD11)-(IBD16), L' is represented by formula (A'); and L" and L'" are both —H.

In another more specific embodiment, for formulas (IBD11)-(IBD16), L' is represented by formula (D'); and L" and L'" are both —H.

In another more specific embodiment, for formulas (IBD11)-(IBD16), R$_{x1}$ is a linear, branched or cyclic alkyl having 1 to 6 carbon atoms optionally substituted with halogen, —OH, —SO$_3$H, (C$_1$-C$_3$)alkyl, (C$_1$-C$_3$)alkoxy, halo(C$_1$-C$_3$)alkyl, or a charged substituent or an ionizable group Q.

In a 18th specific embodiment, for formulas (IBD11)-(IBD16), L' is represented by the following formula:

$$-NR_5-P_1-C(=O)-(CR_aR_b)_s-C(=O)- \quad (B1');$$

$$-NR_5-P_1-C(=O)-Cy-(CR_aR_b)_{s1'}-C(=O)- \quad (B2');$$

$$-C(=O)-P_1-NR_5-(CR_aR_b)_s-C(=O)- \quad (C1'), \text{ or}$$

$$-C(=O)-P_1-NR_5-Cy-(CR_aR_b)_{s1'}-C(=O)- \quad (C2')$$

wherein:

R$_a$ and R$_b$, for each occurrence, are each independently —H, (C$_1$-C$_3$)alkyl or a charged substituent or an ionizable group Q;

s is an integer from 1 to 6;

s1' is 0 or an integer from 1 to 6; and

Cy is a cyclic alkyl having 5 or 6 ring carbon atoms optionally substituted with halogen, —OH, (C$_1$-C$_3$)alkyl, (C$_1$-C$_3$)alkoxy, or halo(C$_1$-C$_3$)alkyl;

and the remaining variables are as described above in the 17$^{th}$ specific embodiment or any more specific embodiments described therein.

In a more specific embodiment, R$_a$ and R$_b$ are both H; Cy in formulas (B2') and (C2') is cyclohexane; and R$_5$ is H or Me. Even more specifically, s1' is 0 or 1.

In a 19th embodiment, for formulas (IBD11)-(IBD16), P$_1$ is a peptide containing 2 to 10 amino acid residues; and the remaining variables are as described in the 17$^{th}$ or 18$^{th}$ specific embodiment.

In a specific embodiment, P$_1$ is a peptide containing 2 to 5 amino acid residues.

In another specific embodiment, P$_1$ is Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 14), β-Ala-Leu-Ala-Leu (SEQ ID NO: 15), Gly-Phe-Leu-Gly (SEQ ID NO: 16), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, or Met-Ala. Even more specifically, P is Gly-Gly-Gly, Ala-Val, Ala-Ala, Ala-D-Ala, D-Ala-Ala, or D-Ala-D-Ala.

In a 20$^{th}$ embodiment, for formulas (IBD11)-(IBD16), the double line == between N and C represents a double bond; and the remaining variables are as described above in the 17$^{th}$, 18$^{th}$ or 19$^{th}$ embodiment.

In a 21$^{st}$ embodiment, for formulas (IBD11)-(IBD16), the double line == between N and C represents a single bond, X$_1$ is —H or an amine protecting group; and Y$_1$ is —OR, —OCOR', —SR, —NR'R," an optionally substituted 5- or 6-membered nitrogen-containing heterocycle, —SO$_3$M, —SO$_2$M and —OSO$_3$M, wherein M is H$^+$ or a pharmaceutically acceptable cation; and the remaining variables are as described above in the 17th, 18th or 19th embodiment. Specifically, $Y_1$ is selected from —SO$_3$M, —OH, —OMe, —OEt or —NHOH. More specifically, $Y_1$ is —SO$_3$M or —OH, wherein M is H$^+$, Na$^+$ or K$^+$.

In certain embodiments, formulas (IBD11)-(IBD16), $X_1'$ is selected from the group consisting of —H, —OH, an optionally substituted linear, branched or cyclic alkyl, alkenyl or alkynyl having from 1 to 10 carbon atoms, and phenyl; and the remaining variables are as described above in the 17th, 18th, 19th, 20th or 21st specific embodiment. More specifically, $X_1'$ is —H, —OH, (C$_1$-C$_3$)alkyl, halo(C$_1$-C$_3$)alkyl, or phenyl. In another more specific embodiment, $X_1'$ is —H, —OH or -Me. Even more specifically, $X_1'$ is —H.

In certain embodiments, for formulas (IBD11)-(IBD16), $Y_1'$ is selected from the group consisting of —H, an oxo group, an optionally substituted linear, branched or cyclic alkyl, alkenyl or alkynyl having from 1 to 10 carbon atoms; and the remaining variables are as described above in the 17th, 18th, 19th, 20th or 21st specific embodiment. More specifically, $Y_1'$ is —H, an oxo group, (C$_1$-C$_3$)alkyl or halo(C$_1$-C$_3$)alkyl. In another more specific embodiment, $Y_1'$ is —H or oxo. Even more specifically, $Y_1'$ is —H.

In certain embodiments, for formulas (IBD11)-(IBD16), A and A' are the same or different, and are —O—, —S—, —NR$_5$—, or oxo —(C=O)—; and the remaining variables are as described above in the 17th, 18th, 19th, 20th or 21st specific embodiment. More specifically, A and A' are the same or different, and are —O— or —S—. Even more specifically, A and A' are —O—.

In certain embodiments, for formulas (IBD11)-(IBD16), $R_6$ is —OMe; and the remaining variables are as described above in the 17th, 18th, 19th, 20th or 21st embodiment.

In certain embodiments, for formulas (IBD11)-(IBD16), $R_1$, $R_2$, $R_3$, $R_4$, $R_1'$, $R_2'$, $R_3'$ and $R_4'$ are each independently —H, halogen, —NO$_2$, —OH, (C$_1$-C$_3$)alkyl, halo(C$_1$-C$_3$)alkyl or (C$_1$-C$_3$)alkoxy; and the remaining variables are s described. More specifically, $R_1$, $R_2$, $R_3$, $R_4$, $R_1'$, $R_2'$, $R_3'$ and $R_4'$ are all —H.

In certain embodiments, for formulas (IBD11)-(IBD16), R, R', R" and $R_5$ are each independently —H or (C$_1$-C$_3$) alkyl; and the remaining variables are as described above in the 17th, 18th, 19th, 20th or 21st embodiment.

In a 22nd embodiment, for formulas (IBD11)-(IBD16):
the double line == between N and C represents a single bond or double bond, provided that when it is a double bond, $X_1$ is absent and $Y_1$ is —H; and when it is a single bond, $X_1$ is —H, and $Y_1$ is —OH or —SO$_3$M;
$R_1$, $R_2$, $R_3$, $R_4$, $R_1'$, $R_2'$, $R_3'$ and $R_4'$ are all —H;
$R_6$ is —OMe;
$X_1'$ and $Y_1'$ are both —H;
A and A' are —O—; and
M is H$^+$, Na$^+$ or K$^+$; and the remaining variables are as described above in the 17th, 18th, 19th, 20th or 21st specific embodiment. More specifically, R, R', R" and $R_5$ are each independently —H or (C$_1$-C$_3$)alkyl. Even more specifically, R, R', R" and $R_5$ are all —H.

In a 23rd embodiment, for conjugates of formula (I) or compounds of formula (II), D is represented by the following structural formula:

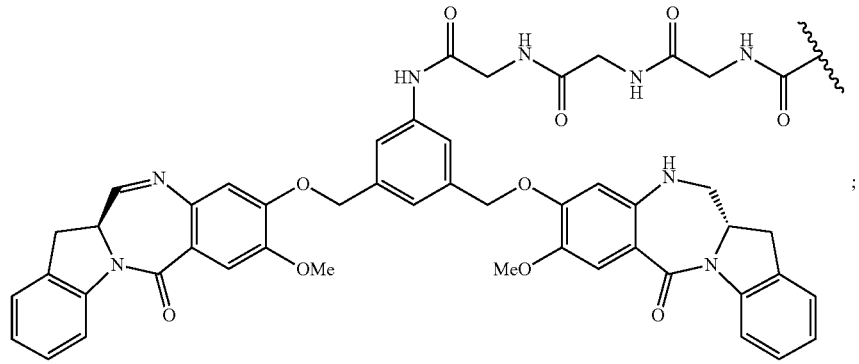

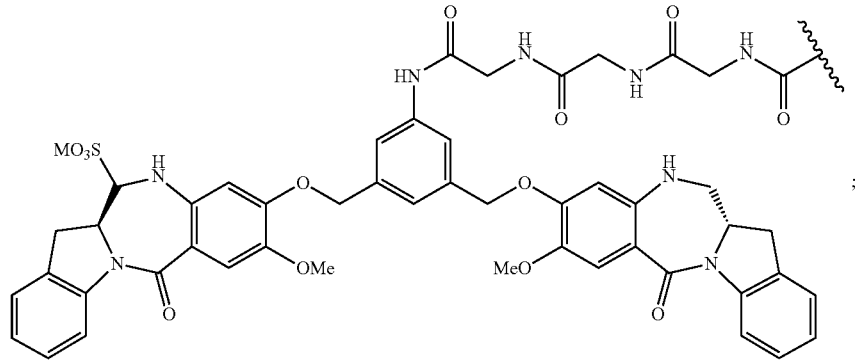

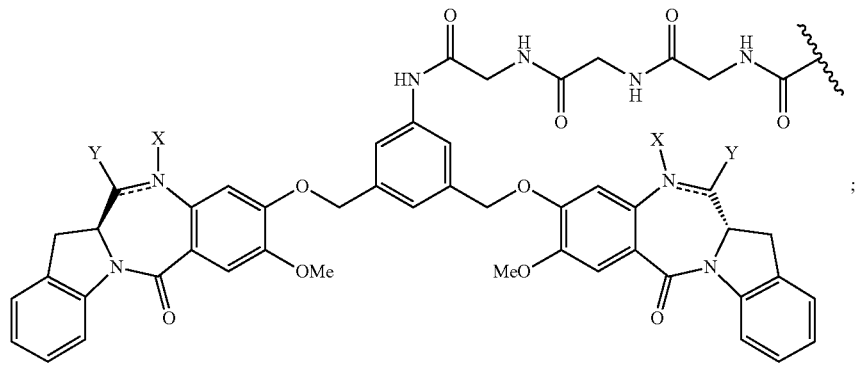
;
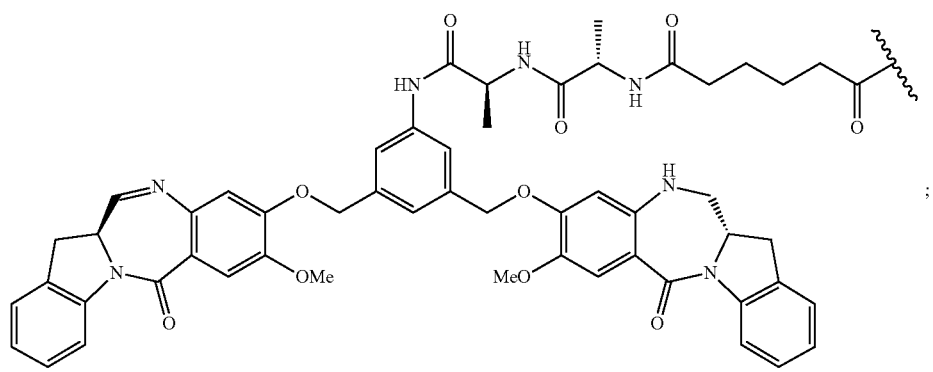
;
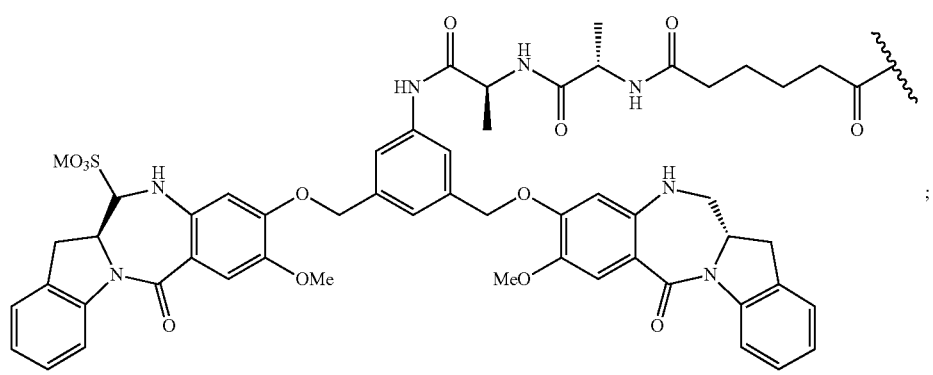
;
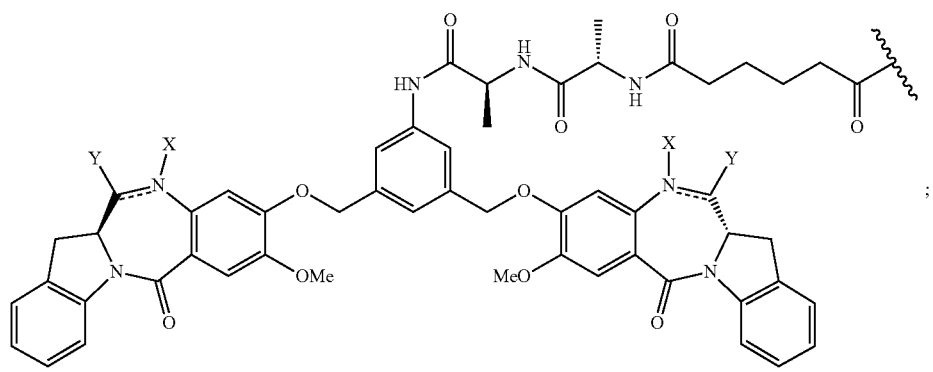
;

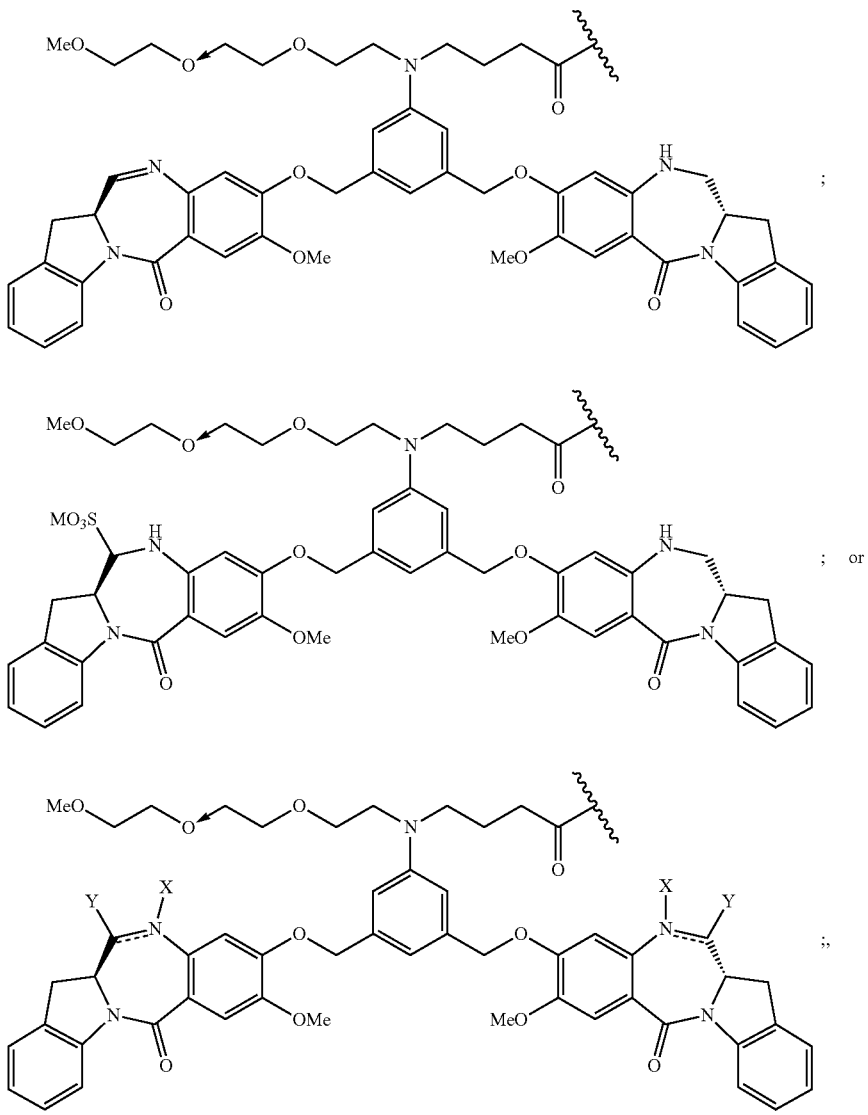

wherein the double line ⚌ between N and C represents a single bond or a double bond, provided that when it is a double bond, X is absent and Y is —H, and when it is a single bond, X is —H, and Y is —SO₃M; M is H⁺ or a pharmaceutically acceptable cation; and the remaining variables are as described above in the 17th embodiment.

In a 24th embodiment, for conjugates of formula (I), the conjugate is represented by the following structural formula:

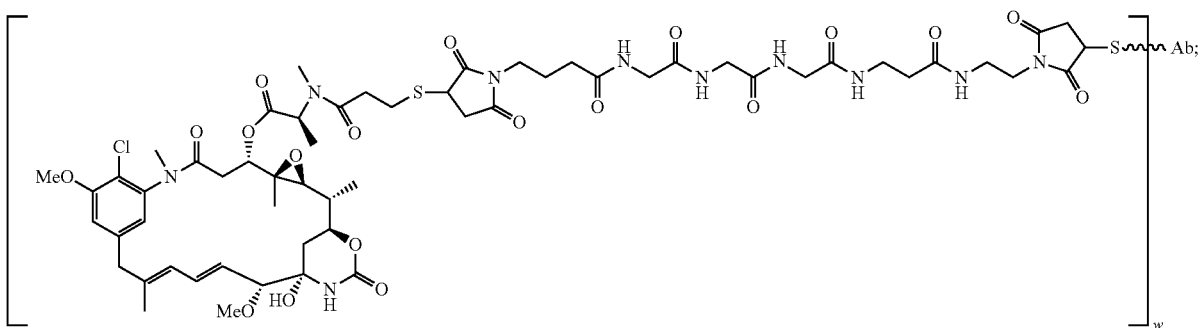

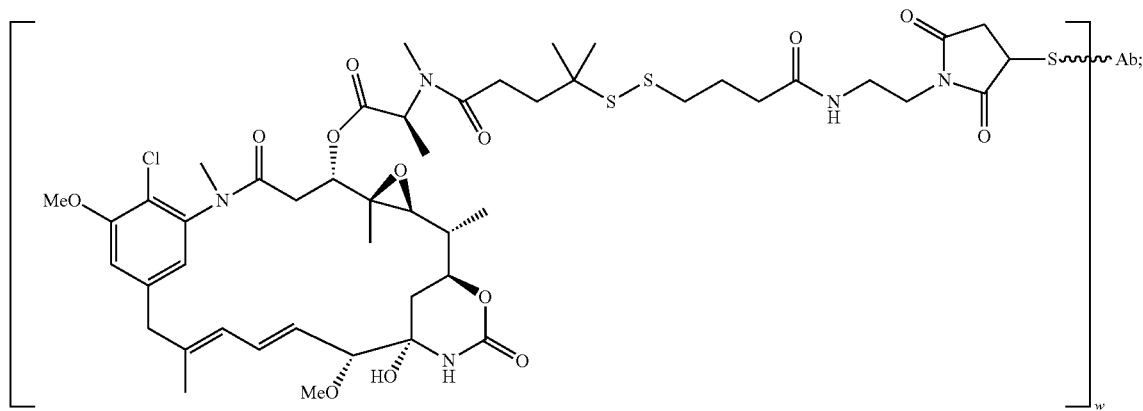
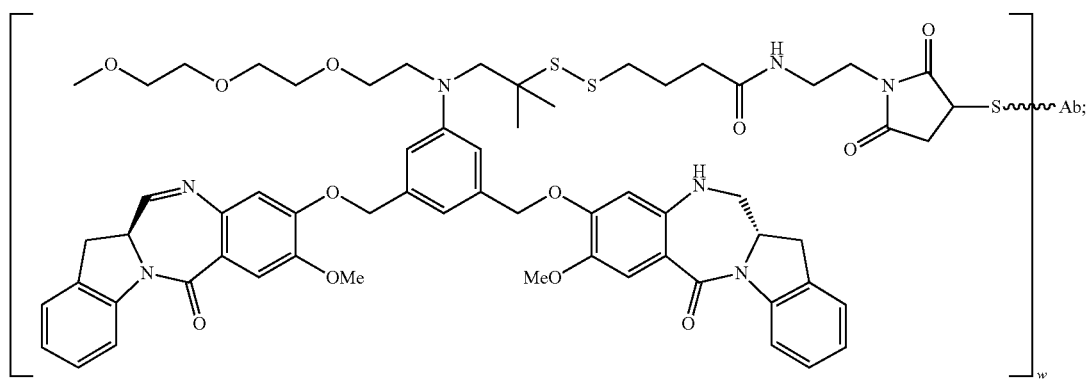
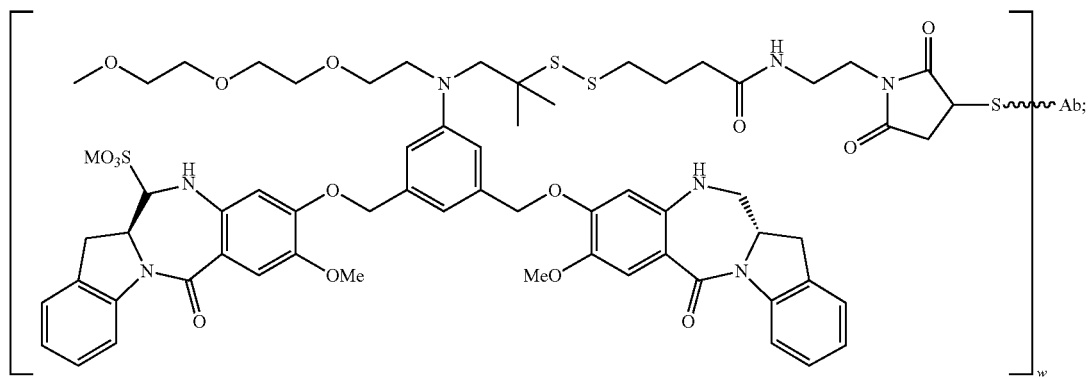
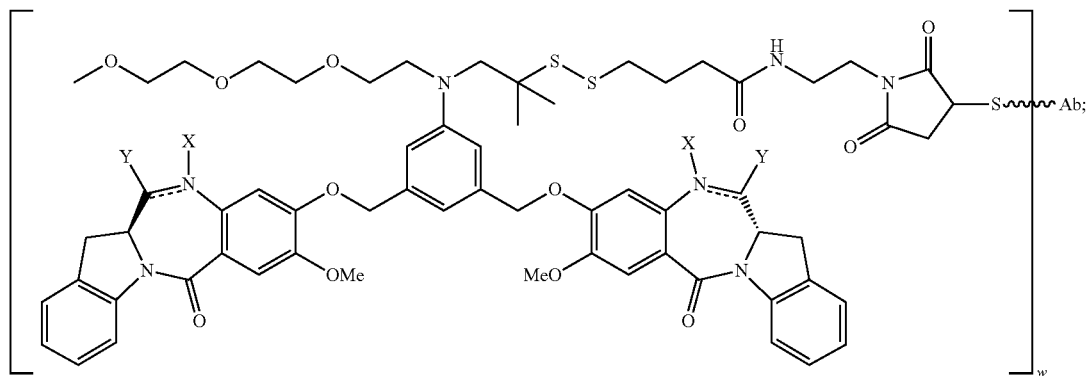

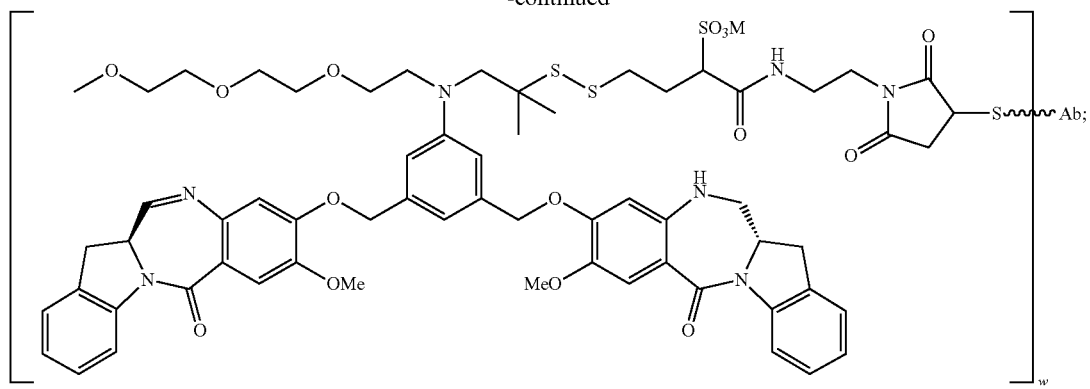
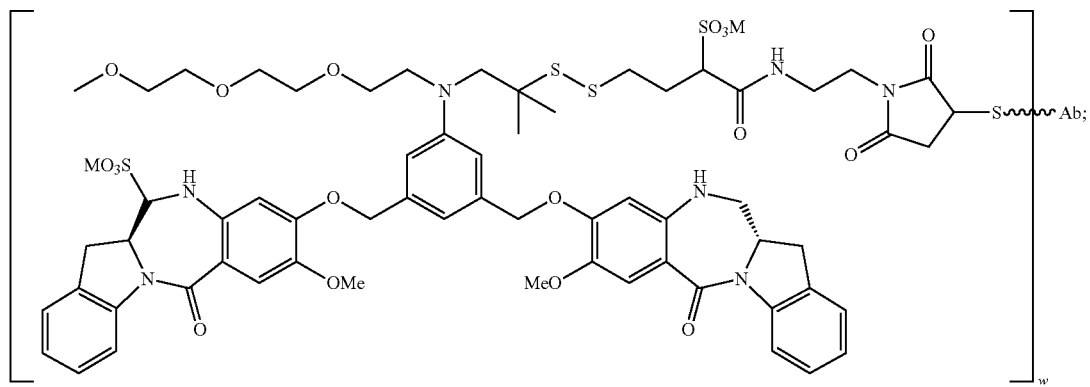
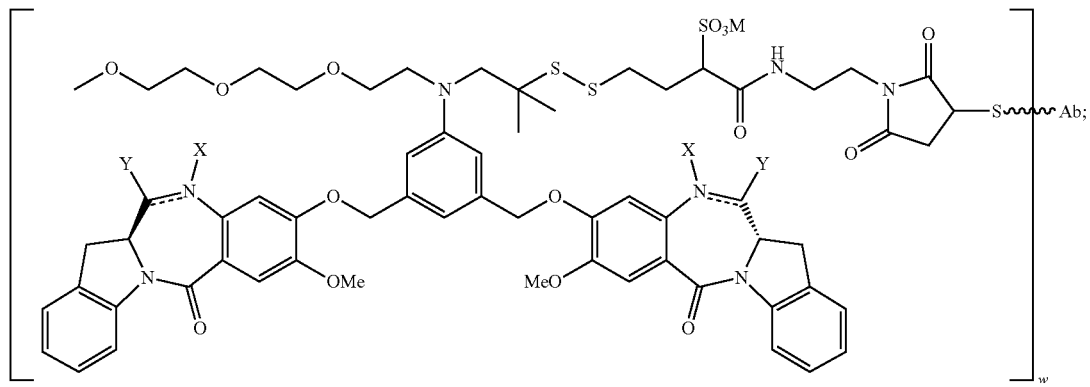
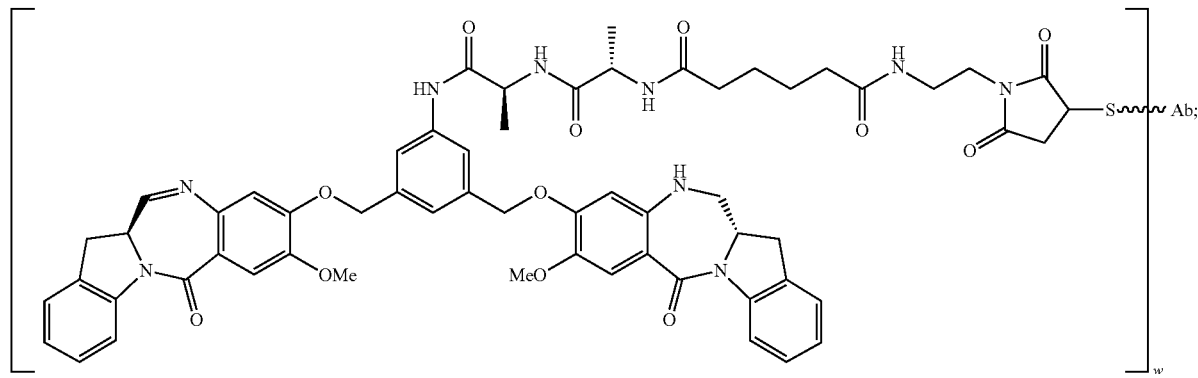

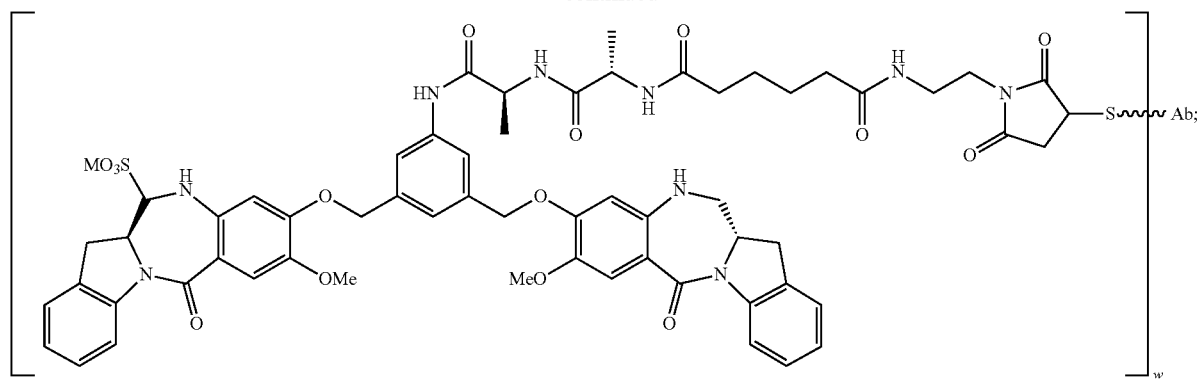
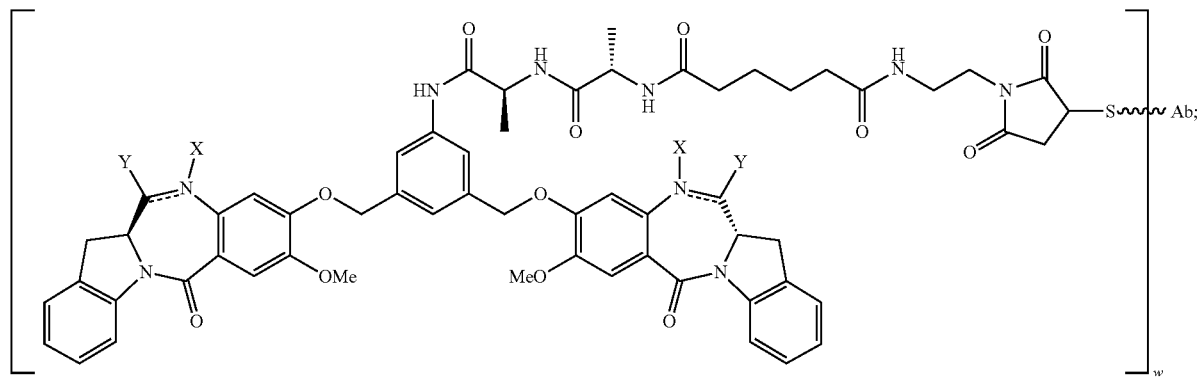
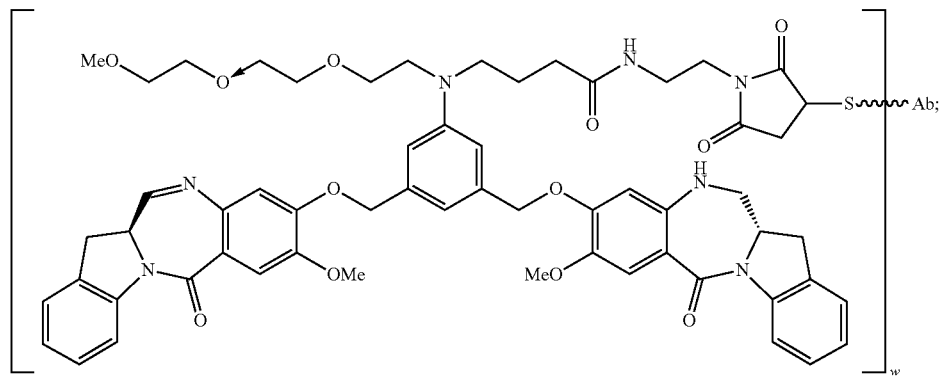
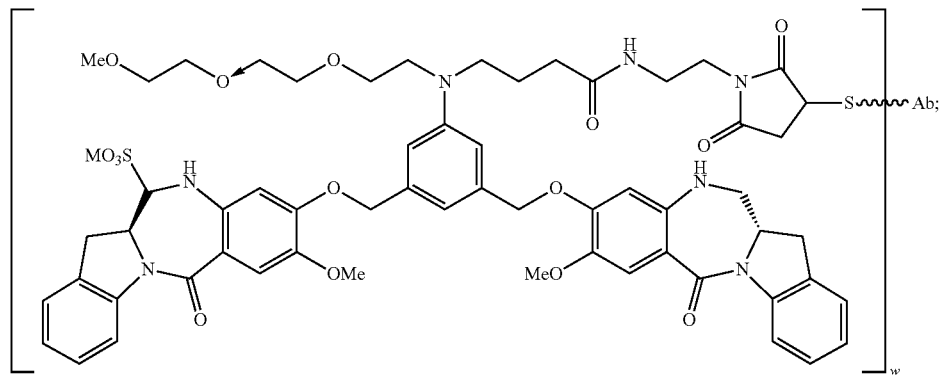

-continued
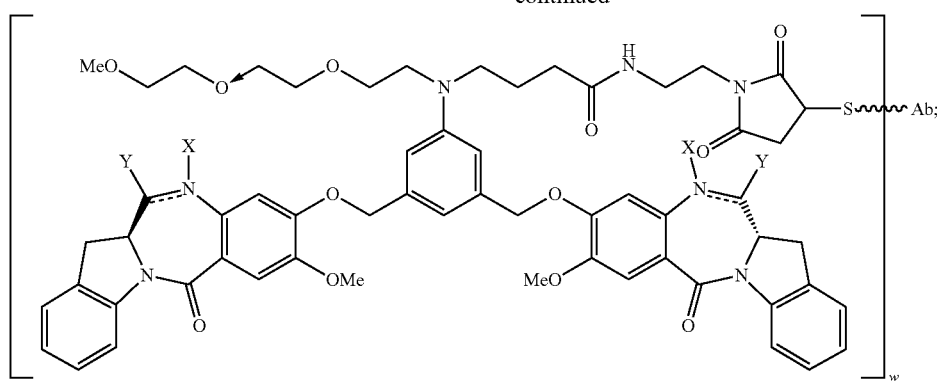
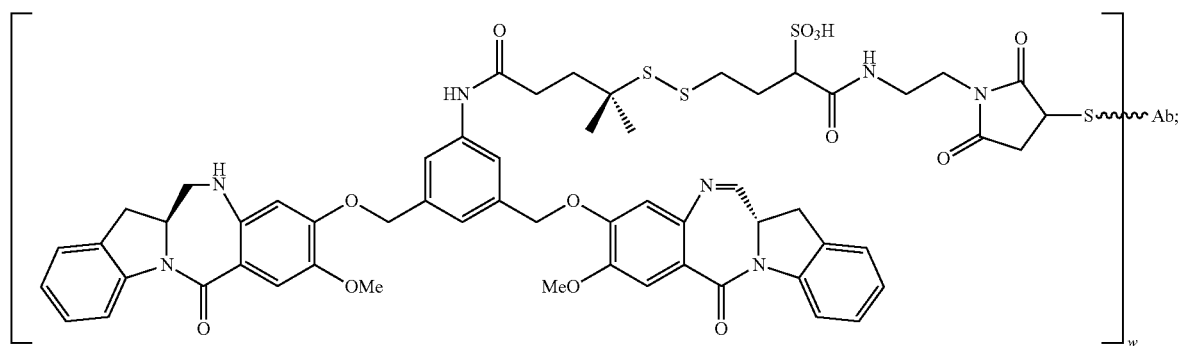
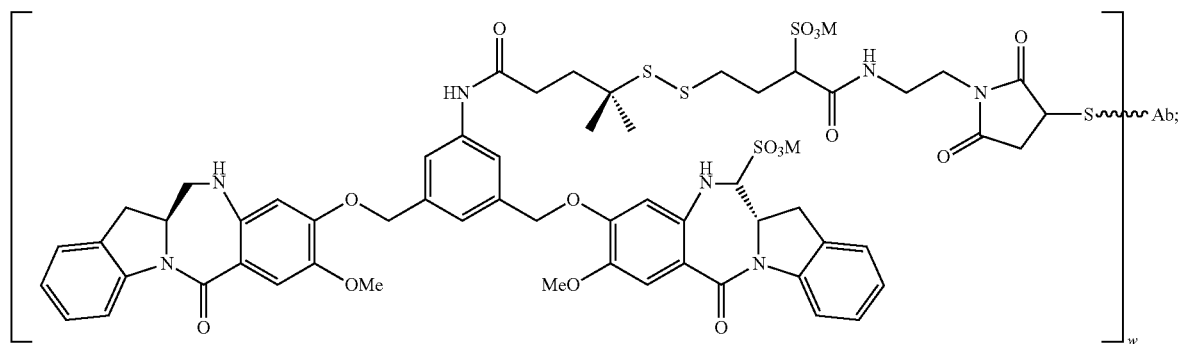
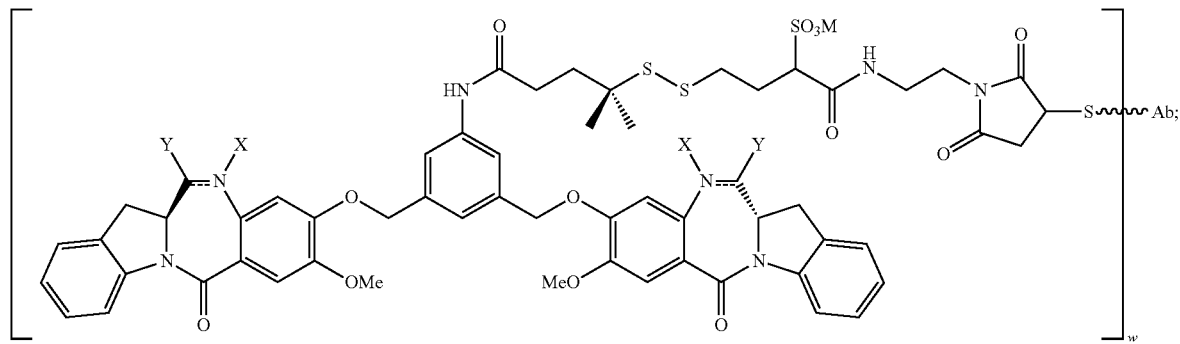

-continued

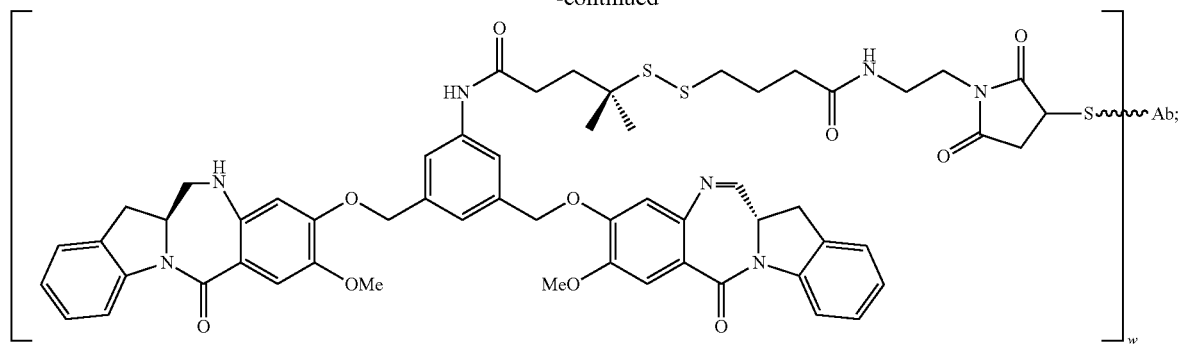

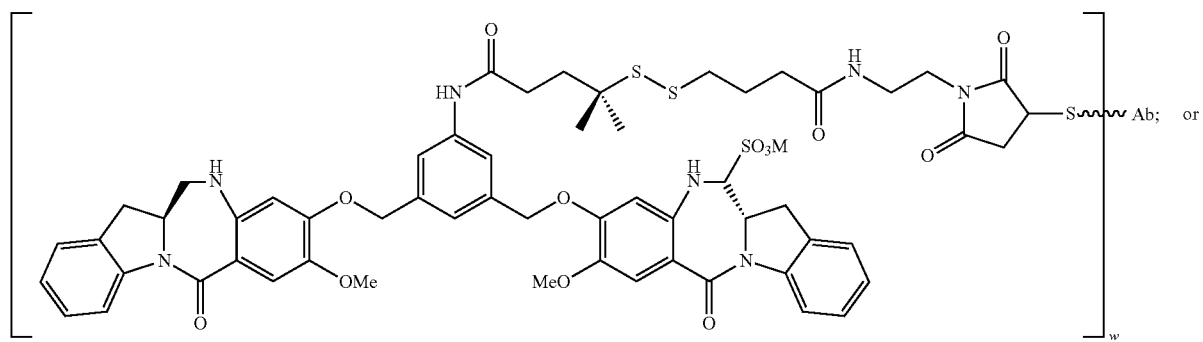

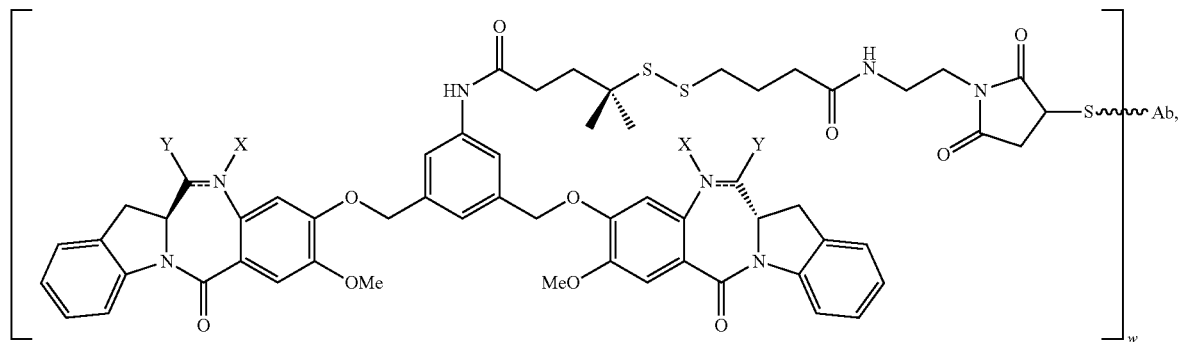

or a pharmaceutically acceptable salt thereof, wherein the double line == between N and C represents a single bond or a double bond, provided that when it is a double bond, X is absent and Y is —H, and when it is a single bond, X is —H, and Y is —SO₃M; and M is H⁺ or a pharmaceutically acceptable cation. More specifically, M is H⁺, Na⁺ or K⁺.

Also in the 24ᵗʰ embodiment, for compounds of formula (II), the compound is represented by the following structural formula:

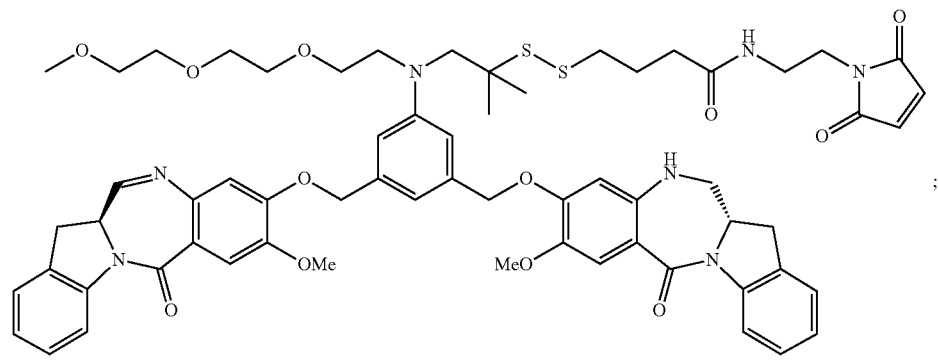

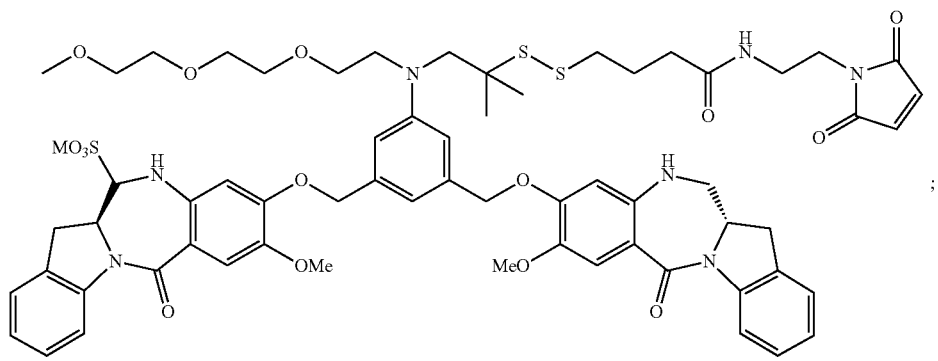
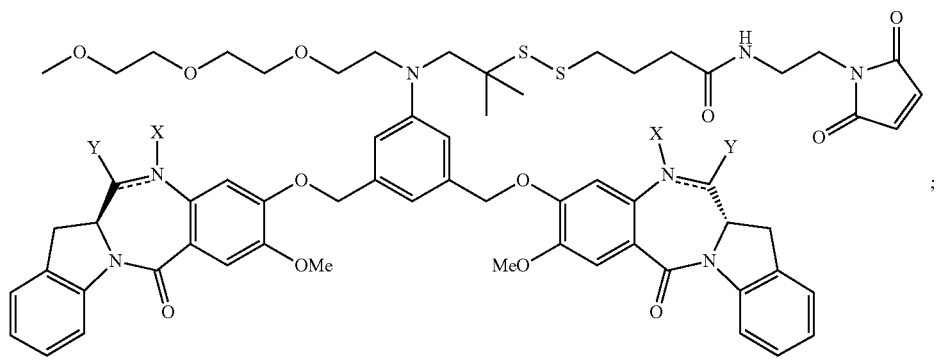
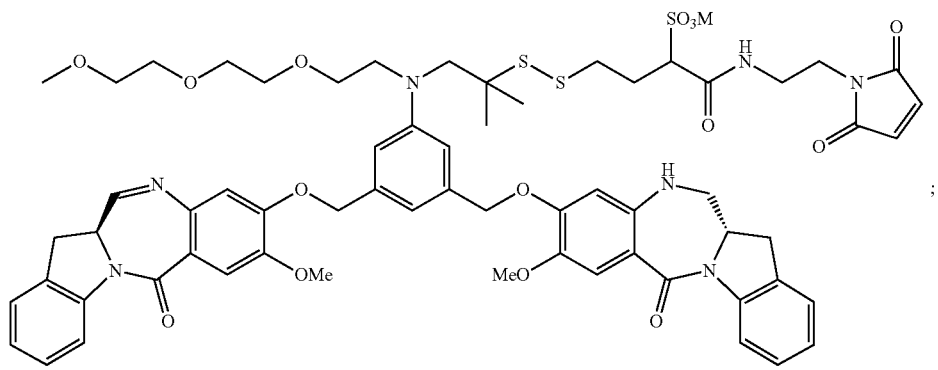
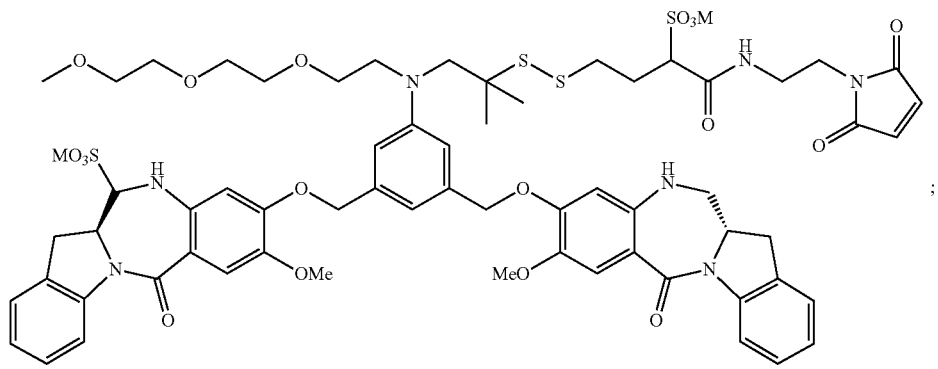

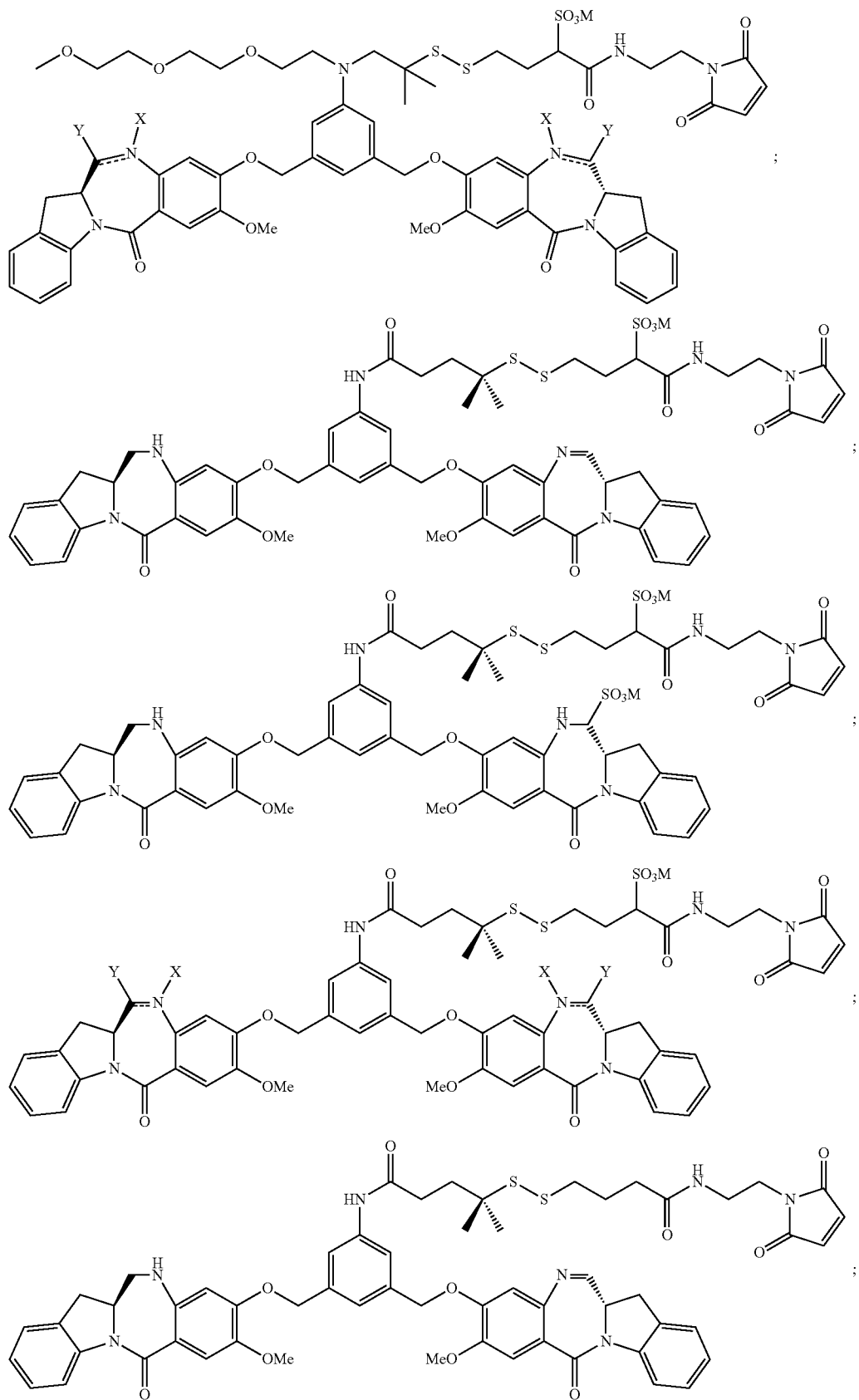

-continued

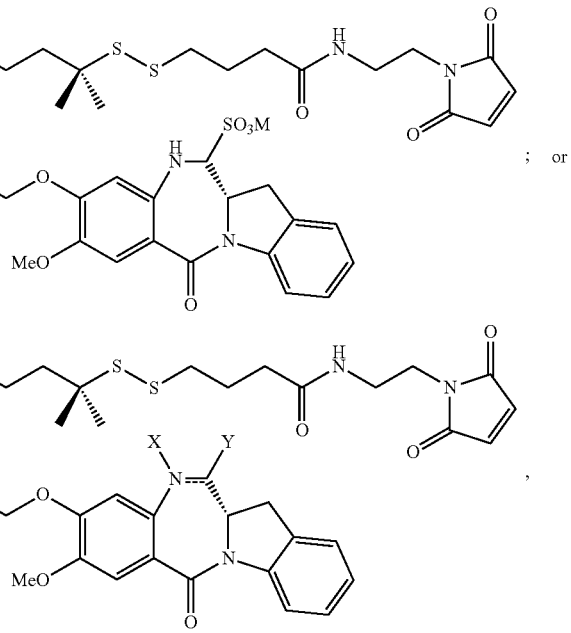

or a pharmaceutically acceptable salt thereof, wherein the double line == between N and C represents a single bond or a double bond, provided that when it is a double bond, X is absent and Y is —H, and when it is a single bond, X is —H, and Y is —SO$_3$M; and M is H$^+$ or a pharmaceutically acceptable cation.

In a 25$^{th}$ embodiment, for conjugates described in the first embodiment or any one of the 1$^{st}$-24$^{th}$ embodiments, w is 2. Alternatively, w is 1.

In certain embodiments, the charged substituent or an ionizable group Q described in any embodiments above is i) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a pharmaceutically acceptable salt thereof; or, ii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an optionally substituted phenylene; R$_{14}$ to R$_{16}$ are each independently an optionally substituted alkyl; and X$^-$ is a pharmaceutically acceptable anion. More specifically, Q is —SO$_3$H or a pharmaceutically acceptable salt thereof.

In certain embodiments, the antibody in the conjugates of the present invention is an antibody having an engineered cysteine residue (e.g., at the EU/OU numbering position 442 of the heavy chain(s)). The engineered Cys residue can be located on one or both heavy chains of the antibody, or on one or both light chains of the antibody, or antigen-binding portion thereof, or a combination thereof. In one embodiment, the Cys residue is located at the EU/OU numbering position 442 of the antibody heavy chain(s). In certain embodiment, the antibody is a cysteine engineered antibody as described herein.

In certain embodiments, the antibody of the present invention is a monoclonal antibody, a chimeric antibody, a humanized antibody, a resurfaced antibody, or a human antibody.

In other embodiments, the cell-binding agent is an antibody, a single chain antibody, an antibody fragment that specifically binds to the target cell, a monoclonal antibody, a single chain monoclonal antibody, a monoclonal antibody fragment (or "antigen-binding portion") that specifically binds to a target cell, a chimeric antibody, a chimeric antibody fragment (or "antigen-binding portion") that specifically binds to the target cell, a domain antibody (e.g., sdAb), or a domain antibody fragment that specifically binds to the target cell.

In certain embodiments, the cell-binding agent is a humanized antibody, a humanized single chain antibody, or a humanized antibody fragment (or "antigen-binding portion"). In a specific embodiment, the humanized antibody is huMy9-6 or another related antibody, which is described in U.S. Pat. Nos. 7,342,110 and 7,557,189. In another specific embodiment, the humanized antibody is an anti-folate receptor antibody described in U.S. Pat. No. 8,557,966. In yet another embodiment, the humanized antibody is an anti-CD123 antibody described in U.S. Provisional Application No. 62/186,161, filed on Jun. 29, 2015, entitled "ANTI-CD123 ANTIBODIES AND CONJUGATES AND DERIVATIVES THEREOF." The teachings of all these applications are incorporated herein by reference in its entirety.

In certain embodiments, the cell-binding agent is a resurfaced antibody, a resurfaced single chain antibody, a resurfaced antibody fragment (or "antigen-binding portion"), or a bispecific antibody.

Yet another aspect of the invention provides a recombinant antibody comprising a mature processed sequence of the heavy chain, light chain, or antigen-binding portion thereof, derived from any one of the subject recombinant antibody heavy chain (HC), light chain (LC), or antigen-binding portion thereof described herein.

For example, the recombinant antibody may be or may comprise an scFv-Fc, Fcab, mAb2, small modular immunopharmaceutical (SMIP), Genmab/unibody or duobody, minibody, IgGΔCH$_2$, DVD-Ig, probody, intrabody, or a multispecificity antibody.

A DUOBODY® is a bispecific modified IgG1 antibody heterodimer. IgG1 hinge region that generally includes (i) a stable hinge region that contains a CPPC sequence and is non-permissive for Fab arm exchange in vivo and (ii) an IgG4-like CH3 domain that is modified to contain F405L and K409R residues, which renders it permissive for Fab arm exchange in vivo. (See, for example, WO2008119353 and WO2011131746).

In certain embodiments, the recombinant antibody may comprise 1, 2, 3, or 4 of the mature processed sequence of the heavy chain, light chain, or antigen-binding portion thereof, each derived from any one of the subject recombinant antibody heavy chain (HC), light chain (LC), or antigen-binding portion thereof described herein.

In certain embodiments, the recombinant antibody may be a heterodimeric antibody comprising a first heavy chain polypeptide and a second heavy chain polypeptide, wherein the Fc region of the first heavy chain polypeptide and the Fc region of the second heavy chain polypeptide meet at an interface, and the interface of the Fc region of the second heavy chain polypeptide comprises a protuberance which is positionable in a cavity in the interface of the Fc region of the first heavy chain polypeptide. In certain embodiments, the knob-into-hole technology to promote specific pairing of heavy chains in the bi-specific antibody may be further improved based on, for example, the CrossMab technology of Genentech/Roche, e.g., by swapping CH1 and Kappa constant regions to further reduce or eliminate light chain mis-pairing.

Alternatively, similar results can also be achieved using LC heterodimers, such as Zymeworks AZYMETRIC™ heterodimeric IgG1 light chain platform technology that fully complements multiple other biologics approaches, including common light chain, domain antibody, and single chain formats, in the development of fully bi-specific antibodies.

In certain embodiments, the Fc region of the second heavy chain polypeptide has been altered from a template/original polypeptide to encode the protuberance, or the Fc region of the first heavy chain polypeptide has been altered from a template/original polypeptide to encode the cavity, or both.

In certain embodiments, the protuberance and the cavity each comprises a naturally occurring amino acid residue.

In certain embodiments, the Fc region of the second heavy chain polypeptide comprising the protuberance is generated by replacing an original residue from the interface of a template/original polypeptide with an import residue having a larger side chain volume than the original residue.

In certain embodiments, the Fc region of the second heavy chain polypeptide comprising the protuberance is generated by a method comprising a step wherein nucleic acids encoding an original residue from the interface of said polypeptide is replaced with nucleic acids encoding an import residue having a larger side chain volume than the original.

In certain embodiments, the antibody includes bispecific, multispecific, and monospecific antibody variants that include the antigen bind regions and the heavy chain constant domain, wherein the heavy chain constant domain is modified to include a Cys at position 442 of the EU/OU numbering.

In certain embodiments, the antibody may bind to a ligand on the target cell, such as a cell-surface ligand, including cell-surface receptors.

Specific exemplary antigens or ligands may include renin; a growth hormone (e.g., human growth hormone and bovine growth hormone); a growth hormone releasing factor; a parathyroid hormone; a thyroid stimulating hormone; a lipoprotein; alpha-1-antitrypsin; insulin A-chain; insulin B-chain; proinsulin; a follicle stimulating hormone; calcitonin; a luteinizing hormone; glucagon; a clotting factor (e.g., factor vmc, factor IX, tissue factor, and von Willebrands factor); an anti-clotting factor (e.g., Protein C); atrial natriuretic factor; a lung surfactant; a plasminogen activator (e.g., a urokinase, a human urine or tissue-type plasminogen activator); bombesin; a thrombin; hemopoietic growth factor; tumor necrosis factor-alpha and -beta; an enkephalinase; RANTES (i.e., the regulated on activation normally T-cell expressed and secreted); human macrophage inflammatory protein-1-alpha; a serum albumin (human serum albumin); Muellerian-inhibiting substance; relaxin A-chain; relaxin B-chain; prorelaxin; a mouse gonadotropin-associated peptide; a microbial protein (beta-lactamase); DNase; IgE; a cytotoxic T-lymphocyte associated antigen (e.g., CTLA-4); inhibin; activin; a vascular endothelial growth factor; a receptor for hormones or growth factors; protein A or D; a rheumatoid factor; a neurotrophic factor (e.g., bone-derived neurotrophic factor, neurotrophin-3, -4, -5, or -6), a nerve growth factor (e.g., NGF-β); a platelet-derived growth factor; a fibroblast growth factor (e.g., aFGF and bFGF); fibroblast growth factor receptor 2; an epidermal growth factor; a transforming growth factor (e.g., TGF-alpha, TGF-β1, TGF-β2, TGF-β3, TGF-β4, and TGF-β5); insulin-like growth factor-I and —II; des(1-3)-IGF-I (brain IGF-I); an insulin-like growth factor binding protein; melanotransferrin; EpCAM; GD3; FLT3; PSMA; PSCA; MUC1; MUC16; STEAP; CEA; TENB2; an EphA receptor; an EphB receptor; a folate receptor; FOLR1; mesothelin; cripto; an alpha$_v$beta$_6$; integrins; VEGF; VEGFR; EGFR; transferrin receptor; IRTA1; IRTA2; IRTA3; IRTA4; IRTA5; CD proteins (e.g., CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD123, CD134, CD137, CD138, and CD152), one or more tumor-associated antigens or cell-surface receptors (see US Publication No. 2008/0171040 or US Publication No. 2008/0305044, incorporated in their entirety by reference); erythropoietin; an osteoinductive factor; an immunotoxin; a bone morphogenetic protein; an interferon (e.g., interferon-alpha, -beta, and -gamma); a colony stimulating factor (e.g., M-CSF, GM-CSF, and G-CSF); interleukins (e.g., IL-1 to IL-10); a superoxide dismutase; a T-cell receptor; a surface membrane protein; a decay accelerating factor; a viral antigen (e.g., a portion of the HIV envelope); a transport protein, a homing receptor; an addressin; a regulatory protein; an integrin (e.g., CD11a, CD11b, CD11c, CD18, an ICAM, VLA-4, and VCAM;) a tumor associated antigen (e.g., HER2, HER3 and HER4 receptor); endoglin; c-Met; c-kit; 1GF1R; PSGR; NGEP; PSMA; PSCA; TMEFF2; LGR5; B7H4; and fragments of any of the above-listed polypeptides.

In one embodiment, the cell-binding agent is an anti-folate receptor antibody. More specifically, the anti-folate receptor antibody is a humanized antibody that specifically binds a human folate receptor 1, wherein the antibody comprises: (a) a heavy chain CDR1 comprising GYFMN (SEQ ID NO: 1); a heavy chain CDR2 comprising RIHPYDGDTFYNQXaaiFXaa$_2$Xaa$_3$ (SEQ ID NO: 2); and a heavy chain CDR3 comprising YDGSRAMDY (SEQ ID NO: 3); and (b) a light chain CDR1 comprising KASQSVS-FAGTSLMH (SEQ ID NO: 4); a light chain CDR2 comprising RASNLEA (SEQ ID NO: 5); and a light chain CDR3 comprising QQSREYPYT (SEQ ID NO: 6); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG (SEQ ID NO: 7).

In another embodiment, the anti-folate receptor antibody is a humanized antibody or antigen binding fragment thereof that specifically binds the human folate receptor 1 comprising the heavy chain having the amino acid sequence of QVQLVQSGAEVVKPGASVKISCK-ASGYTFTGYFMNWVKQSPGQSLEWIGRIHPYDGDT FYNQKFQGKATLTVDKSSNTAHMELLSLTSED-FAVYYCTRYDGSRAMDYWGQGTTVT VSSAS-TKGPSVFPLAPSSKSTSGGTAALGCLVKDYF-PEPVTVSWNSGALTSGVHTFPAVL QSSGLYS-LSSVVTVPSSSLGTQTYICNVNHKPSNTKVDKKVE-PKSCDKTHTCPPCPAPEL LGGPSVFLFPPKPKDTLMISRTPE-VTCVVVDVSHEDPE-VKFNWYVDGVEVHNAKTKPRE EQYNSTYRVVS VLTVLHQDWLNGKEYKCKVSNKALPA-PIEKTISKAKGQPREPQVYTLP PSRDELTKNQVSLT-CLVKGFYPSDIAVEWESNGQPEN-NYKTTPPVLDSDGSFFLYSKLTV DKSRWQQGNVFSCSVMHEALHNHYTQKSLCLSPG (SEQ ID NO: 8).

In another embodiment, the anti-folate receptor antibody is a humanized antibody or antigen binding fragment thereof that specifically binds the human folate receptor 1 comprising the light chain having the amino acid sequence of DIVLTQSPLSLAVSLGQPAIISCKASQSVSFAGT-SLMHWYHQKPGQQPRLLIYRASNLEA GVPDRFSGSGS KTDFTLNISPVEAEDAATYYCQQS-REYPYTFGGGTKLEIKRTVAAPSVF IFPPSDEQLKSG-TASVVCLLNNFYPREAKVQWKVD-NALQSGNSQESVTEQDSKDSTYSL SSTLTLSKADYEKHKVYACE-VTHQGLSSPVTKSFNRGEC (SEQ ID NO: 9); or DIVLTQSPLSLAVSLGQPAIISCKASQSVSFAGT-SLMHWYHQKPGQQPRLLIYRASNLEA GVPDRFSGSGS KTDFTLTISPVEAEDAATYYCQQS-REYPYTFGGGTKLEIKRTVAAPSVFI FPPSDEQLKSG-TASVVCLLNNFYPREAKVQWKVD-NALQSGNSQESVTEQDSKDSTYSLS STLTLSKADYEKHKVYACE-VTHQGLSSPVTKSFNRGEC (SEQ ID NO: 10).

In another embodiment the anti-folate receptor antibody is a humanized antibody or antigen binding fragment thereof that specifically binds the human folate receptor 1 comprising the heavy chain having the amino acid sequence of SEQ ID NO: 8, and the light chain having the amino acid sequence of SEQ ID NO: 9 or SEQ ID NO: 10. Preferably, the antibody comprises the heavy chain having the amino acid sequence of SEQ ID NO: 8 and the light chain having the amino acid sequence of SEQ ID NO: 10 (huMov19).

In another embodiment, the anti-folate receptor antibody is a humanized antibody or antigen binding fragment thereof comprising an engineered Cys residue (e.g., C442) and a heavy chain variable domain at least about 90%, 95%, 99% or 100% identical to QVQLVQSGAEVVKPGASVKISCK-ASGYTFTGYFMNWVKQSPGQSLEWIGRIHPYDGDT FYNQKFQGKATLTVDKSSNTAHMELLSLTSED-FAVYYCTRYDGSRAMDYWGQGTTVT VSS (SEQ ID NO: 11), and a light chain variable domain at least about 90%, 95%, 99% or 100% identical to DIVLTQSPLSLAVSLGQPAIISCKASQSVSFAGT-SLMHWYHQKPGQQPRLLIYRASNLEA GVPDRFSGSGSKTDFTLNISPVEAEDAATYYCQQS-REYPYTFGGGTKLEIKR (SEQ ID NO: 12); or DIVLTQSPLSLAVSLGQPAIISCKASQSVSFAGT-SLMHWYHQKPGQQPRLLIYRASNLEA GVPDRFSGSGSKTDFTLTISPVEAEDAATYYCQQS-REYPYTFGGGTKLEIKR (SEQ ID NO: 13).

In a specific embodiment, the humanized antibody is huMy9-6 or another related antibody, which is described in U.S. Pat. Nos. 7,342,110 and 7,557,189. In another specific embodiment, the humanized antibody is an anti-folate receptor antibody (e.g., huMov19) described in U.S. Pat. No. 8,577,966. In certain embodiments the humanized antibody is an anti-CD37 antibody (e.g., anti-CD37-3) described in U.S. Pat. No. 8,765,917. In certain embodiments, the humanized antibody is an anti-EGFR antibody described in U.S. Pat. No. 8,790,649. In another embodiment, the antibody is an anti-EGFR antibody. In one embodiment, the anti-EGFR antibody is a non-antagonist antibody, including, for example, the antibodies described in WO2012058592, herein incorporated by reference. In another embodiment, the anti-EGFR antibody is a non-functional antibody, for example, humanized ML66. More specifically, the anti-EGFR antibody is huML66.

In one embodiment, the antibody is an anti-CD123 antibody, such as a humanized huCD123 antibody as described in U.S. Provisional Application No. 62/186,161, filed on Jun. 29, 2015, entitled "ANTI-CD123 ANTIBODIES AND CONJUGATES AND DERIVATIVES THEREOF" (entire contents, including all sequences and drawings, incorporated herein).

Method of Preparing the Conjugates of the Present Invention

The immunoconjugates described above (e.g., immunoconjugates of formula (I) or immunoconjugates of any one of the 1$^{st}$ to 25$^{th}$ embodiments or any specific embodiments described therein) can be prepared by reacting the antibody having one or more free cysteine with a compound having a thiol-reactive group described herein.

In one embodiment, the compound having a thiol-reactive group is represented by formula (II) or compounds of any one of the 1$^{st}$ to 25$^{th}$ embodiments or any specific embodiments described therein.

In certain embodiments, organic solvents are used in the reaction of the CBA and the compound having a thiol-reactive group to solubilize the compound. Exemplary organic solvents include, but are not limited to, dimethylacetamide (DMA), propylene glycol, etc. In one embodiment, the reaction of the CBA and the compound is carried out in the presence of DMA and propylene glycol.

Compositions and Methods of Use

The present invention includes a composition (e.g., a pharmaceutical composition) comprising novel benzodiazepine compounds described herein (e.g., indolinobenzodiazepine or oxazolidinobenzodiazepine), derivatives thereof, or conjugates thereof, (and/or solvates, hydrates and/or salts thereof) and a carrier (a pharmaceutically acceptable carrier). The present invention also includes a composition (e.g., a pharmaceutical composition) comprising novel benzodiazepine compounds described herein, derivatives thereof, or conjugates thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human). The present invention includes a method of inhibiting abnormal cell growth or treating a proliferative disorder in a mammal (e.g., human) comprising administering to said mammal a therapeutically effective amount of a therapeutic agent or composition, such as a novel benzodiazepine compounds described herein (e.g., indolinobenzodiazepine or oxazolidinobenzodiazepine), derivatives thereof, or conjugates thereof, (and/or solvates and salts thereof) or a composition thereof, alone or in combination with a second therapeutic agent.

In one embodiment, the proliferative disorder is cancer. Cancer can include a hematological cancer or a solid tumor. More specifically, the cancer is leukemia (e.g., acute myeloid leukemia (AML), acute lymphoblastic leukemia (ALL) such as acute B lymphoblastic leukemia (B-ALL), chronic myelogenous leukemia (CML), chronic lymphocytic leukemia (CLL)) or lymphoma, melanoma, lung cancer (e.g., non-small cell lung cancer), ovarian cancer, endometrial cancer, peritoneal cancer, pancreatic cancer, breast cancer, prostate cancer, and cervical cancer.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the cytotoxic compound-cell-binding agents (e.g., indolinobenzodiazepine or oxazolidinobenzodiazepine dimer linked to a cell binding agent) of the present invention, a salt or solvate thereof. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants. Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells; treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen. The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 µM to 1 µM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

Specific clinical protocols with regard to route of administration, excipients, diluents, dosages, times, etc., can be determined by one of ordinary skill in the art as the clinical situation warrants.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include:

Comprehensive index
By Manufacturer
Products (by company's or trademarked drug name)
Category index
Generic/chemical index (non-trademark common drug names)
Color images of medications
Product information, consistent with FDA labeling
Chemical information
Function/action
Indications & Contraindications
Trial research, side effects, warnings

EXAMPLES

Example 1 Preparation of Linker-Effector Reagents for Antibody Conjugation

The following solvents, reagents, protecting groups, moieties and other designations may be referred to by their abbreviations in parenthesis:

| | |
|---|---|
| Me | methyl |
| i-Pr | isopropyl |
| Ph | phenyl |
| Ala | alanine |
| DI water | deionized water |
| g | grams |
| h | hour |
| min | minutes |
| mg | milligrams |
| mL | milliliters |
| μg | micrograms |
| μL | microliters |
| sat or sat'd | saturated |
| THF | tetrahydrofuran |
| Et | ethyl |
| Bu | butyl |
| Ac | acetyl |
| aq | aqueous |
| DCM/CH$_2$Cl$_2$ | dichloromethane |
| DMA | N,N-dimethylacetamide |
| DMF | N,N-dimethylformamide |
| EtOAc | ethylacetate |
| LC | liquid chromatography |
| mmol | millimoles |
| μmol | micromoles |
| MeOH | methanol |
| RT or rt | room temperature (ambient, about 25° C.) |
| TEA | triethylamine (Et$_3$N) |
| Pr | propyl |
| t-Bu | tert-butyl |
| AcOH/HOAc | acetic acid |
| ACN/CH$_3$CN | acetonitrile |
| Boc/BOC | tert-butoxycarbonyl |
| DIEA or DIPEA | N,N-diisopropylethylamine |
| EDC | 1-ethyl-3-(3-dimethylaminopropyl) carbodiimide |
| ESI or ES | electrospray ionization |
| HPLC | high-performance liquid chromatography |
| LCMS | liquid chromatography mass spectrometry |
| MS | mass spectrometry |
| NHS | N-hydroxy succinamide |
| NMR | nuclear magnetic resonance spectrascopy |
| RPHPLC or RP-HPLC | reverse phase high-performance liquid chromatography |

A. Synthesis of N-(2-(2,5-dioxo-2,5-dihydro-1H-pyrrol-1-yl)ethyl)-11-(3-(((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)-13,13-dimethyl-2,5,8-trioxa-14,15-dithia-1-azanonadecan-19-amide, compound D6

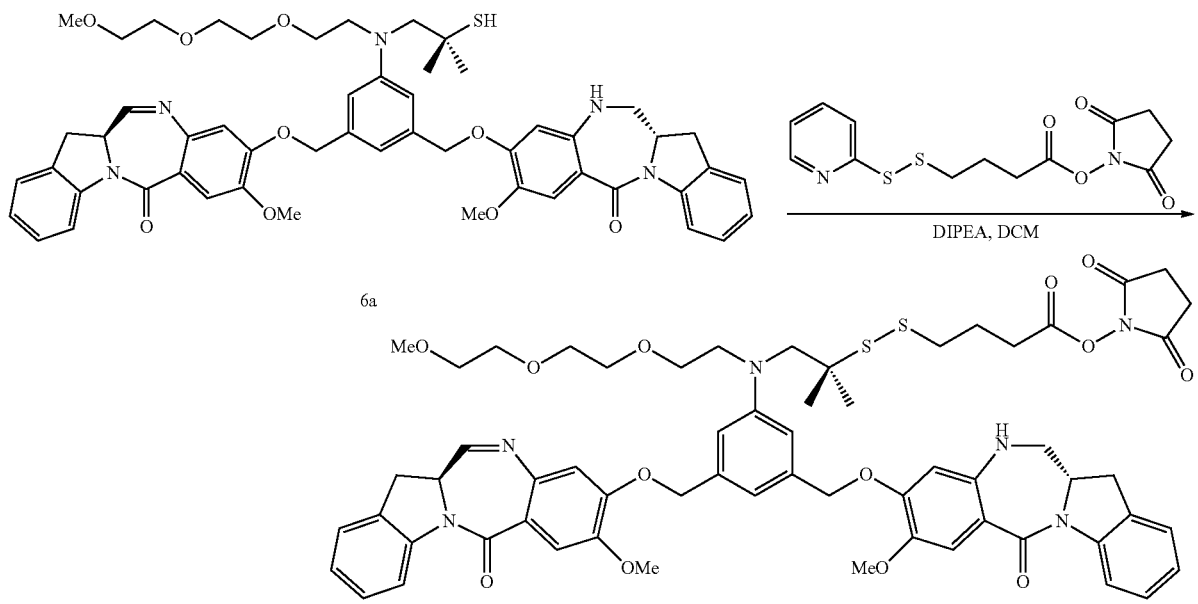

To a solution of the free thiol 6a (40 mg, 0.042 mmol) and NHS 4-(2-pyridyldithio)butanate (35 mg, 80% purity, 0.085 mmol) in anhydrous dichloromethane (0.5 mL) was added anhydrous diisopropylethylamine (0.015 mL, 0.085 mmol) and was stirred at room temperature for 16 hours. The reaction mixture was quenched with saturated ammonium chloride and diluted with dichloromethane. The obtained mixture was separated in a separatory funnel. The organic layer was washed with brine, dried over anhydrous sodium sulfate, filtered and stripped under reduced pressure. The residue was purified by semi-preparative reverse phase HPLC (C18 column, CH$_3$CN/H$_2$O). The fractions that contained pure product were combined, frozen and lyophilized to give the desired NHS ester, 6b (29.7 mg, 60% yield). LCMS=9.1 min (15 min method). MS (m/z): 1157.3 (M+1)$^+$.

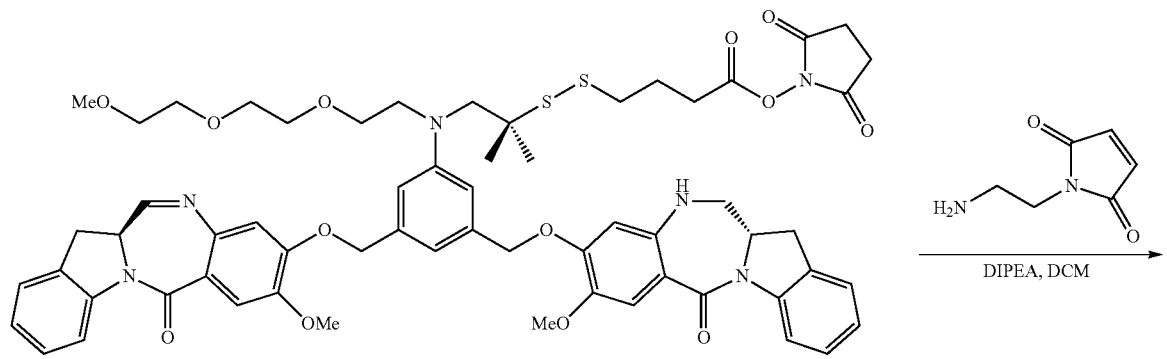

2

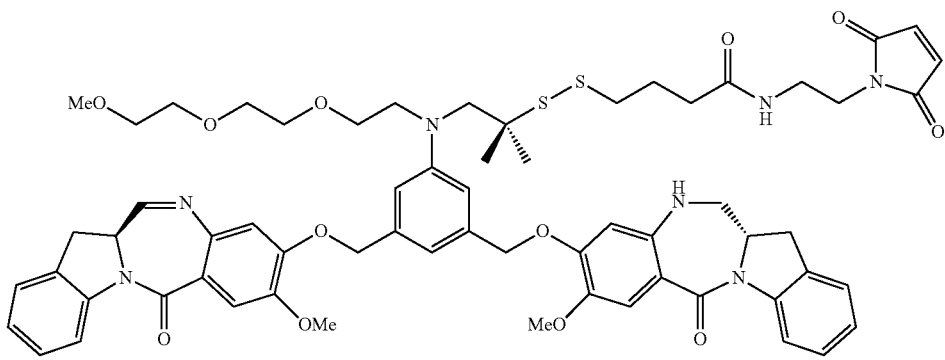

3

To a solution of the NHS ester, 6b (12.3 mg, 0.011 mmol) and N-(2-aminoethyl)maleimide hydrochloride (2.0 mg, 0.011 mmol) in anhydrous dichloromethane (0.3 mL) was added DIPEA (0.0022 mL, 0.013 mmol). The mixture was stirred at room temperature for 3 hours then it was stripped under reduced pressure. The residue was purified by semi-preparative reverse phase HPLC (C18 column, $CH_3CN$/ $H_2O$). The fractions that contained pure product were combined, frozen and lyophilized to give the desired maleimide, compound D6 (10 mg, 80% yield). LCMS=8.3 min (15 min method). MS (m/z): 1181.8 (M+1)+.

B. Synthesis of N-(2-(2,5-dioxo-2,5-dihydro-1H-pyrrol-1-yl)ethyl)-N6-((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-(((((S)-8-methoxy-6-oxo-12a,13-dihydro-6H-benzo[5,6][1,4]diazepino[1,2-a]indol-9-yl)oxy)methyl)phenyl)amino)-1-oxopropan-2-yl)amino)-1-oxopropan-2-yl)adipamide, compound D5

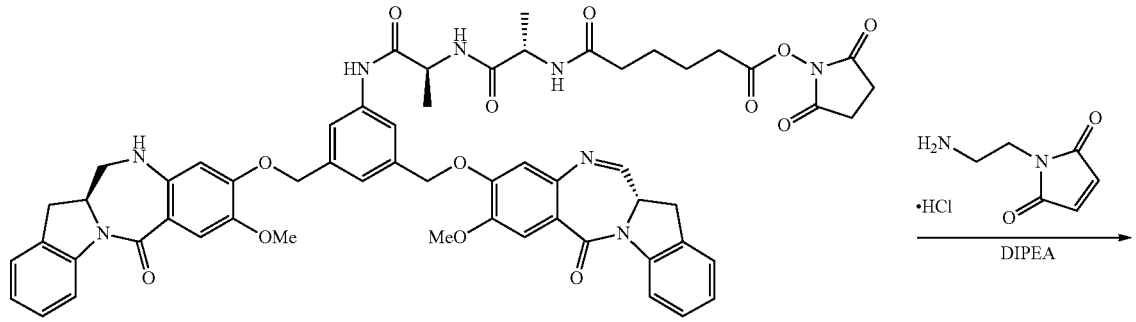

5a

-continued

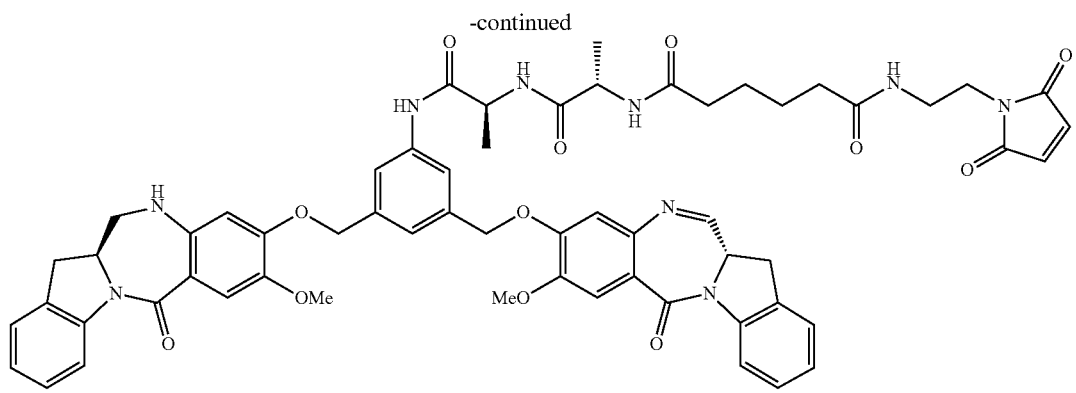

D5

NHS ester 5a (8.2 mg, 7.6 µmol) and 1-(2-aminoethyl)-1H-pyrrole-2,5-dione hydrochloride (2.2 mg, 0.011 mmol) were dissolved in anhydrous dichloromethane (305 µL) at room temperature. DIPEA (2.66 µL, 0.015 mmol) was added and the reaction and was stirred for 3.5 hours. The reaction mixture was concentrated and was purified by RPHPLC (C18 column, $CH_3CN/H_2O$, gradient, 35% to 55%). The desired product fractions were frozen and lyophilized to give maleimide, compound D5 as a solid white powder (5.3 mg, 58% yield). LCMS=5.11 min (8 min method). MS (m/z): 1100.6 (M+1)[+].

C. Synthesis of 1-((2-(2,5-dioxo-2,5-dihydro-1H-pyrrol-1-yl)ethyl)amino)-4-((5-((3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)amino)-2-methyl-5-oxopentan-2-yl)disulfanyl)-1-oxobutane-2-sulfonic acid, compound D4

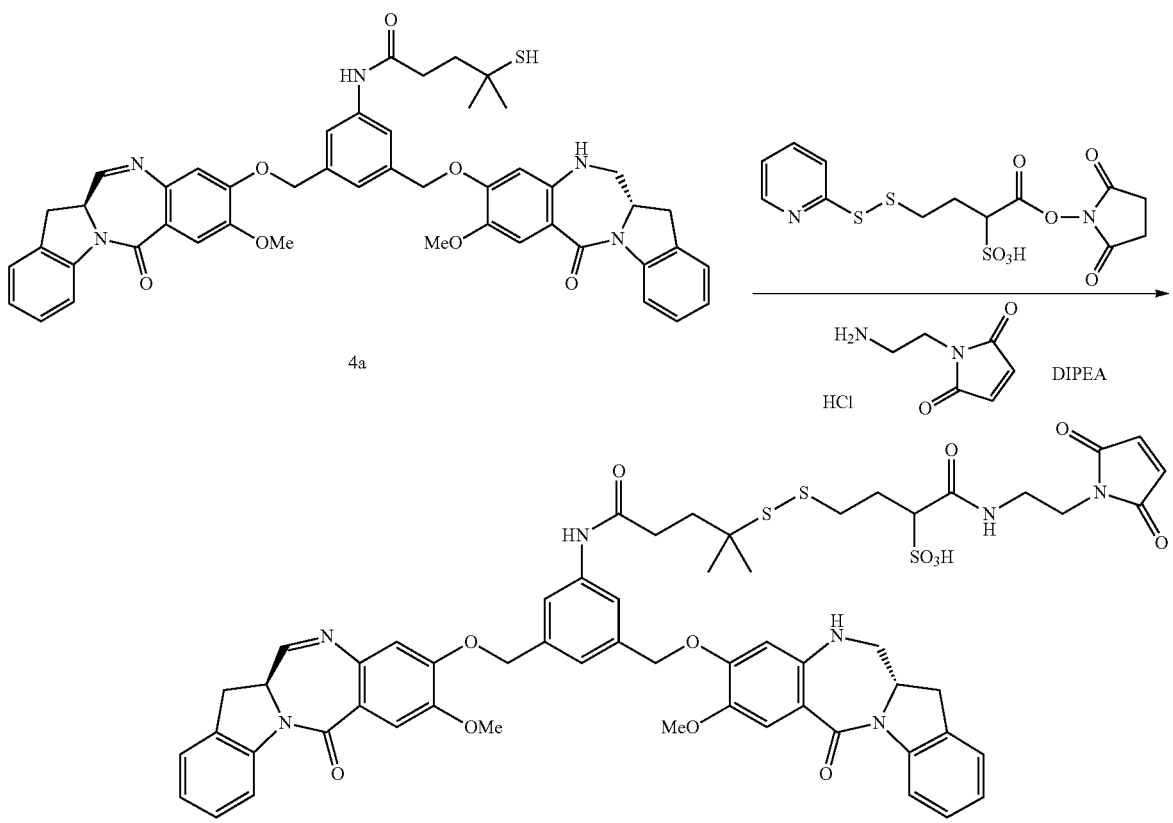

D4

To a suspension of the free thiol, 4a (88 mg, 0.105 mmol) and 1-((2,5-dioxopyrrolidin-1-yl)oxy)-1-oxo-4-(pyridin-2-yldisulfanyl)butane-2-sulfonic acid (64.0 mg, 0.158 mmol) in anhydrous dichloromethane (2.10 mL) was added DIPEA (55.0 µL, 0.315 mmol) under nitrogen at room temperature. The mixture stirred for 16 hours and then 1-(2-aminoethyl)-1H-pyrrole-2,5-dione hydrochloride (55.6 mg, 0.315 mmol), anhydrous dichloromethane (1.0 mL) and DIPEA (0.055 mL, 0.315 mmol) were added. The mixture stirred for an additional 5 hours at room temperature upon which the reaction was concentrated in vacuo. The resulting residue was purified by RP-HPLC (C18, $CH_3CN/H_2O$). Fractions containing desired product were frozen and lyophilized to give maleimide, compound D4 (20 mg, 16% yield) as a white solid. LCMS=4.92 min (8 min method). MS (m/z): 1158.6 (M+1)$^+$.

D. Synthesis of N-(2-(2,5-dioxo-2,5-dihydro-1H-pyrrol-1-yl)ethyl)-11-(3-(((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)-2,5,8-trioxa-11-azapentadecan-15-amide, compound D7

Example 2 Antibody Conjugation to Exemplary Linker-Effector Reagents

Antibody Reagents

An expression vector encoding the heavy chain of the previously described humanized MOV19 antibody (huMOV19, U.S. Pat. No. 8,557,966, incorporated by reference) was mutagenized so that the expressed protein contained a cysteine residue at the EU/OU numbering position 442 at the heavy chain $CH_3$ domain, using standard molecular cloning procedures. The huMOV19-HC-C442 IgG1 variant (or huMOV19-C442 for short) was expressed in and purified from mammalian cells using established procedures for human IgG1 antibodies. Similar procedures were used to clone, express, and purify multiple variants of the huCD123-6G antibody bearing the same cysteine 442 mutation (e.g., the huCD123-6Gv1.1-C442 and huCD123-6Gv4.7-C442). These huCD123-6 antibodies are described in detail in U.S. Provisional Application No. 62/186,161, filed on Jun. 29, 2015, entitled "ANTI-CD123 ANTIBODIES AND CONJUGATES AND DERIVATIVES THEREOF," the entire contents of which, including all protein and nucleic acid sequences and drawings, are incorporated herein by reference.

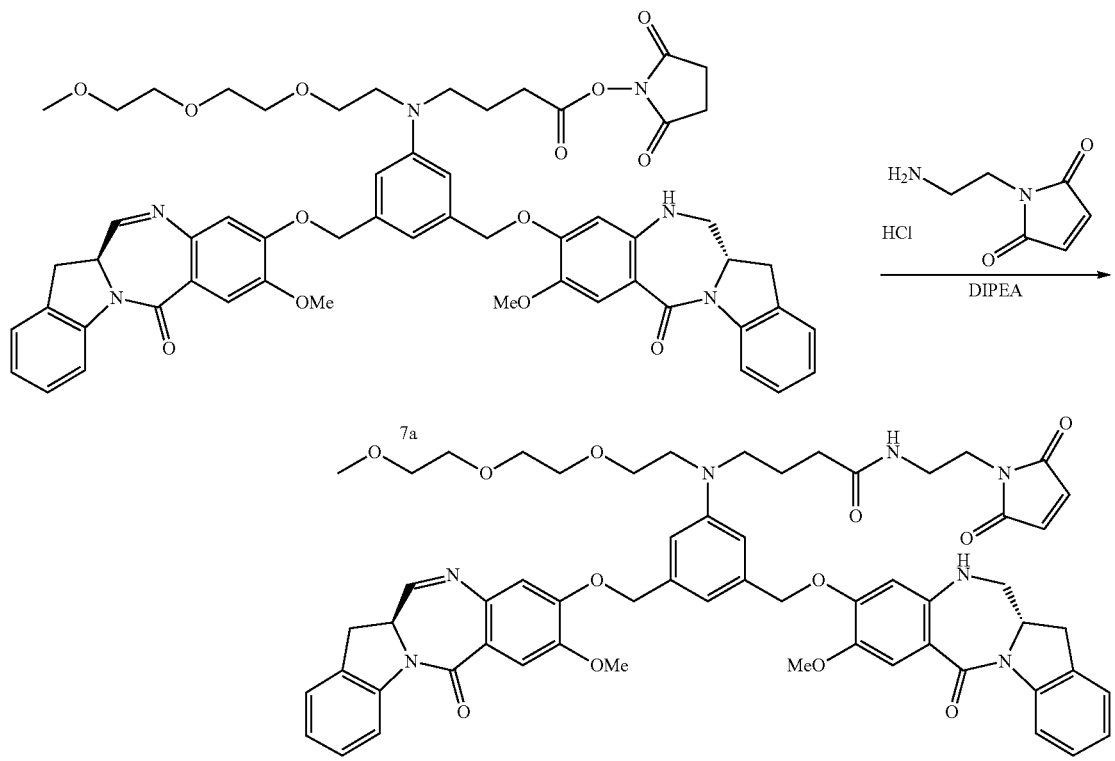

D7

To a solution of NHS ester, 7a (5 mg, 4.82 mol) and 1-(2-aminoethyl)-1H-pyrrole-2,5-dione hydrochloride (1.7 mg, 9.64 mol) in anhydrous dichloromethane (200 µL) was added DIPEA (1.512 µL, 8.68 µmol) under nitrogen. The mixture was stirred at room temperature for 4 hours and then concentrated in vacuo. The resulting residue was purified by RP-HPLC (C18, $CH_3CN/H_2O$). Fractions containing desired product were frozen and lyophilized to give maleimide, compound D7 (3.5 mg, 68% yield). LCMS=4.61 min (15 min method). MS (m/z): 1062.8 (M+1)$^+$.

A. huMOV19-C442-Mal-CX1-1-DM1 huMOV19-C442 antibody bearing two unpaired cysteine residues (at the C442 position of the heavy chain $CH_3$ region) in the reduced state was prepared using standard protein chemistry procedures. To a solution of this intermediate in phosphate buffered saline (PBS), 5 mM N,N,N',N'-ethylenediaminetetracetic acid (EDTA) pH 6.0 was added N,N-dimethylacetamide (DMA) and 8 molar equivalents of Mal-CX1-1-DM1 (see WO 2014/134486) as a stock solution in DMA to give a reaction mixture with a final solvent composition of 10% v/v DMA in PBS 5 mM EDTA pH 6.0. The reaction was allowed to proceed overnight at 25° C.

(DMA) and 6 molar equivalents of Mal-SPDB-DM4 (see WO 2014/134483) as a stock solution in DMA to give a

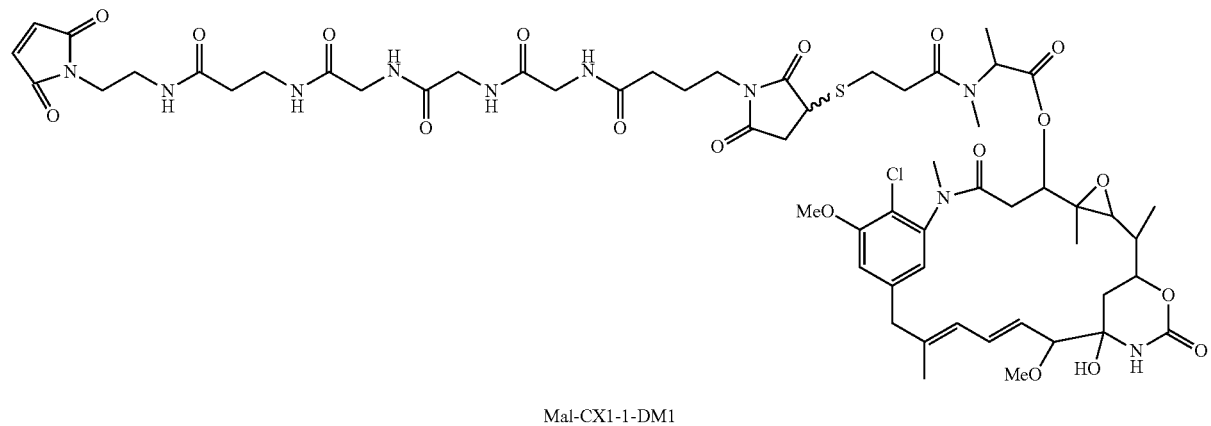 [SMILES: COc1cc2cc(c1Cl)N(C)C(=O)CC(OC(=O)C(C)N(C)C(=O)CCSC1CC(=O)N(CCCC(=O)NCC(=O)NCC(=O)NCC(=O)NCCC(=O)NCCN3C(=O)C=CC3=O)C1=O)C1(C)OC1C(C)C1CC(O)(NC(=O)O1)C(OC)/C=C/C=C(\C)C2]

Mal-CX1-1-DM1

Upon covalent bond formation between the free thiol group of the C442 residues and the maleimido (Mal) group of the Mal-CX1-1-DM1 shown above, the conjugate was reaction mixture with a final solvent composition of 10% v/v DMA in PBS 5 mM EDTA pH 6.0. The reaction was allowed to proceed overnight at 25° C.

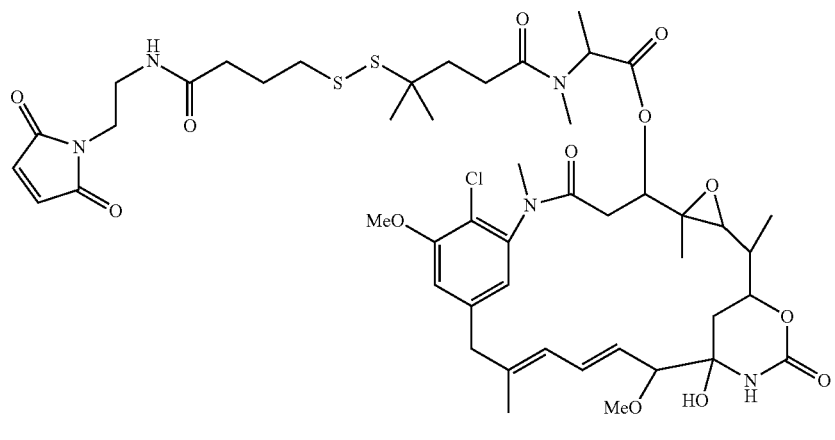

Mal-SPDB-DM4 purified into 10 mM succinate, 250 mM glycine, 0.5% sucrose, 0.01% Tween-20 pH 5.5 formulation buffer using Sephadex G25 desalting columns, concentrated by ultrafiltration through a membrane with 10 kDa molecular weight cutoff, and filtered through a 0.22 μm syringe filter. The conjugate was then dialyzed against the same buffer using a membrane with 10 kDa molecular weight cutoff.

The conjugate was found to have an average of 2 mol DM1/mol antibody by UV-Vis; 99.3% monomer by SEC; and no detectable unconjugated DM1 by HPLC on a HISEP column. LC-MS of the deglycosylated conjugate is shown in FIG. 1A.

B. huMOV19-C442-Mal-SPDB-DM4 huMOV19 antibody bearing two unpaired cysteine residues (at the C442 position of the heavy chain CH₃ region) in the reduced state was prepared using standard procedures. To a solution of this intermediate in phosphate buffered saline (PBS), 5 mM N,N,N',N'-ethylenediaminetetracetic acid (EDTA) pH 6.0 was added N,N-dimethylacetamide The conjugate was purified into 10 mM succinate, 250 mM glycine, 0.5% sucrose, 0.01% Tween-20 pH 5.5 formulation buffer using Sephadex G25 desalting columns, concentrated by ultrafiltration through a membrane with 10 kDa molecular weight cutoff, and filtered through a 0.22 μm syringe filter. The conjugate was then dialyzed against the same buffer using a membrane with 10 kDa molecular weight cutoff.

Figure 1B:
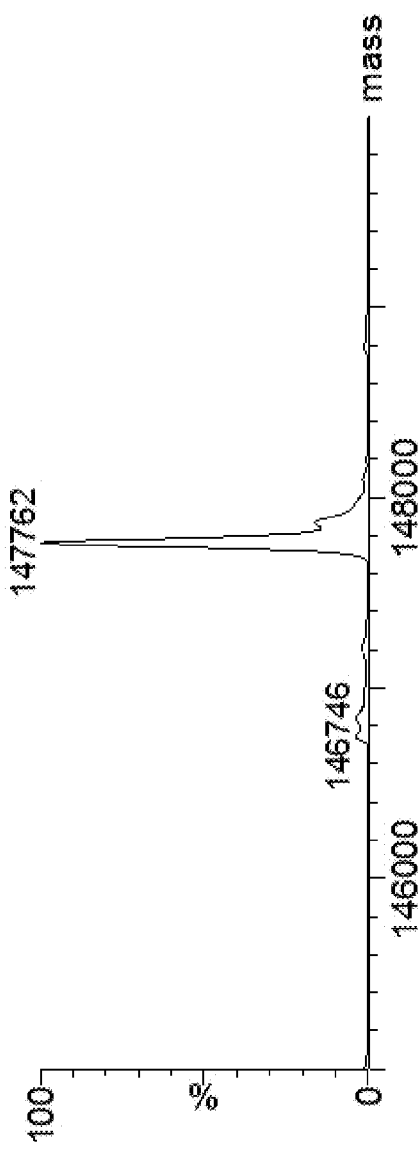
FIG. 1B shows LC-MS of the deglycosylated conjugate huMOV19-C442-Mal-SPDB-DM4, which was found to have an average of 2 mol DM4/mol antibody by UV/Vis; 99.5% monomer by SEC; and 0.8% unconjugated DM4 by HPLC on a HISEP column.

The conjugate was found to have 2 mol DM4/mol antibody by UV-Vis; 99.5% monomer by SEC; and 0.8% unconjugated DM4 by HPLC on a HISEP column. LC-MS of the deglycosylated conjugate is shown in FIG. 1B.

C. huMOV19-C442-D5 huMOV19 antibody bearing two unpaired cysteine residues (at the C442 position of the heavy chain CH₃ region) in the reduced state was prepared using standard procedures. To a solution of this intermediate in phosphate buffered saline (PBS), 5 mM N,N,N',N'-ethylenediaminetetracetic acid (EDTA) pH 6.0 was added N,N-dimethylacetamide (DMA), propylene glycol, and 8 molar equivalents of compound D5 as a stock solution in DMA to give a reaction mixture with a final solvent composition of 2% v/v DMA and 38% v/v propylene glycol in PBS 5 mM EDTA pH 6.0. The reaction was allowed to proceed for 24 hours at 25° C.

The conjugate was purified into 20 mM histidine, 50 mM sodium chloride, 8.5% sucrose, 0.01% Tween-20, 50 μM sodium bisulfite pH 6.2 formulation buffer using Sephadex G25 desalting columns, concentrated by ultrafiltration through a membrane with 10 kDa molecular weight cutoff, and filtered through a 0.22 μm syringe filter. The conjugate was then dialyzed against the same buffer using a membrane with 10 kDa molecular weight cutoff.

The conjugate was found to have an average of 2 mol D5/mol antibody by UV/Vis; 94.6% monomer by SEC; and 0.8% unconjugated D5 by SEC/reverse-phase HPLC. LC-MS of the deglycosylated conjugate is shown in FIG. 1C.

D. huMOV19-C442-D4 huMOV19 antibody bearing two unpaired cysteine residues (at the C442 position of the heavy chain $CH_3$ region) in the reduced state was prepared using standard procedures. To a solution of this intermediate in phosphate buffered saline (PBS), 5 mM N,N,N',N'-ethylenediaminetetracetic acid (EDTA) pH 6.0 was added N,N-dimethylacetamide (DMA), propylene glycol, and 6 molar equivalents of D4 as a stock solution in DMA to give a reaction mixture with a final solvent composition of 2% v/v DMA and 38% v/v propylene glycol in PBS 5 mM EDTA pH 6.0. The reaction was allowed to proceed for 24 hours at 25° C.

The conjugate was purified into 20 mM histidine, 50 mM sodium chloride, 8.5% sucrose, 0.01% Tween-20, 50 μM sodium bisulfite pH 6.2 formulation buffer using Sephadex G25 desalting columns, concentrated by ultrafiltration through a membrane with 10 kDa molecular weight cutoff, and filtered through a 0.22 μm syringe filter. The conjugate was then dialyzed against the same buffer using a membrane with 10 kDa molecular weight cutoff.

The conjugate was found to have an average of 2 mol D4/mol antibody by UV-Vis; 92.1% monomer by SEC; and 0.3% unconjugated D4 by SEC/reverse-phase HPLC. LC-MS of the deglycosylated antibody is shown in FIG. 1D.

E. huCD123-6Gv1.1S2-C442-D7 huCD123 antibody bearing two unpaired cysteine residues (at the C442 position of the heavy chain $CH_3$ region) in the reduced state (and an engineered N-terminal Ser on the heavy chain) was prepared using standard procedures. To a solution of this intermediate in phosphate buffered saline (PBS), 5 mM N,N,N',N'-ethylenediaminetetracetic acid (EDTA) pH 6.0 was added N,N-dimethylacetamide (DMA), propylene glycol, and 10 molar equivalents of compound D7 as a stock solution in DMA to give a reaction mixture with a final solvent composition of 2% v/v DMA and 38% v/v propylene glycol in PBS 5 mM EDTA pH 6.0. The reaction was allowed to proceed for 24 hours at 25° C.

The conjugate was purified into 20 mM histidine, 50 mM sodium chloride, 8.5% sucrose, 0.01% Tween-20, 50 μM sodium bisulfite pH 6.2 formulation buffer using Sephadex G25 desalting columns, concentrated by ultrafiltration through a membrane with 10 kDa molecular weight cutoff, and filtered through a 0.22 μm syringe filter. The conjugate was then dialyzed against the same buffer using a membrane with 10 kDa molecular weight cutoff.

Figure 1E:
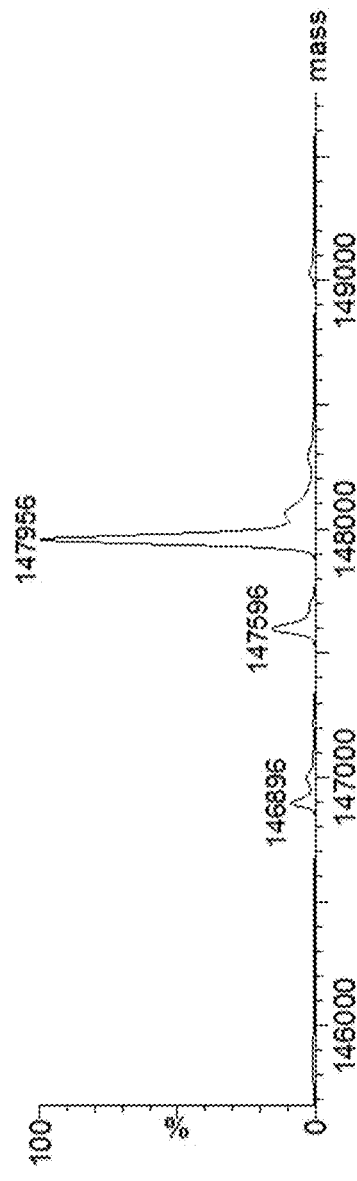
FIG. 1E shows LC-MS of the deglycosylated conjugate huCD123-6Gv1.1S2-C442-D7, which was found to have an average of 2 mol D7/mol antibody by UV-Vis; 97.2% monomer by SEC; and 1.9% unconjugated D7 by SEC/reverse-phase HPLC.

The conjugate was found to have 2 mol D7/mol antibody by UV-Vis; 97.2% monomer by SEC; and 1.9% unconjugated D7 by SEC/reverse-phase HPLC. LC-MS of the deglycosylated conjugate is shown in FIG. 1E.

F. huCD123-6Gv4.7-C442-D5/huCD123-6Gv4.6-C442-D5 huCD123 antibody (huCD123-6Gv4.7-C442 or huCD123-6Gv4.6-C442) bearing two unpaired cysteine residues in the reduced state was prepared using standard procedures. Both huCD123 antibodies have an engineered Cys residue at the EU/OU numbering position 442 in the heavy chain $CH_3$ region, and only differ at the $2^{nd}$ residue from the heavy chain N-termini (i.e., Val for huCD123-6Gv4.7-C442, and Phe for huCD123-6Gv4.6-C442).

To a solution of this intermediate in phosphate buffered saline (PBS), 5 mM N,N,N',N'-ethylenediaminetetracetic acid (EDTA) pH 6.0 was added N,N-dimethylacetamide (DMA), propylene glycol, and 10 molar equivalents of compound D5 as a stock solution in DMA to give a reaction mixture with a final solvent composition of 2% v/v DMA and 38% v/v propylene glycol in PBS 5 mM EDTA pH 6.0. The reaction was allowed to proceed for 24 hours at 25° C.

The conjugate was purified into 20 mM histidine, 50 mM sodium chloride, 8.5% sucrose, 0.01% Tween-20, 50 μM sodium bisulfite pH 6.2 formulation buffer using Sephadex G25 desalting columns, concentrated by ultrafiltration through a membrane with 10 kDa molecular weight cutoff, and filtered through a 0.22 μm syringe filter. The conjugate was then dialyzed against the same buffer using a membrane with 10 kDa molecular weight cutoff.

Figure 1F:
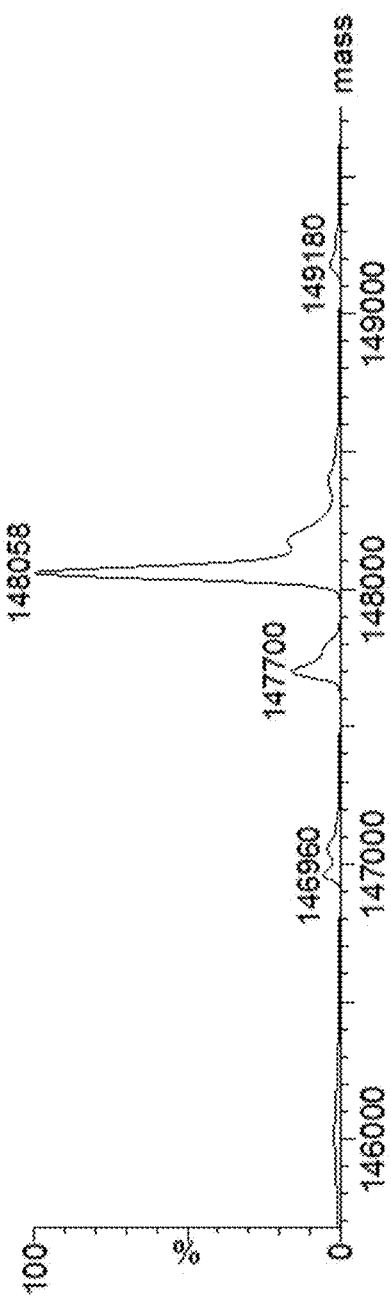
FIG. 1F shows LC-MS of the deglycosylated conjugate huCD123-6Gv4.7-C442-D5, which was found to have an average of 2 mol D5/mol antibody by UV-Vis and 94.8% monomer by SEC.

The conjugate was found to have an average of 2 mol D5/mol antibody by UV-Vis; and 94.8% monomer by SEC. LC-MS of the deglycosylated conjugate is shown in FIG. 1F.

G. huCD123-6Gv4.7-C442-D4/huCD123-6Gv4.6-C442-D4 huCD123 antibody bearing two unpaired cysteine residues (huCD123-6Gv4.7-C442 and huCD123-6Gv4.6-C442, see above) in the reduced state was prepared using standard procedures.

To a solution of this intermediate in phosphate buffered saline (PBS), 5 mM N,N,N',N'-ethylenediaminetetracetic acid (EDTA) pH 6.0 was added N,N-dimethylacetamide (DMA), propylene glycol, and 5 molar equivalents of compound D4 as a stock solution in DMA to give a reaction mixture with a final solvent composition of 2% v/v DMA and 38% v/v propylene glycol in PBS 5 mM EDTA pH 6.0. The reaction was allowed to proceed for 6 hours at 25° C.

The conjugate was purified into 20 mM histidine, 50 mM sodium chloride, 8.5% sucrose, 0.01% Tween-20, 50 μM sodium bisulfite pH 6.2 formulation buffer using Sephadex G25 desalting columns, concentrated by ultrafiltration through a membrane with 10 kDa molecular weight cutoff, and filtered through a 0.22 μm syringe filter. The conjugate was then dialyzed against the same buffer using a membrane with 10 kDa molecular weight cutoff.

Figure 1G:
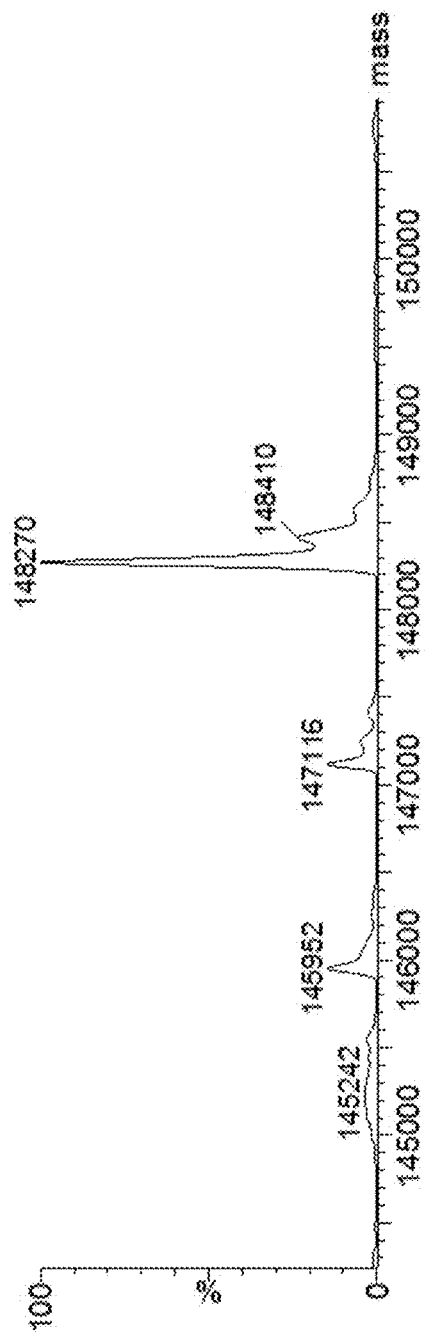
FIG. 1G shows LC-MS of the deglycosylated conjugate huCD123-6Gv4.7-C442-D4, which was found to have an average of 1.8 mol D4/mol antibody by UV-Vis; and 97.4% monomer by SEC.

The conjugate was found to have 1.8 mol D4/mol antibody by UV-Vis; and 97.4% monomer by SEC. LC-MS of the deglycosylated conjugate is shown in FIG. 1G.

Figure 8:
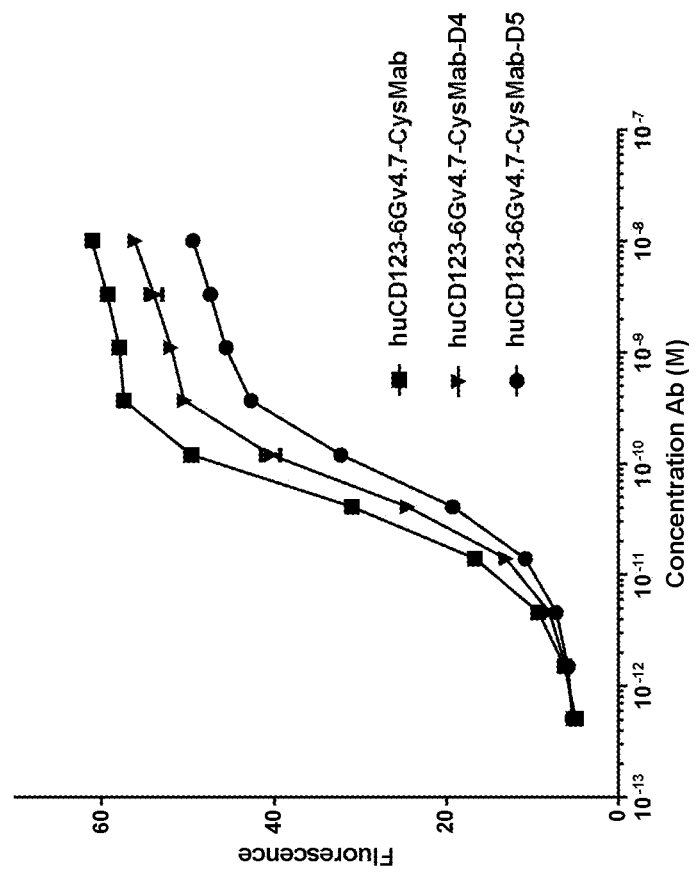
FIG. 8 shows that conjugation of the huCD123-6Gv4.7 antibody via Cys-linkage to the D4 and D5 compounds only moderately affected the binding affinities of the conjugates.

FIG. 8 shows that conjugation of the huCD123-6Gv4.7 antibody via Cys-linkage to the D4 and D5 compounds only moderately affected the binding affinities of the conjugates.

Example 3 In Vitro Potency of huCD123-6Rv1.1-C442-D5 on CD123-Expressing Cells

The ability of huCD123-6Rv1.1-C442-D5 to kill cells that express CD123 on their cell surface was compared to that of the lysine-linked conjugate containing the same antibody and the payload (huCD123-6Rv1.1-D2) using in vitro cytotoxicity assays.

For the chimeric anti-CD123 antibody (chCD123), the confirmed variable region amino acid sequences for the murine CD123 antibodies were codon-optimized, synthesized and cloned in-frame with human antibody constant regions by Blue Heron Biotechnology to build chimeric versions of the CD123 antibodies using the human IgG1 and Kappa constant sequences for the heavy and light chains, respectively.

The cell lines were cultured in culture medium as recommended by the cell supplier (ATCC or DSMZ). The cells, 2,000 to 10,000 in 100 μL of the culture medium, were added to each well of flat bottom 96-well plates. To block Fc receptors on the cell surface, the culture medium was supplemented with 100 nM chKTI antibody (an antibody of the same isotype). Conjugates were diluted into the culture medium using 3-fold dilution series, and 100 μL were added per well. To determine the contribution of CD123-independent cytotoxicity, CD123 blocking antibody—100 nM of the chCD123-6 antibody—was added to some wells prior to adding the testing conjugates. Negative control wells containing cells and the medium but lacking the conjugates, as well as wells contained medium only, were included in each assay plate. Assays were performed in triplicate for each data point. The plates were incubated at 37° C. in a humidified 6% $CO_2$ incubator for 4 to 7 days. Then the relative number of viable cells in each well was determined using the WST-8 based Cell Counting Kit-8 (Dojindo Molecular Technologies, Inc., Rockville, Md.). The apparent surviving fraction of cells in each well was calculated by first correcting for the medium background absorbance, and then dividing each value by the average of the values in the control wells (non-treated cells). The surviving fraction of cells was plotted against conjugate concentration in semi-log plots.

The data showed that the huCD123-6Rv1.1-C442-D5 conjugate was at least as active as the lysine-linked huCD123-6Rv1.1-D2 conjugate on multiple cell lines. Several examples of the cytotoxicity assay using the AML cell line EOL-1, the B-ALL cell line KOPN-8, and the CML cell line MOLM-1, are shown in FIG. 2.

Both conjugates killed the cells in a dose-dependent manner, with the $IC_{50}$ values of approximately 0.002 nM, 0.005 nM and 0.02 nM for EOL-1 cells, KOPN-8 cells, and MOLM-1 cells, respectively. The killing was CD123-dependent, as the conjugates were at least 100 fold less toxic to the cells when the CD123 antigen was blocked by the unconjugated chCD123-6 antibody.

Example 3a In Vitro Potency of huCD123-6Rv1.1-C442-D5' on CD123-Expressing Cells The huCD123 conjugate of D5', a DNA cross-linker, was prepared according to similar procedures described in Example 2. The in vitro potency of the resulting conjugate were tested against various AML progenitor cells. The median $IC_{50}$ value is in the picomolar range.

Example 4. In Vitro Potency of huMOV19-C442 Conjugates on FRα+ Cell Lines

The ability of huMOV19-C442-D5 and huMOV19-C442-D4 to kill cells that express folate receptor alpha (FRα) on their cell surface was compared to that of the lysine-linked conjugate containing the same antibody and the payload (huMOV19-D2 and huMOV19-sulfo-SPDB-D1) using in vitro cytotoxicity assays. The cell lines were cultured in culture medium as recommended by the cell supplier (ATCC or DSMZ). To each well of a flat bottom 96-well plate was added 1,000-2,000 cells in 100 μL of the culture medium. Conjugates were diluted into the culture medium using 3-fold dilution series and 100 μL were added per well. To determine the contribution of FRα-independent cytotoxicity, cells in some wells were pre-incubated with 2 μM huMOV19 antibody prior to the addition of conjugates ("blocked" or "+B"). Control wells containing cells and the medium but lacking the conjugates, as well as wells containing medium only, were included in each assay plate. Assays were performed in triplicate for each data point. The plates were incubated at 37° C. in a humidified 6% $CO_2$ incubator for 5 to 6 days. Then the relative number of viable cells in each well was determined using either the Alamar Blue reagent according the manufacturer's protocol (Life Technologies) or the WST-8 based Cell Counting Kit-8 (Dojindo Molecular Technologies, Inc., Rockville, Md.). The apparent surviving fraction of cells in each well was calculated by first correcting for the medium background absorbance, and then dividing each value by the average of the values in the control wells (non-treated cells). The surviving fraction of cells was plotted against conjugate concentration in semi-log plots.

Figure 3A:
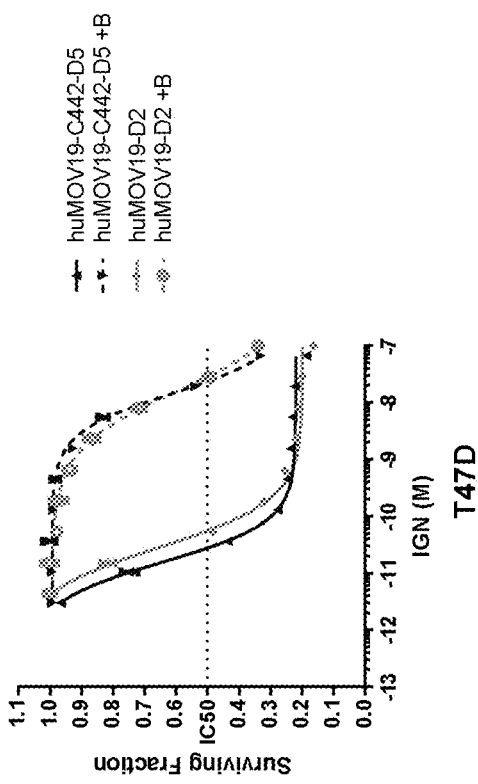
FIGS. 3A, 3B and 3C show that the Cys-linked conjugates are at least as active as the Lys-linked conjugates across multiple target cell lines (e.g., the KB cells, the T47D cells, and the KB cells, respectively) expressing an antigen (i.e., FRα) recognized by the antibody of the conjugates (i.e., M9346A or Mov19). The data curves designated "+B" are the respective controls with excess unconjugated competing antibodies (i.e., unconjugated M9346A antibody).
Figure 3B:
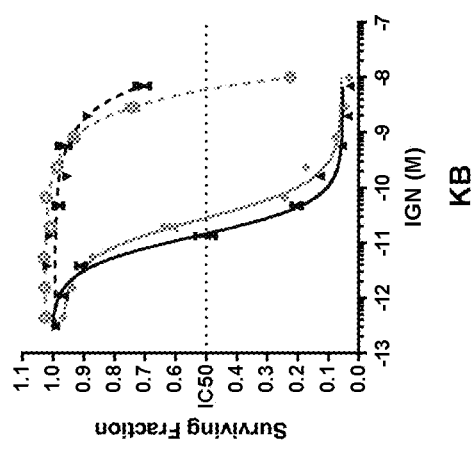

The Cys-linked huMOV19-C442-D5 conjugate was at least as active as the Lys-linked huMOV19-D2 conjugate on multiple cell lines. Two examples of the cytotoxicity assay using the cervical carcinoma KB cell line and the metastatic breast cancer T47D cell line are shown in FIGS. 3A and 3B. Both conjugates killed the cells in a dose-dependent manner with the $IC_{50}$ values of approximately 0.007-0.01 nM for KB and 0.01-0.02 nM for T47D (on a molar antibody basis). The killing was FRα-dependent as the conjugates were at least 100 fold less toxic to the cells when the FRα antigen was blocked by unconjugated huMOV19 antibody.

Figure 3C:
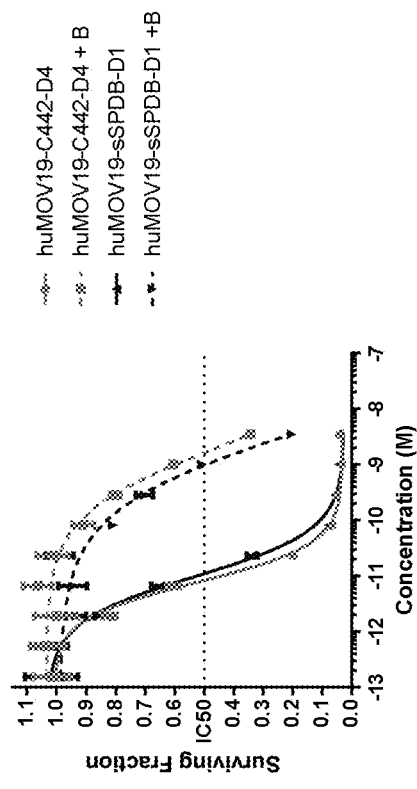

Similarly, the huMOV19-C442-D4 conjugate was tested on KB cells and found to be at least as active as the lysine-linked huMOV19-sulfo-SPDB-D1 conjugate. Exemplary cytotoxicity assay data are shown in FIG. 3C. Both conjugates killed cells in a dose-dependent manner with an $IC_{50}$ values of approximately 0.009-0.01 nM. The killing was FRα-dependent as the conjugates were at least 100 fold less toxic to the cells when the FRα antigen was blocked by unconjugated huMOV19 antibody.

Example 5. Bystander Activity

About 50 μL/well of conjugate (either Cys-linked huMOV19-C442-D5 conjugate or Lys-linked huMOV19-D2 conjugate) were each diluted in RPMI-1640 (Life Technologies) supplemented with heat-inactivated 10% FBS (Life Technologies), 0.1 mg/mL gentamycin (Life Technologies) and βME (Life Technologies) in a 96-well plate (Falcon, round bottom) at concentrations of $1\times10^{-10}$ μM and $4\times10^{-10}$ μM in sextuplicate. Both 300.19 cells (mouse) expressing recombinant FOLR1(FR1 #14) or no expression vector (parental) were counted on a hemacytometer. 50 μL/mL of 1000 FR1 #14 cells/well were added to wells containing conjugate or media only, 50 μL/mL of 2000 parental cells/well were added to wells containing conjugate or media only, and both FR1 #14 and parental cells were added together to wells containing conjugate or media only. All plates were incubated in a 37° C. incubator with 5% $CO_2$ for 4 days. Total volume was 150 μL/well. After incubation, cell viability was analyzed by addition of 75 μL/well Cell Titer Glo (Promega) and allowed to develop for 30 min. Luminescence was read on a luminometer and background in wells containing media only was subtracted from all values. A bar graph of the average of each cell treatment was graphed using Graph Pad Prism.

Figure 4A:
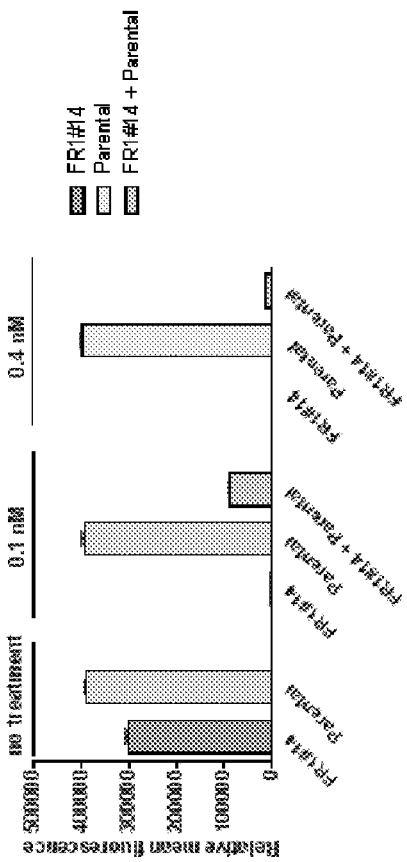
FIGS. 4A and 4B show that the Cys-linked huMOV19-C442-D5 conjugate and the Lys-linked huMOV19-D2 conjugate have nearly the same by-stander killing potency in 300.19 cells.
Figure 4B:
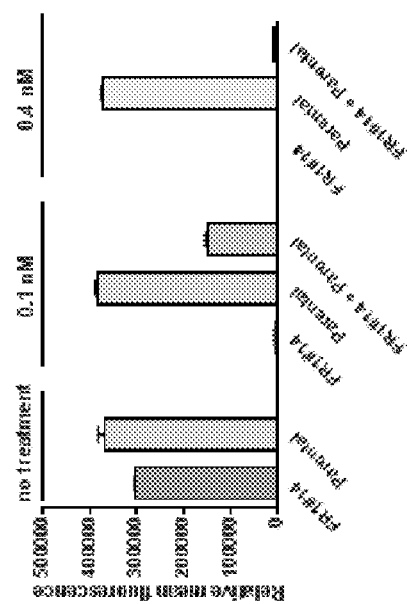

As shown in FIGS. 4A and 4B, both the Cys-linked huMOV19-C442-D5 conjugate and the Lys-linked huMOV19-D2 conjugate show potent bystander killing of proximal antigen negative cells.

Example 6. In Vivo Efficacy of huMOV19-C442-D5 in the NCI-H2110 Mouse Xenograft Model The anti-tumor activity of huMOV19-C442-D5 was evaluated in an established subcutaneous xenograft model of non-small cell lung cancer (NSCLC).

SCID mice (24 animals) were inoculated with NCI-H2110 human NSCLC cells ($1 \times 10^7$ cells/animal) injected subcutaneously into the right flank of the mice. When the tumors reached about 100 mm$^3$ in size (6 days after tumor cell inoculation), the mice were randomly divided into treatment groups of 6 animals each based on tumor volume, and treated with a single intravenous injection of either huMOV19-D2 or huMOV19-C442-D5, each at two doses, according to the following table.
1. Vehicle Control
2. huMOV19-D2 (Lys-linked) 2.7 µg/kg i.v., single
3. huMOV19-D2 (Lys-linked) 8.9 µg/kg i.v., single
4. huMOV19-C442-D5 2.6 µg/kg i.v., single
5. huMOV19-C442-D5 8.7 µg/kg i.v., single Doses are given based on D2 or D5 concentration. At the higher doses, all of the ADCs were highly active to the same extent against NCI-H2110 xenografts (average T/C=1-2%, day 22) with complete regressions in 6/6 animals. At the lower doses, both of the ADCs were active to a similar extent, with huMOV19-D2 resulting in average T/C=32% (day 22), and huMOV19-C442-D5 resulting in average T/C=39% (day 22).

Figure 5:
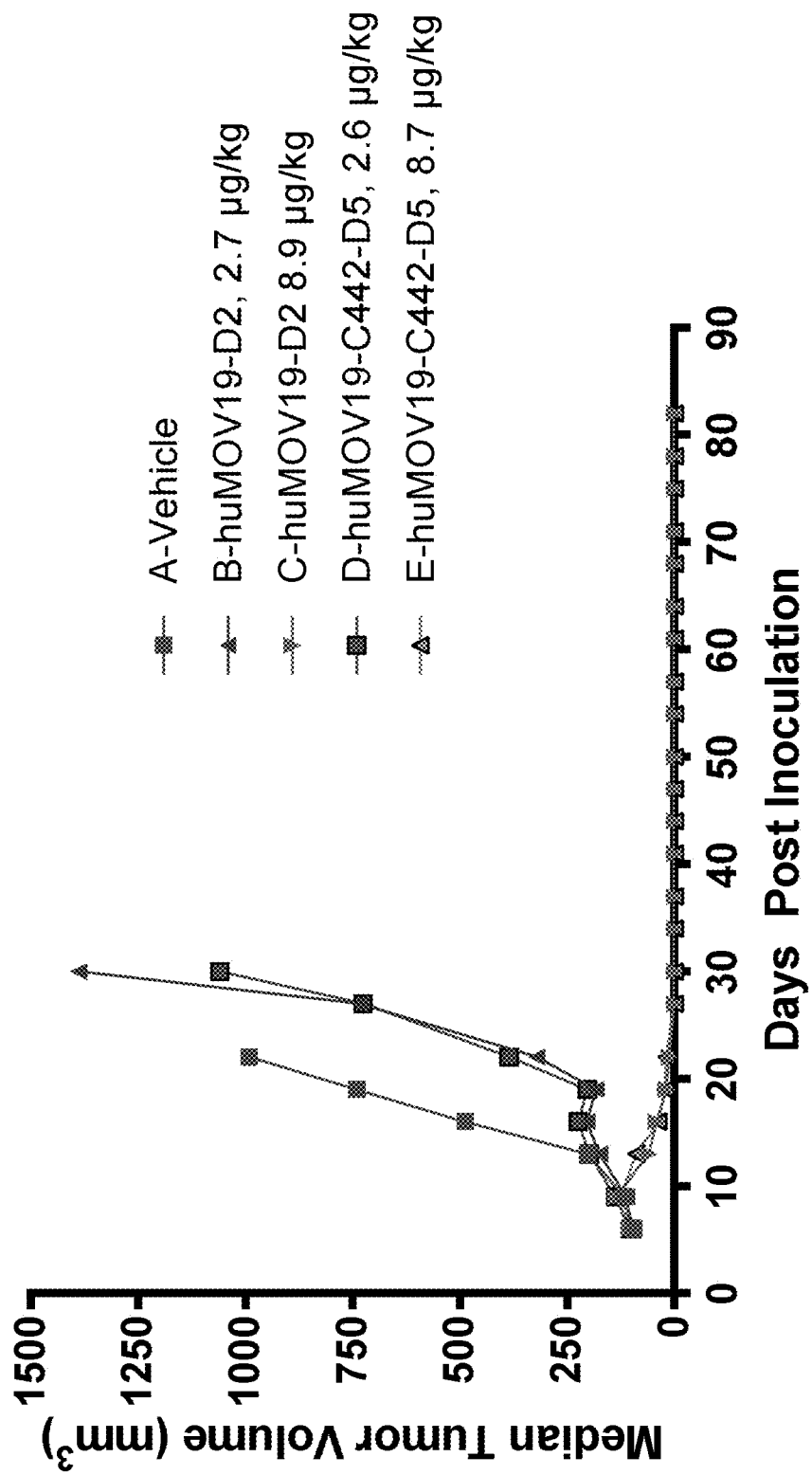
FIG. 5 demonstrates that Cys-linked huMOV19-C442-D5 conjugate and the Lys-linked huMOV19-D2 conjugates have similar activity in NCI-H2110 NSCLC xenograft models, independent of the conjugation type (e.g., Lys-linkage vs. Cys-linkage). All mice received a single i.v. injection of the respective ADCs at the indicated dose after the xenograft tumors reaches about 100 mm³ in size.

See results summarized in the table below. Also see FIG. 5.

| | Group | % T/C (Day 22) | Regressions PR | CR | Result |
|---|---|---|---|---|---|
| A | Vehicle | — | — | — | — |
| B | huMOV19-D2, 2.7 µg/kg | 32% | 0/6 | 0/6 | Active |
| C | huMOV19-D2, 8.9 µg/kg | 1% | 6/6 | 6/6 | Highly Active |
| D | huMOV19-C442-D5, 2.6 µg/kg | 39% | 0/6 | 0/6 | Active |
| E | huMOV19-C442-D5, 8.7 µg/kg | 2% | 6/6 | 6/6 | Highly Active |

The results demonstrate that all conjugates tested are similarly active in NCI-H2110 NSCLC xenograft models, independent of the conjugation type or site of conjugation.

Example 7. Pharmacokinetics of huMOV19-C442-D5 in Mice

The pharmacokinetics of huMOV19-C442-D5 were evaluated in female CD1 mice. Female CD1 mice of approximately 7 weeks of age (9 animals) received a single intravenous injection of 2.5 mg/kg huMOV19-C442-D5. Blood was then collected from the retro-orbital sinus at the following time points: 2 and 30 minutes; 2, 4, and 8 hours; 1, 2, 3, 5, 7, 10, 14, 21, and 28 days. Samples were collected on a rotating basis with n=3 animals per time point and no animals sampled more than twice in 24 hours. Blood samples were centrifuged and plasma decanted to polypropylene tubes, then stored at −80° C. until analysis.

Plasma concentrations of the huMOV19 antibody were determined with an ELISA assay using plates coated with goat anti-human IgG for capture, and an anti-human IgG Fc linked to horseradish peroxidase for detection. The limit of quantitation for the assay was 1.6 ng/mL. Plasma concentrations of D5 linked to human IgG were determined with an ELISA assay using plates coated with an anti-indolinobenzodiazepine compound antibody and detected using the same anti-human IgG Fc/horseradish peroxidase reagent as for the antibody assay above. The LOQ for this assay was 1.0 ng/mL. For each timepoint, the mean plasma concentration from each of the three individual animal samples are reported.

Figure 6:
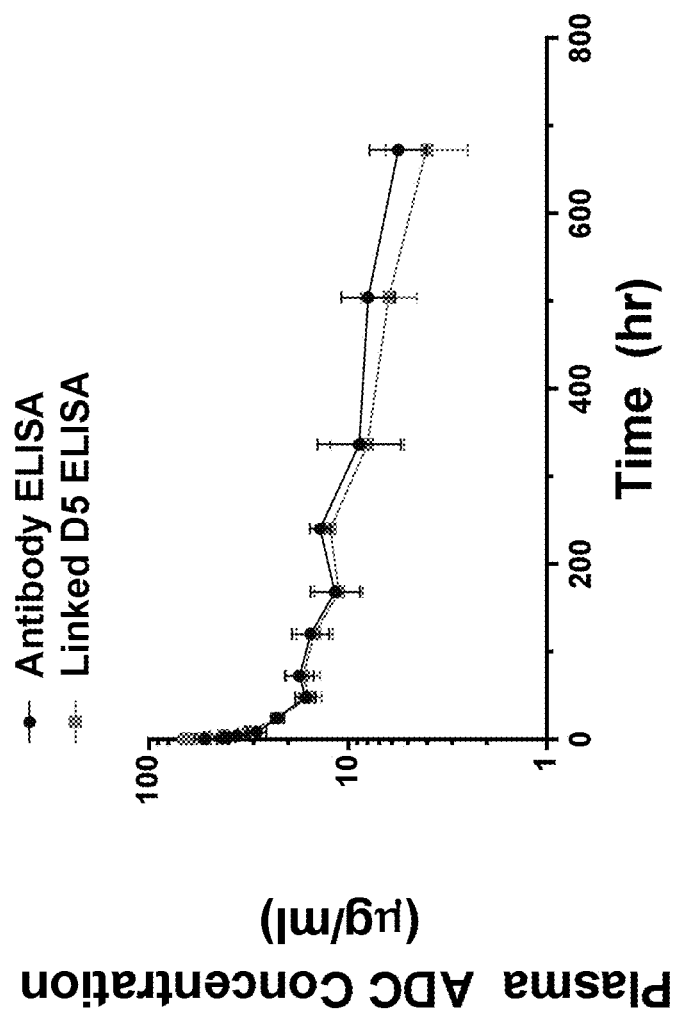
FIG. 6 shows pharmacokinetics of the huMOV19-C442-D5 ADC in CD1 mice over 28 days.

As shown in FIG. 6, the conjugate has similar pharmacokinetic profile as the unconjugated antibody.

Figure 7B:
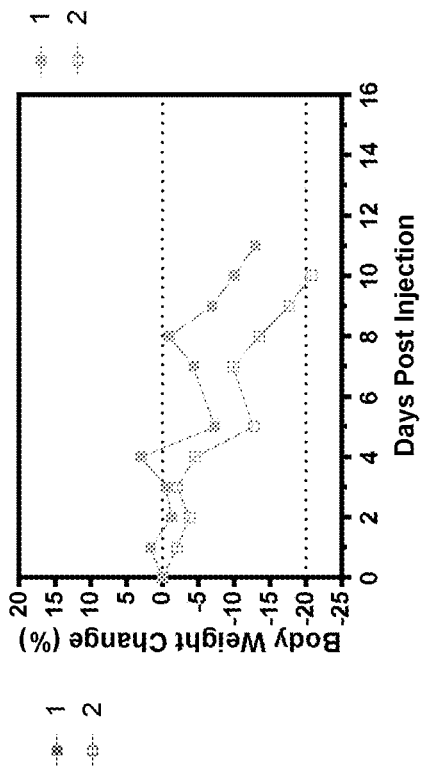
FIG. 7B shows individual body weight percent change of female CD-1 Mice treated with 250 µg/kg CysMab site-specific huMOV19-C442-D5.
Figure 7A:
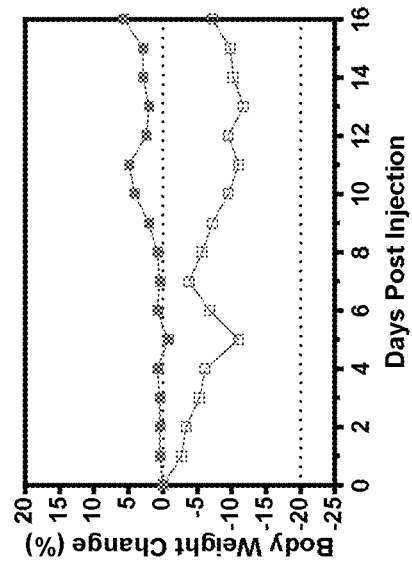
FIG. 7A shows individual body weight percent change of female CD-1 mice treated with 200 µg/kg CysMab site-specific huMOV19-C442-D5.
Figure 7C:
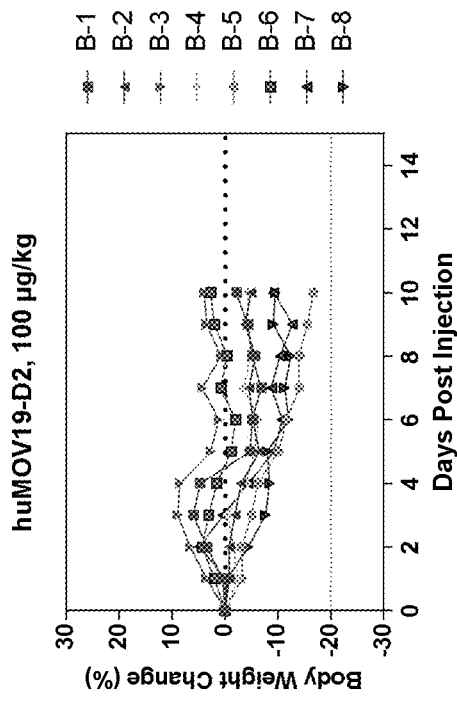
FIG. 7C shows individual body weight percent change of female CD-1 Mice treated with 100 µg/kg Lys-linked huMOV19-D2.
Figure 7D:
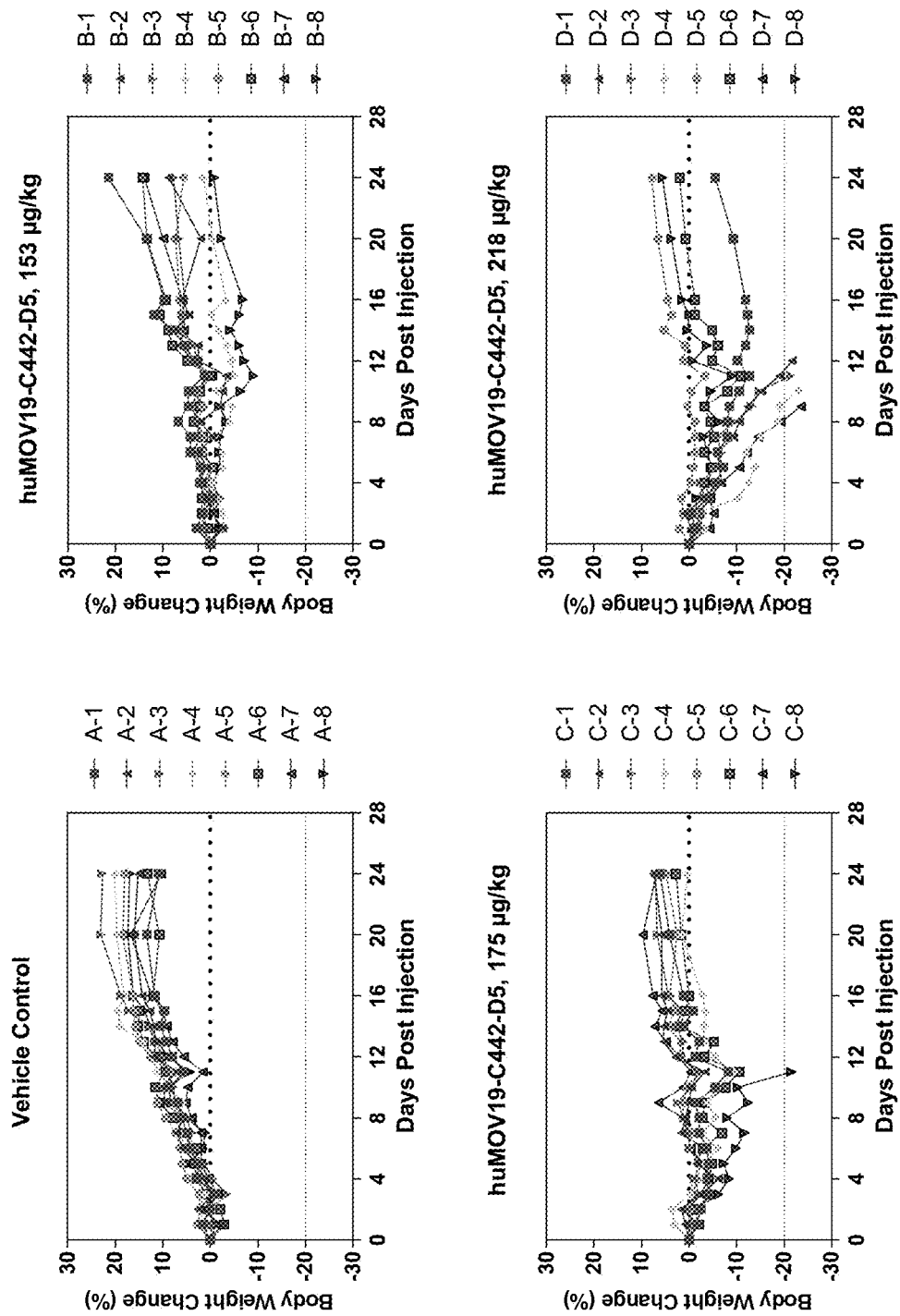
FIG. 7D shows individual body weight percent change of female CD-1 Mice treated with vehicle control, or 175, 200, or 250 µg/kg site-specific huMOV19-C442-D5 conjugate.

Example 8 Acute Tolerability of Single-Dose huMOV19-C442-D5 in Female CD-1 Mice Female CD-1 mice, 7 weeks old, were received from Charles River Laboratories. Mice were housed for an acclimation period of at least 7 days upon arrival prior to study initiation. Pilot tolerability experiments were conducted using 2 mice per group, at doses of huMOV19-C442-D5 at 175 µg/kg (FIG. 7A) or 218 µg/kg (FIG. 7B) based on D5 concentration, in order to determine appropriate doses for a full MTD study.

For the MTD study, animals were randomized into groups (n=8) based on body weight. Mice received a single i.v. administration of vehicle control (0.1 mL/mouse) or huMOV19-C442-D5 at 153, 175, or 218 µg/kg based on D5 concentration. Administration of the drugs was carried out intravenously with a 1.0 mL syringe fitted with a 27 gauge, 2 inch needle. Body weight was measured daily for at least one week and then at least twice weekly for the remainder of the experiment. Body weights (BW) of mice were expressed as percent change in body weight from the pre-treatment body weight as follows:

% BW change=[(BW post/BW pre)−1]×100 where "BW post" is weight after treatment, and "BW pre" is the starting body weight prior to treatment.

Percent body weight loss (BWL) at nadir was expressed as the mean change in body weight post treatment. Animals were sacrificed if body weight dropped more than 20% of initial at any point in the study (1). Mice were also sacrificed if (2) one or both hind legs were paralyzed, or if (3) the animal was too sick to reach food and water.

The table below is a summary of MTD study treatment groups, dosing/schedules, and percent body weight loss at nadir of female CD-1 mice treated intravenously with huMOV19-C442-D5.

| Group | Agent | Route | Total dose (µg/kg) | Dose schedule | Mean injection volume (mL) | Treatment days | Drug death (day of death) | Mean % body weight loss at nadir | Result |
|---|---|---|---|---|---|---|---|---|---|
| A | Vehicle | i.v. | — | qd ×1 | 0.1 | day 0 | 0/8 | — | — |
| B | huMOV19-C442-D5 | i.v. | 153 | qd ×1 | 0.099 | day 0 | 0/8 | 1.83 | Tolerable |

| Group | Agent | Route | Total dose (μg/kg) | Dose schedule | Mean injection volume (mL) | Treatment days | Drug death (day of death) | Mean % body weight loss at nadir | Result |
|---|---|---|---|---|---|---|---|---|---|
| C | huMOV19-C442-D5 | i.v. | 175 | qd ×1 | 0.115 | day 0 | 1/8 (d11) | 7.11 | MTD |
| D | huMOV19-C442-D5 | i.v. | 218 | qd ×1 | 0.142 | day 0 | 4/8 (d10-13) | 10.32 | Intolerable |

We claim:

1. An antibody-cytotoxic agent conjugate represented by the following formula:

Ab~~S₄₄₂—J$_{CB}$'—L—D)$_w$ or a pharmaceutically acceptable salt thereof, wherein:
Ab is an antibody having a cysteine residue at the EU/OU numbering position 442 of a heavy chain of the antibody, and is covalently linked to a linking moiety J$_{CB}$' through the thiol group S₄₄₂ of the cysteine residue;
D is a cytotoxic agent covalently linked to a linker L that is covalently linked to J$_{CB}$';

wherein D is represented by the following structural formula:

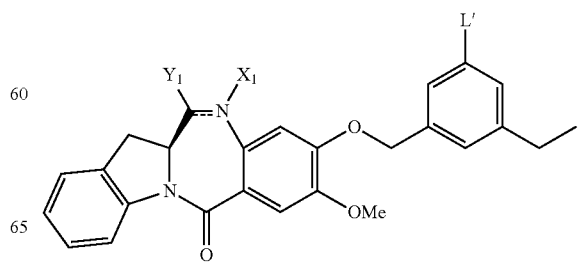

-continued

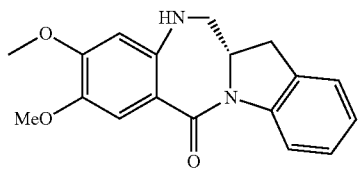

or a pharmaceutically acceptable salt thereof, wherein:
L' is represented by the following formula:

-NR$_5$-P$_1$-C(=O)-(CR$_a$R$_b$)$_s$-C(=O)—     (B1'); or

-NR$_5$-P$_1$-C(=O)-Cy-(CR$_a$R$_b$)$_{s1'}$-C(=O)—     (B2');

P$_1$ is a peptide containing between 2 to 5 amino acid residues, wherein the peptide is cleavable by a protease;
R$_a$ and R$_b$, for each occurrence, are each independently —H, (C$_1$-C$_3$)alkyl or -SO$_3$H;
s is an integer from 1 to 6;
s1' is 0 or 1;
Cy is cyclohexane;
the double line ═ between N and C represents a single bond or a double bond, provided that when it is a double bond X$_1$ is absent and Y$_1$ is —H, and when it is a single bond, X$_1$ is —H; and Y$_1$ is —SO$_3$M, wherein M is H$^+$, Na$^+$ or K$^+$;
R$_5$ is —H or (C$_1$-C$_3$)alkyl
-J$_{CB}$'-L- is represented by the following structural formula:

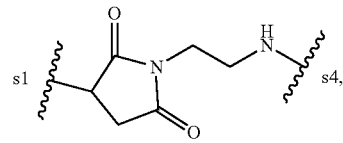

wherein s1 is the site covalently linked to the cysteine residue, and s4 is the site covalently linked to the L' group of D through the —C(=O)—group in formula (B1') or (B2'); and
w is 1 or 2.

2. The conjugate of claim 1, wherein the cysteine residue at position 442 is recombinantly introduced into said Ab.

3. The conjugate of claim 1, wherein D is represented by the following structural formula:

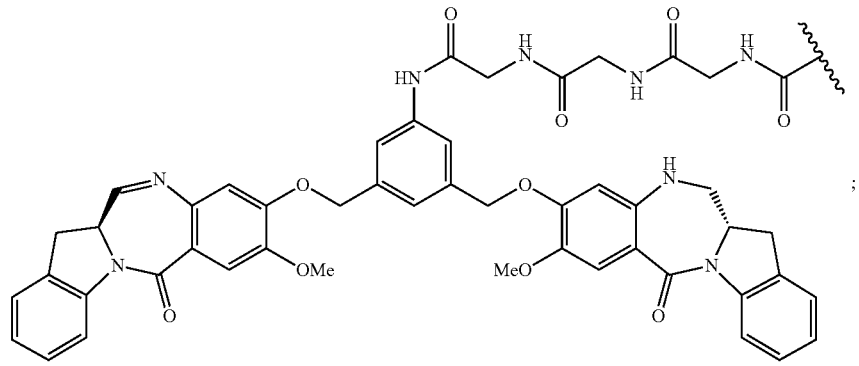

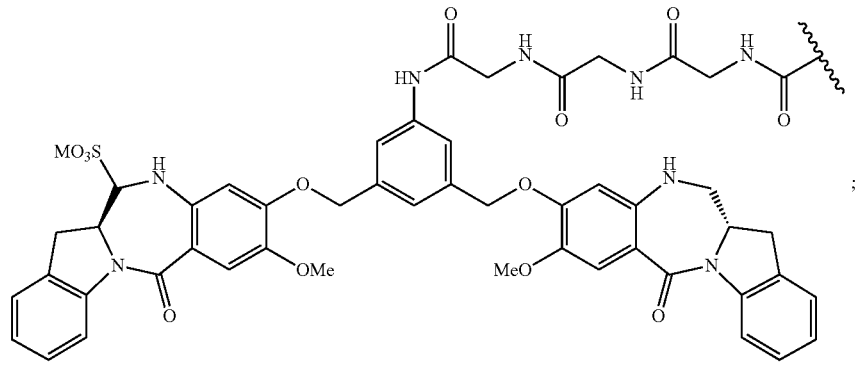

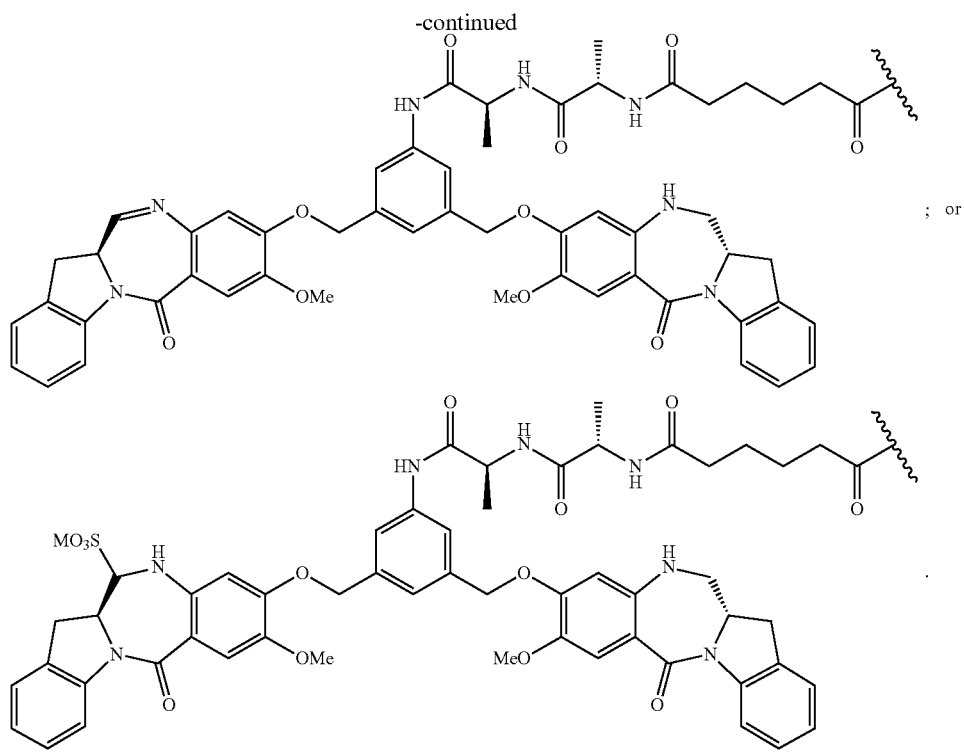
; or
.
4. The conjugate of claim 1, wherein the conjugate is represented by the following structural formula:
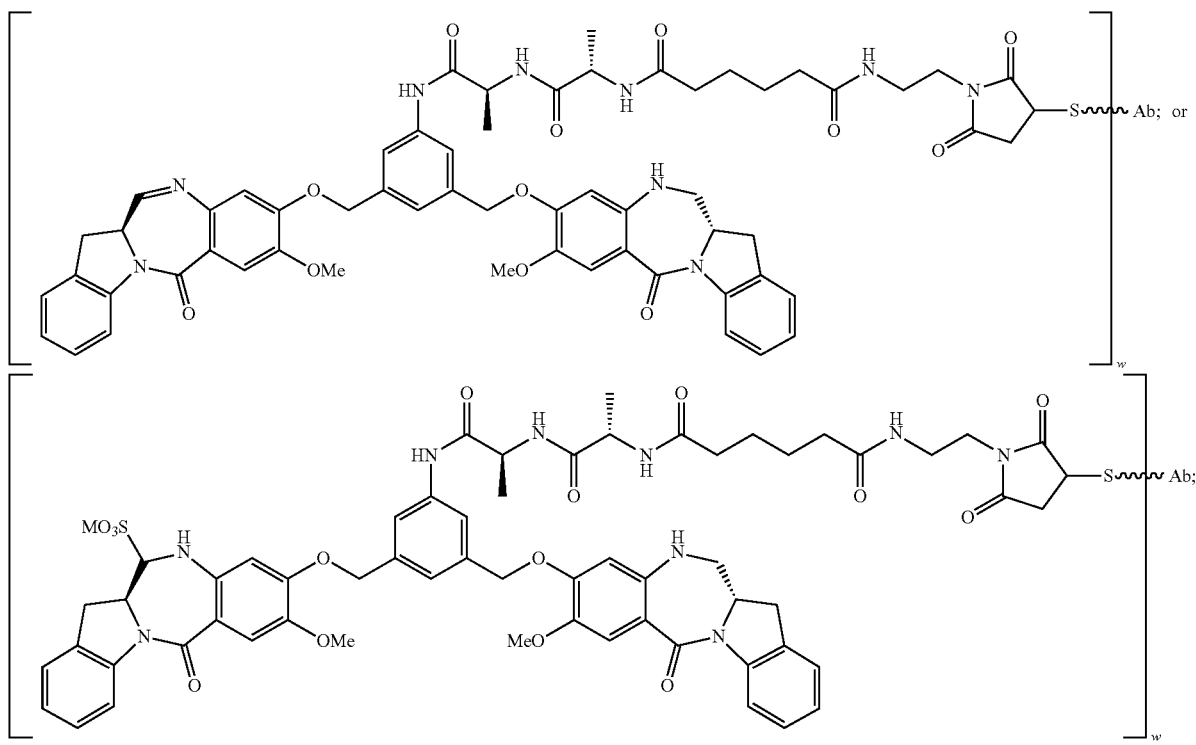
or a pharmaceutically acceptable salt thereof, wherein Ab is an antibody.

5. The conjugate of claim 1, wherein w is 2.

6. A pharmaceutical composition comprising the conjugate of claim 1 and a pharmaceutically acceptable carrier.

7. The conjugate of claim 1, wherein L' is represented by formula (B1').

8. The conjugate of claim 1, wherein $R_a$ and $R_b$ are both H; and $R_5$ is H or Me.

9. The conjugate of claim 8, wherein s1' is 0 or 1.

10. The conjugate of claim 1, wherein $P_1$ is Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 14), β-Ala-Leu-Ala-Leu (SEQ ID NO: 15), Gly-Phe-Leu-Gly (SEQ ID NO: 16), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, or Met-Ala.

11. The conjugate of claim 1, wherein $P_1$ is Gly-Gly-Gly, Ala-Val, Ala-Ala, Ala-D-Ala, D-Ala-Ala, or D-Ala-D-Ala.

* * * * *

UNITED STATES PATENT AND TRADEMARK OFFICE
CERTIFICATE OF CORRECTION

PATENT NO. : 10,898,579 B2  
APPLICATION NO. : 15/195269  
DATED : January 26, 2021  
INVENTOR(S) : Nicholas C. Yoder et al.

Page 1 of 1

It is certified that error appears in the above-identified patent and that said Letters Patent is hereby corrected as shown below:

In the Claims

In Claim 1, Columns 160-161, please replace the formula:

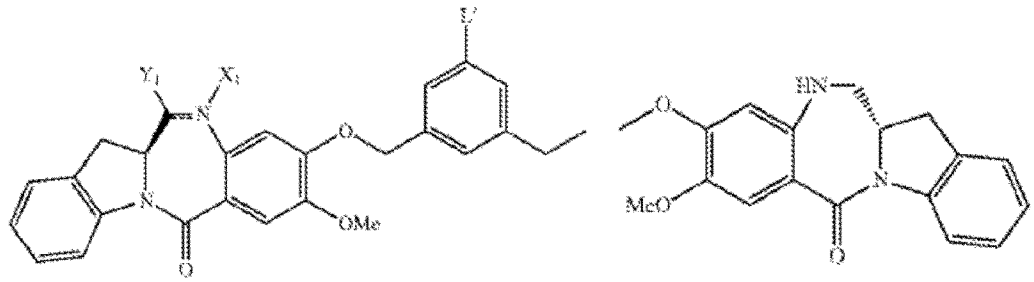

With the following formula:

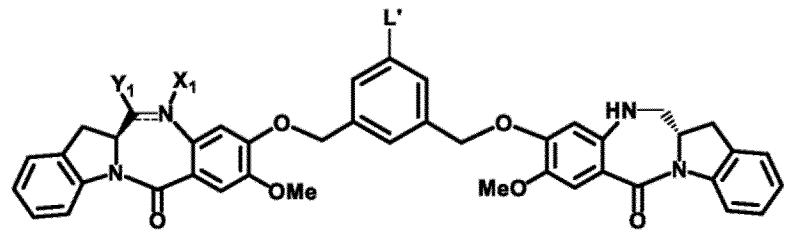

Signed and Sealed this  
Fourth Day of May, 2021

Drew Hirshfeld  
*Performing the Functions and Duties of the  
Under Secretary of Commerce for Intellectual Property and  
Director of the United States Patent and Trademark Office*

SEQUENCE LISTING

<160> NUMBER OF SEQ ID NOS: 16

<210> SEQ ID NO 1
<211> LENGTH: 5
<212> TYPE: PRT
<213> ORGANISM: Artificial
<220> FEATURE:
<223> OTHER INFORMATION: Synthetic Peptide

<400> SEQUENCE: 1

Gly Tyr Phe Met Asn
1               5

<210> SEQ ID NO 2
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (14)..(14)
<223> OTHER INFORMATION: Lys, Gln, His, or Arg
<220> FEATURE:
<221> NAME/KEY: Xaa
<222> LOCATION: (16)..(16)
<223> OTHER INFORMATION: Gln, His, Asn, or Arg
<220> FEATURE:
<221> NAME/KEY: Xaa
<222> LOCATION: (17)..(17)
<223> OTHER INFORMATION: Gly, Glu, Thr, Ser, Ala, or Val

<400> SEQUENCE: 2

Arg Ile His Pro Tyr Asp Gly Asp Thr Phe Tyr Asn Gln Xaa Phe Xaa
1               5                   10                  15

Xaa

<210> SEQ ID NO 3
<211> LENGTH: 9
<212> TYPE: PRT
<213> ORGANISM: Artificial
<220> FEATURE:
<223> OTHER INFORMATION: Synthetic Peptide

<400> SEQUENCE: 3

Tyr Asp Gly Ser Arg Ala Met Asp Tyr
1               5

<210> SEQ ID NO 4
<211> LENGTH: 15
<212> TYPE: PRT
<213> ORGANISM: Artificial
<220> FEATURE:
<223> OTHER INFORMATION: Synthetic Peptide

<400> SEQUENCE: 4

Lys Ala Ser Gln Ser Val Ser Phe Ala Gly Thr Ser Leu Met His
1               5                   10                  15

<210> SEQ ID NO 5
<211> LENGTH: 7
<212> TYPE: PRT
<213> ORGANISM: Artificial
<220> FEATURE:
<223> OTHER INFORMATION: Synthetic Peptide

<400> SEQUENCE: 5

Arg Ala Ser Asn Leu Glu Ala
1               5

<210> SEQ ID NO 6
<211> LENGTH: 9
<212> TYPE: PRT
<213> ORGANISM: Artificial
<220> FEATURE:
<223> OTHER INFORMATION: Synthetic Peptide

<400> SEQUENCE: 6

Gln Gln Ser Arg Glu Tyr Pro Tyr Thr
1               5

<210> SEQ ID NO 7
<211> LENGTH: 17
<212> TYPE: PRT
<213> ORGANISM: Artificial
<220> FEATURE:
<223> OTHER INFORMATION: Synthetic Peptide

<400> SEQUENCE: 7

Arg Ile His Pro Tyr Asp Gly Asp Thr Phe Tyr Asn Gln Lys Phe Gln
1               5                   10                  15

Gly

<210> SEQ ID NO 8
<211> LENGTH: 447
<212> TYPE: PRT
<213> ORGANISM: Artificial
<220> FEATURE:
<223> OTHER INFORMATION: Synthetic Peptide

<400> SEQUENCE: 8

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
    435                 440                 445

<210> SEQ ID NO 9
<211> LENGTH: 218
<212> TYPE: PRT
<213> ORGANISM: Artificial
<220> FEATURE:
<223> OTHER INFORMATION: Synthetic Peptide

<400> SEQUENCE: 9

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 10
<211> LENGTH: 218
<212> TYPE: PRT
<213> ORGANISM: Artificial
<220> FEATURE:
<223> OTHER INFORMATION: Synthetic Peptide

<400> SEQUENCE: 10

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

```
Val Thr Lys Ser Phe Asn Arg Gly Glu Cys
    210                 215
```

<210> SEQ ID NO 11
<211> LENGTH: 118
<212> TYPE: PRT
<213> ORGANISM: Artificial
<220> FEATURE:
<223> OTHER INFORMATION: Synthetic Peptide

<400> SEQUENCE: 11

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

<210> SEQ ID NO 12
<211> LENGTH: 112
<212> TYPE: PRT
<213> ORGANISM: Artificial
<220> FEATURE:
<223> OTHER INFORMATION: Synthetic Peptide

<400> SEQUENCE: 12

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Thr Lys Leu Glu Ile Lys Arg
            100                 105                 110
```

<210> SEQ ID NO 13
<211> LENGTH: 112
<212> TYPE: PRT
<213> ORGANISM: Artificial
<220> FEATURE:
<223> OTHER INFORMATION: Synthetic Peptide

<400> SEQUENCE: 13

```
Asp Ile Val Leu Thr Gln Ser Pro Leu Ser Leu Ala Val Ser Leu Gly
```

```
1               5                   10                  15
Gln Pro Ala Ile Ile Ser Cys Lys Ala Ser Gln Ser Val Ser Phe Ala
                    20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
                100                 105                 110

<210> SEQ ID NO 14
<211> LENGTH: 4
<212> TYPE: PRT
<213> ORGANISM: Artificial
<220> FEATURE:
<223> OTHER INFORMATION: Synthetic Peptide

<400> SEQUENCE: 14

Ala Leu Ala Leu
1

<210> SEQ ID NO 15
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: beta-Ala

<400> SEQUENCE: 15

Xaa Leu Ala Leu
1

<210> SEQ ID NO 16
<211> LENGTH: 4
<212> TYPE: PRT
<213> ORGANISM: Artificial
<220> FEATURE:
<223> OTHER INFORMATION: Synthetic Peptide

<400> SEQUENCE: 16

Gly Phe Leu Gly
1
```